(12) United States Patent
Guo et al.

(10) Patent No.: US 11,961,494 B1
(45) Date of Patent: Apr. 16, 2024

(54) ELECTROMAGNETIC INTERFERENCE REDUCTION IN EXTENDED REALITY ENVIRONMENTS

(71) Applicant: META PLATFORMS TECHNOLOGIES, LLC, Menlo Park, CA (US)

(72) Inventors: Ning Guo, Brooklyn, NY (US); Akshay Yembarwar, Jersey City, NJ (US); Jonathan Reid, Brooklyn, NY (US); Daniel Wetmore, Brooklyn, NY (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 306 days.

(21) Appl. No.: 16/832,978

(22) Filed: Mar. 27, 2020

Related U.S. Application Data

(60) Provisional application No. 62/826,574, filed on Mar. 29, 2019.

(51) Int. Cl.
*G09G 5/36* (2006.01)
*A61B 5/00* (2006.01)
(Continued)

(52) U.S. Cl.
CPC ............... *G09G 5/36* (2013.01); *A61B 5/296* (2021.01); *A61B 5/6803* (2013.01); *G06F 3/014* (2013.01);
(Continued)

(58) Field of Classification Search
CPC ...... G09G 5/36; G09G 2354/00; A61B 5/296; A61B 5/6803; A61B 2562/0219;
(Continued)

(56) References Cited

U.S. PATENT DOCUMENTS 1,411,995 A 4/1922 Dull
3,408,133 A 10/1968 Lee
(Continued)

FOREIGN PATENT DOCUMENTS

CA 2902045 A1 8/2014
CA 2921954 A1 2/2015
(Continued)

OTHER PUBLICATIONS

Gargiulo et al., Giga-Ohm High-Impedance FET Input Amplifiers for Dry Electrode Biosensor Circuits and Systems, Jan. 2011, In book: Integrated Microsystems: Electronics, Photonics, and Biotechnology (pp. 165-194)Chapter: 8Publisher: CRC pressEditors: Iniewski, Kris (Year: 2011).*

(Continued)

*Primary Examiner* — Richard J Hong
(74) *Attorney, Agent, or Firm* — Greenberg Traurig, LLP

(57) ABSTRACT

Methods and systems for reducing electromagnetic interference in analog circuit of a control device for an augmented reality (AR) or virtual reality (VR) system are described. An analog circuit associated with the control device may include at least one amplifier and an analog-to-digital converter coupled to an amplifier by one or more electrical conductors. Electromagnetic interference induced in the one or more electrical conductors by an external AC magnetic field may be reduced using at least one component of the control device configured to reduce the electromagnetic interference.

22 Claims, 16 Drawing Sheets

(51) Int. Cl.
*A61B 5/296* (2021.01)
*G06F 3/01* (2006.01)
*H03F 3/45* (2006.01)
*H03M 1/08* (2006.01)

(52) U.S. Cl.
CPC ......... *G06F 3/017* (2013.01); *H03F 3/45475* (2013.01); *A61B 2562/0219* (2013.01); *G09G 2354/00* (2013.01); *H03M 1/08* (2013.01)

(58) Field of Classification Search
CPC .. A61B 5/00; A61B 5/30; G06F 3/014; G06F 3/017; G06F 1/163; G06F 3/011; G06F 3/01; H03F 3/45475; H03M 1/08; A61F 2/72
See application file for complete search history.

(56) References Cited

U.S. PATENT DOCUMENTS

| | | | |
|---|---|---|---|
| 3,580,243 A | 5/1971 | Johnson |
| 3,620,208 A | 11/1971 | Wayne et al. |
| 3,712,716 A | 1/1973 | Cornsweet et al. |
| 3,735,425 A | 5/1973 | Hoshall et al. |
| 3,880,146 A | 4/1975 | Everett et al. |
| 4,055,168 A | 10/1977 | Miller et al. |
| 4,602,639 A | 7/1986 | Hoogendoorn et al. |
| 4,705,408 A | 11/1987 | Jordi |
| 4,817,064 A | 3/1989 | Milles |
| 4,896,120 A | 1/1990 | Kamil |
| 4,978,213 A | 12/1990 | El Hage |
| 5,003,978 A | 4/1991 | Dunseath, Jr. |
| D322,227 S | 12/1991 | Warhol |
| 5,081,852 A | 1/1992 | Cox |
| 5,103,323 A | 4/1992 | Magarinos et al. |
| 5,231,674 A | 7/1993 | Cleveland et al. |
| 5,251,189 A | 10/1993 | Thorp |
| D348,660 S | 7/1994 | Parsons |
| 5,445,869 A | 8/1995 | Ishikawa et al. |
| 5,462,065 A | 10/1995 | Cusimano |
| 5,467,104 A | 11/1995 | Furness, III et al. |
| 5,482,051 A | 1/1996 | Reddy et al. |
| 5,589,956 A | 12/1996 | Morishima et al. |
| 5,596,339 A | 1/1997 | Furness, III et al. |
| 5,605,059 A | 2/1997 | Woodward |
| 5,625,577 A | 4/1997 | Tosiyasu et al. |
| 5,683,404 A | 11/1997 | Johnson |
| 5,742,421 A | 4/1998 | Wells et al. |
| 6,005,548 A | 12/1999 | Latypov et al. |
| 6,008,781 A | 12/1999 | Furness, III et al. |
| 6,009,210 A | 12/1999 | Kang |
| 6,027,216 A | 2/2000 | Guyton et al. |
| 6,032,530 A | 3/2000 | Hock |
| D422,617 S | 4/2000 | Simioni |
| 6,066,794 A | 5/2000 | Longo |
| 6,184,847 B1 | 2/2001 | Fateh et al. |
| 6,236,476 B1 | 5/2001 | Son et al. |
| 6,238,338 B1 | 5/2001 | DeLuca et al. |
| 6,244,873 B1 | 6/2001 | Hill et al. |
| 6,317,103 B1 | 11/2001 | Furness, III et al. |
| 6,377,277 B1 | 4/2002 | Yamamoto |
| D459,352 S | 6/2002 | Giovanniello |
| 6,411,843 B1 | 6/2002 | Zarychta |
| 6,487,906 B1 | 12/2002 | Hock |
| 6,510,333 B1 | 1/2003 | Licata et al. |
| 6,527,711 B1 | 3/2003 | Stivoric et al. |
| 6,619,836 B1 | 9/2003 | Silvant et al. |
| 6,639,570 B2 | 10/2003 | Furness, III et al. |
| 6,658,287 B1 | 12/2003 | Litt et al. |
| 6,720,984 B1 | 4/2004 | Jorgensen et al. |
| 6,743,982 B2 | 6/2004 | Biegelsen et al. |
| 6,771,294 B1 | 8/2004 | Pulli et al. |
| 6,774,885 B1 | 8/2004 | Even-Zohar |
| 6,807,438 B1 | 10/2004 | Brun Del Re et al. |
| D502,661 S | 3/2005 | Rapport |
| D502,662 S | 3/2005 | Rapport |
| 6,865,409 B2 | 3/2005 | Getsla et al. |
| D503,646 S | 4/2005 | Rapport |
| 6,880,364 B1 | 4/2005 | Vidolin et al. |
| 6,901,286 B1 | 5/2005 | Sinderby et al. |
| 6,927,343 B2 | 8/2005 | Watanabe et al. |
| 6,942,621 B2 | 9/2005 | Avinash et al. |
| 6,965,842 B2 | 11/2005 | Rekimoto |
| 6,972,734 B1 | 12/2005 | Ohshima et al. |
| 6,984,208 B2 | 1/2006 | Zheng |
| 7,022,919 B2 | 4/2006 | Brist et al. |
| 7,028,507 B2 | 4/2006 | Rapport |
| 7,086,218 B1 | 8/2006 | Pasach |
| 7,089,148 B1 | 8/2006 | Bachmann et al. |
| D535,401 S | 1/2007 | Travis et al. |
| 7,173,437 B2 | 2/2007 | Hervieux et al. |
| 7,209,114 B2 | 4/2007 | Radley-Smith |
| D543,212 S | 5/2007 | Marks |
| 7,265,298 B2 | 9/2007 | Maghribi et al. |
| 7,271,774 B2 | 9/2007 | Puuri |
| 7,333,090 B2 | 2/2008 | Tanaka et al. |
| 7,351,975 B2 | 4/2008 | Brady et al. |
| 7,450,107 B2 | 11/2008 | Radley-Smith |
| 7,473,888 B2 | 1/2009 | Wine et al. |
| 7,491,892 B2 | 2/2009 | Wagner et al. |
| 7,517,725 B2 | 4/2009 | Reis |
| 7,558,622 B2 | 7/2009 | Tran |
| 7,574,253 B2 | 8/2009 | Edney et al. |
| 7,580,742 B2 | 8/2009 | Tan et al. |
| 7,596,393 B2 | 9/2009 | Jung et al. |
| 7,618,260 B2 | 11/2009 | Daniel et al. |
| 7,636,549 B2 | 12/2009 | Ma et al. |
| 7,640,007 B2 | 12/2009 | Chen et al. |
| 7,660,126 B2 | 2/2010 | Cho et al. |
| 7,684,105 B2 | 3/2010 | Lamontagne et al. |
| 7,747,113 B2 | 6/2010 | Mukawa et al. |
| 7,761,390 B2 | 7/2010 | Ford |
| 7,773,111 B2 | 8/2010 | Cleveland et al. |
| 7,787,946 B2 | 8/2010 | Stahmann et al. |
| 7,805,386 B2 | 9/2010 | Greer |
| 7,809,435 B1 | 10/2010 | Ettare et al. |
| 7,844,310 B2 | 11/2010 | Anderson |
| D628,616 S | 12/2010 | Yuan |
| 7,850,306 B2 | 12/2010 | Uusitalo et al. |
| 7,870,211 B2 | 1/2011 | Pascal et al. |
| D633,939 S | 3/2011 | Puentes et al. |
| D634,771 S | 3/2011 | Fuchs |
| 7,901,368 B2 | 3/2011 | Flaherty et al. |
| 7,925,100 B2 | 4/2011 | Howell et al. |
| 7,948,763 B2 | 5/2011 | Chuang |
| D640,314 S | 6/2011 | Yang |
| D643,428 S | 8/2011 | Janky et al. |
| D646,192 S | 10/2011 | Woode |
| D649,177 S | 11/2011 | Cho et al. |
| 8,054,061 B2 | 11/2011 | Prance et al. |
| D654,622 S | 2/2012 | Hsu |
| 8,120,828 B2 | 2/2012 | Schwerdtner |
| 8,170,656 B2 | 5/2012 | Tan et al. |
| 8,179,604 B1 | 5/2012 | Prada Gomez et al. |
| 8,188,937 B1 | 5/2012 | Amafuji et al. |
| 8,190,249 B1 | 5/2012 | Gharieb et al. |
| D661,613 S | 6/2012 | Demeglio |
| 8,203,502 B1 | 6/2012 | Chi et al. |
| 8,207,473 B2 | 6/2012 | Axisa et al. |
| 8,212,859 B2 | 7/2012 | Tang et al. |
| D667,482 S | 9/2012 | Healy et al. |
| D669,522 S | 10/2012 | Klinar et al. |
| D669,523 S | 10/2012 | Wakata et al. |
| D671,590 S | 11/2012 | Klinar et al. |
| 8,311,623 B2 | 11/2012 | Sanger |
| 8,348,538 B2 | 1/2013 | Van Loenen et al. |
| 8,351,651 B2 | 1/2013 | Lee |
| 8,355,671 B2 | 1/2013 | Kramer et al. |
| 8,384,683 B2 | 2/2013 | Luo |
| 8,386,025 B2 | 2/2013 | Hoppe |
| 8,389,862 B2 | 3/2013 | Arora et al. |
| 8,421,634 B2 | 4/2013 | Tan et al. |
| 8,427,977 B2 | 4/2013 | Workman et al. |
| D682,343 S | 5/2013 | Waters |

(56) References Cited

U.S. PATENT DOCUMENTS

| | | |
|---|---|---|
| D682,727 S | 5/2013 | Bulgari |
| 8,435,191 B2 | 5/2013 | Barboutis et al. |
| 8,437,844 B2 | 5/2013 | Syed Momen et al. |
| 8,447,704 B2 | 5/2013 | Tan et al. |
| D685,019 S | 6/2013 | Li |
| 8,467,270 B2 | 6/2013 | Gossweiler, III et al. |
| 8,469,741 B2 | 6/2013 | Oster et al. |
| D687,087 S | 7/2013 | Iurilli |
| 8,484,022 B1 | 7/2013 | Vanhoucke |
| D689,862 S | 9/2013 | Liu |
| D692,941 S | 11/2013 | Klinar et al. |
| 8,591,411 B2 | 11/2013 | Banet et al. |
| D695,333 S | 12/2013 | Farnam et al. |
| D695,454 S | 12/2013 | Moore |
| 8,620,361 B2 | 12/2013 | Bailey et al. |
| 8,624,124 B2 | 1/2014 | Koo et al. |
| 8,634,119 B2 | 1/2014 | Bablumyan et al. |
| D701,555 S | 3/2014 | Markovitz et al. |
| 8,666,212 B1 | 3/2014 | Amirparviz |
| 8,702,629 B2 | 4/2014 | Giuffrida et al. |
| 8,704,882 B2 | 4/2014 | Turner |
| D704,248 S | 5/2014 | Dichiara |
| 8,718,980 B2 | 5/2014 | Garudadri et al. |
| 8,743,052 B1 | 6/2014 | Keller et al. |
| 8,744,543 B2 | 6/2014 | Li et al. |
| 8,754,862 B2 | 6/2014 | Zaliva |
| 8,777,668 B2 | 7/2014 | Ikeda et al. |
| D716,457 S | 10/2014 | Brefka et al. |
| D717,685 S | 11/2014 | Bailey et al. |
| 8,879,276 B2 | 11/2014 | Wang |
| 8,880,163 B2 | 11/2014 | Barachant et al. |
| 8,883,287 B2 | 11/2014 | Boyce et al. |
| 8,890,875 B2 | 11/2014 | Jammes et al. |
| 8,892,479 B2 | 11/2014 | Tan et al. |
| 8,895,865 B2 | 11/2014 | Lenahan et al. |
| D719,568 S | 12/2014 | Heinrich et al. |
| D719,570 S | 12/2014 | Heinrich et al. |
| 8,912,094 B2 | 12/2014 | Koo et al. |
| 8,914,472 B1 | 12/2014 | Lee et al. |
| 8,922,481 B1 | 12/2014 | Kauffmann et al. |
| D723,093 S | 2/2015 | Li |
| 8,954,135 B2 | 2/2015 | Yuen et al. |
| D724,647 S | 3/2015 | Rohrbach |
| 8,970,571 B1 | 3/2015 | Wong et al. |
| 8,971,023 B2 | 3/2015 | Olsson et al. |
| 9,018,532 B2 | 4/2015 | Wesselmann et al. |
| 9,037,530 B2 | 5/2015 | Tan et al. |
| 9,086,687 B2 | 7/2015 | Park et al. |
| 9,092,664 B2 | 7/2015 | Forutanpour et al. |
| D736,664 S | 8/2015 | Paradise et al. |
| 9,107,586 B2 | 8/2015 | Tran |
| D738,373 S | 9/2015 | Davies et al. |
| 9,135,708 B2 | 9/2015 | Ebisawa |
| 9,146,730 B2 | 9/2015 | Lazar |
| D741,855 S | 10/2015 | Park et al. |
| 9,170,674 B2 | 10/2015 | Forutanpour et al. |
| D742,272 S | 11/2015 | Bailey et al. |
| D742,874 S | 11/2015 | Cheng et al. |
| D743,963 S | 11/2015 | Osterhout |
| 9,182,826 B2 | 11/2015 | Powledge et al. |
| 9,211,417 B2 | 12/2015 | Heldman et al. |
| 9,218,574 B2 | 12/2015 | Phillipps et al. |
| D747,714 S | 1/2016 | Erbeus |
| D747,759 S | 1/2016 | Ho |
| 9,235,934 B2 | 1/2016 | Mandella et al. |
| 9,240,069 B1 | 1/2016 | Li |
| D750,623 S | 3/2016 | Park et al. |
| D751,065 S | 3/2016 | Magi |
| 9,278,453 B2 | 3/2016 | Assad |
| 9,299,248 B2 | 3/2016 | Lake et al. |
| D756,359 S | 5/2016 | Bailey et al. |
| 9,329,694 B2 | 5/2016 | Slonneger |
| 9,341,659 B2 | 5/2016 | Poupyrev et al. |
| 9,349,280 B2 | 5/2016 | Baldwin et al. |
| 9,351,653 B1 | 5/2016 | Harrison |
| D758,476 S | 6/2016 | Ho |
| D760,313 S | 6/2016 | Ho et al. |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,393,418 B2 | 7/2016 | Giuffrida et al. |
| 9,402,582 B1 | 8/2016 | Parviz et al. |
| 9,408,316 B2 | 8/2016 | Bailey et al. |
| 9,418,927 B2 | 8/2016 | Axisa et al. |
| D766,895 S | 9/2016 | Choi |
| 9,439,566 B2 | 9/2016 | Arne et al. |
| D768,627 S | 10/2016 | Rochat et al. |
| 9,459,697 B2 | 10/2016 | Bedikian et al. |
| 9,472,956 B2 | 10/2016 | Michaelis et al. |
| 9,477,313 B2 | 10/2016 | Mistry et al. |
| D771,735 S | 11/2016 | Lee et al. |
| 9,483,123 B2 | 11/2016 | Aleem et al. |
| 9,529,434 B2 | 12/2016 | Choi et al. |
| D780,828 S | 3/2017 | Bonaventura et al. |
| D780,829 S | 3/2017 | Bonaventura et al. |
| 9,597,015 B2 | 3/2017 | McNames et al. |
| 9,600,030 B2 | 3/2017 | Bailey et al. |
| 9,612,661 B2 | 4/2017 | Wagner et al. |
| 9,613,262 B2 | 4/2017 | Holz |
| 9,652,047 B2 | 5/2017 | Mullins et al. |
| 9,654,477 B1 | 5/2017 | Kotamraju |
| 9,659,403 B1 | 5/2017 | Horowitz |
| 9,687,168 B2 | 6/2017 | John |
| 9,696,795 B2 | 7/2017 | Marcolina et al. |
| 9,720,515 B2 | 8/2017 | Wagner et al. |
| 9,741,169 B1 | 8/2017 | Holz |
| 9,766,709 B2 | 9/2017 | Holz |
| 9,785,247 B1 | 10/2017 | Horowitz et al. |
| 9,788,789 B2 | 10/2017 | Bailey |
| 9,807,221 B2 | 10/2017 | Bailey et al. |
| 9,864,431 B2 | 1/2018 | Keskin et al. |
| 9,867,548 B2 | 1/2018 | Le et al. |
| 9,880,632 B2 | 1/2018 | Ataee et al. |
| 9,891,718 B2 | 2/2018 | Connor |
| 9,921,641 B1 | 3/2018 | Worley, III et al. |
| 10,042,422 B2 | 8/2018 | Morun et al. |
| 10,070,799 B2 | 9/2018 | Ang et al. |
| 10,078,435 B2 | 9/2018 | Noel |
| 10,101,809 B2 | 10/2018 | Morun et al. |
| 10,152,082 B2 | 12/2018 | Bailey |
| 10,185,416 B2 | 1/2019 | Mistry et al. |
| 10,188,309 B2 | 1/2019 | Morun et al. |
| 10,199,008 B2 | 2/2019 | Aleem et al. |
| 10,203,751 B2 | 2/2019 | Keskin et al. |
| 10,216,274 B2 | 2/2019 | Chapeskie et al. |
| 10,251,577 B2 | 4/2019 | Morun et al. |
| 10,310,601 B2 | 6/2019 | Morun et al. |
| 10,331,210 B2 | 6/2019 | Morun et al. |
| 10,362,958 B2 | 7/2019 | Morun et al. |
| 10,409,371 B2 | 9/2019 | Kaifosh et al. |
| 10,429,928 B2 | 10/2019 | Morun et al. |
| 10,437,335 B2 | 10/2019 | Daniels |
| 10,460,455 B2 | 10/2019 | Giurgica-Tiron et al. |
| 10,489,986 B2 | 11/2019 | Kaifosh et al. |
| 10,496,168 B2 | 12/2019 | Kaifosh et al. |
| 10,504,286 B2 | 12/2019 | Kaifosh et al. |
| 10,520,378 B1 | 12/2019 | Brown et al. |
| 10,528,135 B2 | 1/2020 | Bailey et al. |
| 10,558,273 B2 | 2/2020 | Park et al. |
| 10,592,001 B2 | 3/2020 | Berenzweig et al. |
| 10,610,737 B1 | 4/2020 | Crawford |
| 10,676,083 B1 | 6/2020 | De Sapio et al. |
| 10,687,759 B2 | 6/2020 | Guo et al. |
| 10,905,350 B2 | 2/2021 | Berenzweig et al. |
| 10,905,383 B2 | 2/2021 | Barachant |
| 10,937,414 B2 | 3/2021 | Berenzweig et al. |
| 10,990,174 B2 | 4/2021 | Kaifosh et al. |
| 11,009,951 B2 | 5/2021 | Bailey et al. |
| 11,150,730 B1 | 10/2021 | Anderson et al. |
| 2001/0033402 A1 | 10/2001 | Popovich |
| 2002/0003627 A1 | 1/2002 | Rieder |
| 2002/0009972 A1 | 1/2002 | Amento et al. |
| 2002/0030636 A1 | 3/2002 | Richards |
| 2002/0032386 A1 | 3/2002 | Sackner et al. |

(56) References Cited

U.S. PATENT DOCUMENTS

| | | |
|---|---|---|
| 2002/0077534 A1 | 6/2002 | DuRousseau |
| 2002/0094701 A1 | 7/2002 | Biegelsen et al. |
| 2002/0120415 A1 | 8/2002 | Millott et al. |
| 2002/0120916 A1 | 8/2002 | Snider, Jr. |
| 2002/0198472 A1 | 12/2002 | Kramer |
| 2003/0030595 A1 | 2/2003 | Radley-Smith |
| 2003/0036691 A1 | 2/2003 | Stanaland et al. |
| 2003/0051505 A1 | 3/2003 | Robertson et al. |
| 2003/0144586 A1 | 7/2003 | Tsubata |
| 2003/0144829 A1 | 7/2003 | Geatz et al. |
| 2003/0171921 A1 | 9/2003 | Manabe et al. |
| 2003/0182630 A1 | 9/2003 | Saund et al. |
| 2003/0184544 A1 | 10/2003 | Prudent |
| 2004/0010210 A1 | 1/2004 | Avinash et al. |
| 2004/0024312 A1 | 2/2004 | Zheng |
| 2004/0054273 A1 | 3/2004 | Finneran et al. |
| 2004/0068409 A1 | 4/2004 | Tanaka et al. |
| 2004/0073104 A1 | 4/2004 | Brun Del Re et al. |
| 2004/0080499 A1 | 4/2004 | Lui |
| 2004/0092839 A1 | 5/2004 | Shin et al. |
| 2004/0194500 A1 | 10/2004 | Rapport |
| 2004/0210165 A1 | 10/2004 | Marmaropoulos et al. |
| 2004/0243342 A1 | 12/2004 | Rekimoto |
| 2004/0254617 A1 | 12/2004 | Hemmerling et al. |
| 2005/0005637 A1 | 1/2005 | Rapport |
| 2005/0012715 A1 | 1/2005 | Ford |
| 2005/0070227 A1 | 3/2005 | Shen et al. |
| 2005/0070791 A1 | 3/2005 | Edney et al. |
| 2005/0115561 A1 | 6/2005 | Stahmann et al. |
| 2005/0119701 A1 | 6/2005 | Lauter et al. |
| 2005/0177038 A1 | 8/2005 | Kolpin et al. |
| 2005/0179644 A1 | 8/2005 | Alsio et al. |
| 2006/0018833 A1 | 1/2006 | Murphy et al. |
| 2006/0037359 A1 | 2/2006 | Stinespring |
| 2006/0058699 A1 | 3/2006 | Vitiello et al. |
| 2006/0061544 A1 | 3/2006 | Min et al. |
| 2006/0121958 A1 | 6/2006 | Jung et al. |
| 2006/0129057 A1 | 6/2006 | Maekawa et al. |
| 2006/0132705 A1 | 6/2006 | Li |
| 2006/0149338 A1 | 7/2006 | Flaherty et al. |
| 2006/0211956 A1 | 9/2006 | Sankai |
| 2006/0238707 A1 | 10/2006 | Elvesjo et al. |
| 2007/0009151 A1 | 1/2007 | Pittman et al. |
| 2007/0016265 A1 | 1/2007 | Davoodi et al. |
| 2007/0023662 A1 | 2/2007 | Brady et al. |
| 2007/0078308 A1 | 4/2007 | Daly |
| 2007/0132785 A1 | 6/2007 | Ebersole, Jr. et al. |
| 2007/0148624 A1 | 6/2007 | Nativ |
| 2007/0172797 A1 | 7/2007 | Hada et al. |
| 2007/0177770 A1 | 8/2007 | Derchak et al. |
| 2007/0185697 A1 | 8/2007 | Tan et al. |
| 2007/0256494 A1 | 11/2007 | Nakamura et al. |
| 2007/0276270 A1 | 11/2007 | Tran |
| 2007/0279852 A1 | 12/2007 | Daniel et al. |
| 2007/0285399 A1 | 12/2007 | Lund |
| 2008/0001735 A1 | 1/2008 | Tran |
| 2008/0032638 A1 | 2/2008 | Anderson |
| 2008/0051673 A1 | 2/2008 | Kong et al. |
| 2008/0052643 A1 | 2/2008 | Ike et al. |
| 2008/0058668 A1 | 3/2008 | Seyed Momen et al. |
| 2008/0103639 A1 | 5/2008 | Troy et al. |
| 2008/0103769 A1 | 5/2008 | Schultz et al. |
| 2008/0136775 A1 | 6/2008 | Conant |
| 2008/0152217 A1 | 6/2008 | Greer |
| 2008/0163130 A1 | 7/2008 | Westerman |
| 2008/0214360 A1 | 9/2008 | Stirling et al. |
| 2008/0221487 A1 | 9/2008 | Zohar et al. |
| 2008/0262772 A1 | 10/2008 | Luinge et al. |
| 2008/0278497 A1 | 11/2008 | Jammes et al. |
| 2008/0285805 A1 | 11/2008 | Luinge et al. |
| 2009/0005700 A1 | 1/2009 | Joshi et al. |
| 2009/0007597 A1 | 1/2009 | Hanevold |
| 2009/0027337 A1 | 1/2009 | Hildreth |
| 2009/0031757 A1 | 2/2009 | Harding |
| 2009/0040016 A1 | 2/2009 | Ikeda |
| 2009/0051544 A1 | 2/2009 | Niknejad |
| 2009/0079607 A1 | 3/2009 | Denison et al. |
| 2009/0079813 A1 | 3/2009 | Hildreth |
| 2009/0082692 A1 | 3/2009 | Hale et al. |
| 2009/0082701 A1 | 3/2009 | Zohar et al. |
| 2009/0085864 A1 | 4/2009 | Kutliroff et al. |
| 2009/0102580 A1 | 4/2009 | Uchaykin |
| 2009/0109241 A1 | 4/2009 | Tsujimoto |
| 2009/0112080 A1 | 4/2009 | Matthews |
| 2009/0124881 A1 | 5/2009 | Rytky |
| 2009/0147004 A1 | 6/2009 | Ramon et al. |
| 2009/0179824 A1 | 7/2009 | Tsujimoto et al. |
| 2009/0189864 A1 | 7/2009 | Walker et al. |
| 2009/0189867 A1 | 7/2009 | Krah et al. |
| 2009/0195497 A1 | 8/2009 | Fitzgerald et al. |
| 2009/0204031 A1 | 8/2009 | Mcnames et al. |
| 2009/0207464 A1 | 8/2009 | Wiltshire et al. |
| 2009/0209878 A1 | 8/2009 | Sanger |
| 2009/0251407 A1 | 10/2009 | Flake et al. |
| 2009/0258669 A1 | 10/2009 | Nie et al. |
| 2009/0265671 A1 | 10/2009 | Sachs et al. |
| 2009/0318785 A1 | 12/2009 | Ishikawa et al. |
| 2009/0319230 A1 | 12/2009 | Case, Jr. et al. |
| 2009/0322653 A1 | 12/2009 | Putilin et al. |
| 2009/0326406 A1 | 12/2009 | Tan et al. |
| 2009/0327171 A1 | 12/2009 | Tan et al. |
| 2010/0030532 A1 | 2/2010 | Arora et al. |
| 2010/0041974 A1 | 2/2010 | Ting et al. |
| 2010/0063794 A1 | 3/2010 | Hernandez-Rebollar |
| 2010/0066664 A1 | 3/2010 | Son et al. |
| 2010/0106044 A1 | 4/2010 | Linderman |
| 2010/0113910 A1 | 5/2010 | Brauers et al. |
| 2010/0142015 A1 | 6/2010 | Kuwahara et al. |
| 2010/0149073 A1 | 6/2010 | Chaum et al. |
| 2010/0150415 A1 | 6/2010 | Atkinson et al. |
| 2010/0228487 A1 | 9/2010 | Leuthardt et al. |
| 2010/0234696 A1 | 9/2010 | Li et al. |
| 2010/0240981 A1 | 9/2010 | Barboutis et al. |
| 2010/0249635 A1 | 9/2010 | Van Der Reijden |
| 2010/0280628 A1 | 11/2010 | Sankai |
| 2010/0292595 A1 | 11/2010 | Paul |
| 2010/0292606 A1 | 11/2010 | Prakash et al. |
| 2010/0292617 A1 | 11/2010 | Lei et al. |
| 2010/0293115 A1 | 11/2010 | Seyed Momen |
| 2010/0306713 A1 | 12/2010 | Geisner et al. |
| 2010/0315266 A1 | 12/2010 | Gunawardana et al. |
| 2010/0317958 A1 | 12/2010 | Beck et al. |
| 2011/0007035 A1 | 1/2011 | Shai |
| 2011/0018754 A1 | 1/2011 | Tojima et al. |
| 2011/0025982 A1 | 2/2011 | Takahashi |
| 2011/0054360 A1 | 3/2011 | Son et al. |
| 2011/0065319 A1 | 3/2011 | Oster et al. |
| 2011/0066381 A1 | 3/2011 | Garudadri et al. |
| 2011/0072510 A1 | 3/2011 | Cheswick |
| 2011/0077484 A1 | 3/2011 | Van Slyke et al. |
| 2011/0082838 A1 | 4/2011 | Niemela |
| 2011/0092826 A1 | 4/2011 | Lee et al. |
| 2011/0119216 A1 | 5/2011 | Wigdor |
| 2011/0133934 A1 | 6/2011 | Tan et al. |
| 2011/0134026 A1 | 6/2011 | Kang et al. |
| 2011/0151974 A1 | 6/2011 | Deaguero |
| 2011/0166434 A1 | 7/2011 | Gargiulo |
| 2011/0172503 A1 | 7/2011 | Knepper et al. |
| 2011/0173204 A1 | 7/2011 | Murillo et al. |
| 2011/0173574 A1 | 7/2011 | Clavin et al. |
| 2011/0181527 A1 | 7/2011 | Capela et al. |
| 2011/0205242 A1 | 8/2011 | Friesen |
| 2011/0213278 A1 | 9/2011 | Horak et al. |
| 2011/0221672 A1 | 9/2011 | Osterhout et al. |
| 2011/0224507 A1 | 9/2011 | Banet et al. |
| 2011/0224556 A1 | 9/2011 | Moon et al. |
| 2011/0224564 A1 | 9/2011 | Moon et al. |
| 2011/0230782 A1 | 9/2011 | Bartol et al. |
| 2011/0248914 A1 | 10/2011 | Sherr |
| 2011/0262002 A1 | 10/2011 | Lee |
| 2011/0270135 A1 | 11/2011 | Dooley et al. |
| 2011/0295100 A1 | 12/2011 | Hegde et al. |
| 2011/0313762 A1 | 12/2011 | Ben-David et al. |
| 2012/0002256 A1 | 1/2012 | Lacoste et al. |

(56) References Cited

U.S. PATENT DOCUMENTS

| | | |
|---|---|---|
| 2012/0007821 A1 | 1/2012 | Zaliva |
| 2012/0029322 A1 | 2/2012 | Wartena et al. |
| 2012/0051005 A1 | 3/2012 | Vanfleteren et al. |
| 2012/0052268 A1 | 3/2012 | Axisa et al. |
| 2012/0053439 A1 | 3/2012 | Ylostalo et al. |
| 2012/0066163 A1 | 3/2012 | Balls et al. |
| 2012/0071092 A1 | 3/2012 | Pasquero et al. |
| 2012/0071780 A1 | 3/2012 | Barachant |
| 2012/0101357 A1 | 4/2012 | Hoskuldsson et al. |
| 2012/0117514 A1 | 5/2012 | Kim et al. |
| 2012/0139817 A1 | 6/2012 | Freeman |
| 2012/0157789 A1 | 6/2012 | Kangas et al. |
| 2012/0157886 A1 | 6/2012 | Tenn et al. |
| 2012/0165695 A1 | 6/2012 | Kidmose et al. |
| 2012/0182309 A1 | 7/2012 | Griffin et al. |
| 2012/0184838 A1 | 7/2012 | John et al. |
| 2012/0188158 A1 | 7/2012 | Tan et al. |
| 2012/0203076 A1 | 8/2012 | Fatta et al. |
| 2012/0209134 A1 | 8/2012 | Morita et al. |
| 2012/0226130 A1 | 9/2012 | De Graff et al. |
| 2012/0249797 A1 | 10/2012 | Haddick et al. |
| 2012/0265090 A1 | 10/2012 | Fink et al. |
| 2012/0265480 A1 | 10/2012 | Oshima |
| 2012/0275621 A1 | 11/2012 | Elko |
| 2012/0283526 A1 | 11/2012 | Gommesen et al. |
| 2012/0283896 A1 | 11/2012 | Persaud et al. |
| 2012/0293548 A1 | 11/2012 | Perez et al. |
| 2012/0302858 A1 | 11/2012 | Kidmose et al. |
| 2012/0320532 A1 | 12/2012 | Wang |
| 2012/0323521 A1 | 12/2012 | De Foras et al. |
| 2013/0004033 A1 | 1/2013 | Trugenberger |
| 2013/0005303 A1 | 1/2013 | Song et al. |
| 2013/0016292 A1 | 1/2013 | Miao et al. |
| 2013/0016413 A1 | 1/2013 | Saeedi et al. |
| 2013/0020948 A1 | 1/2013 | Han et al. |
| 2013/0027341 A1 | 1/2013 | Mastandrea |
| 2013/0038707 A1 | 2/2013 | Cunningham et al. |
| 2013/0077820 A1 | 3/2013 | Marais et al. |
| 2013/0080794 A1 | 3/2013 | Hsieh |
| 2013/0106686 A1 | 5/2013 | Bennett |
| 2013/0123656 A1 | 5/2013 | Heck |
| 2013/0123666 A1 | 5/2013 | Giuffrida et al. |
| 2013/0127708 A1 | 5/2013 | Jung et al. |
| 2013/0131538 A1 | 5/2013 | Gaw et al. |
| 2013/0135223 A1 | 5/2013 | Shai |
| 2013/0135722 A1 | 5/2013 | Yokoyama |
| 2013/0141375 A1 | 6/2013 | Ludwig et al. |
| 2013/0144629 A1 | 6/2013 | Johnston et al. |
| 2013/0165813 A1 | 6/2013 | Chang et al. |
| 2013/0191741 A1 | 7/2013 | Dickinson et al. |
| 2013/0198694 A1 | 8/2013 | Rahman et al. |
| 2013/0207889 A1 | 8/2013 | Chang et al. |
| 2013/0215235 A1 | 8/2013 | Russell |
| 2013/0217998 A1 | 8/2013 | Mahfouz et al. |
| 2013/0221996 A1 | 8/2013 | Poupyrev et al. |
| 2013/0222384 A1 | 8/2013 | Futterer |
| 2013/0232095 A1 | 9/2013 | Tan et al. |
| 2013/0259238 A1 | 10/2013 | Xiang et al. |
| 2013/0265229 A1 | 10/2013 | Forutanpour et al. |
| 2013/0265437 A1 | 10/2013 | Thorn et al. |
| 2013/0271292 A1 | 10/2013 | McDermott |
| 2013/0285901 A1 | 10/2013 | Lee et al. |
| 2013/0285913 A1 | 10/2013 | Griffin et al. |
| 2013/0293580 A1 | 11/2013 | Spivack |
| 2013/0310979 A1 | 11/2013 | Herr et al. |
| 2013/0312256 A1 | 11/2013 | Wesselmann et al. |
| 2013/0317382 A1 | 11/2013 | Le et al. |
| 2013/0317648 A1 | 11/2013 | Assad |
| 2013/0332196 A1 | 12/2013 | Pinsker |
| 2013/0335302 A1 | 12/2013 | Crane et al. |
| 2014/0005743 A1 | 1/2014 | Giuffrida et al. |
| 2014/0020945 A1 | 1/2014 | Hurwitz et al. |
| 2014/0028539 A1 | 1/2014 | Newham et al. |
| 2014/0028546 A1 | 1/2014 | Jeon et al. |
| 2014/0045547 A1 | 2/2014 | Singamsetty et al. |
| 2014/0049417 A1 | 2/2014 | Abdurrahman et al. |
| 2014/0051946 A1 | 2/2014 | Arne et al. |
| 2014/0052150 A1 | 2/2014 | Taylor et al. |
| 2014/0074179 A1 | 3/2014 | Heldman et al. |
| 2014/0092009 A1 | 4/2014 | Yen et al. |
| 2014/0094675 A1 | 4/2014 | Luna et al. |
| 2014/0098018 A1 | 4/2014 | Kim et al. |
| 2014/0100432 A1 | 4/2014 | Golda et al. |
| 2014/0107493 A1 | 4/2014 | Yuen et al. |
| 2014/0121471 A1 | 5/2014 | Walker |
| 2014/0122958 A1 | 5/2014 | Greenebrg et al. |
| 2014/0132512 A1 | 5/2014 | Gomez Sainz-Garcia |
| 2014/0139422 A1 | 5/2014 | Mistry et al. |
| 2014/0142937 A1 | 5/2014 | Powledge et al. |
| 2014/0143064 A1 | 5/2014 | Tran |
| 2014/0147820 A1 | 5/2014 | Snow et al. |
| 2014/0157168 A1 | 6/2014 | Albouyeh et al. |
| 2014/0194062 A1 | 7/2014 | Palin et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0198944 A1 | 7/2014 | Forutanpour et al. |
| 2014/0200432 A1 | 7/2014 | Banerji et al. |
| 2014/0201666 A1 | 7/2014 | Bedikian et al. |
| 2014/0202643 A1 | 7/2014 | Hikmet et al. |
| 2014/0204455 A1 | 7/2014 | Popovich et al. |
| 2014/0223462 A1 | 8/2014 | Aimone et al. |
| 2014/0226193 A1 | 8/2014 | Sun |
| 2014/0232651 A1 | 8/2014 | Kress et al. |
| 2014/0236031 A1 | 8/2014 | Banet et al. |
| 2014/0240103 A1 | 8/2014 | Lake et al. |
| 2014/0240223 A1 | 8/2014 | Lake et al. |
| 2014/0245200 A1 | 8/2014 | Holz |
| 2014/0249397 A1* | 9/2014 | Lake ............... A61B 5/296 600/386 |
| 2014/0257141 A1 | 9/2014 | Giuffrida et al. |
| 2014/0258864 A1 | 9/2014 | Shenoy et al. |
| 2014/0277622 A1 | 9/2014 | Raniere |
| 2014/0278139 A1 | 9/2014 | Hong et al. |
| 2014/0278441 A1 | 9/2014 | Ton et al. |
| 2014/0279860 A1 | 9/2014 | Pan et al. |
| 2014/0282282 A1 | 9/2014 | Holz |
| 2014/0285326 A1 | 9/2014 | Luna et al. |
| 2014/0285429 A1 | 9/2014 | Simmons |
| 2014/0297528 A1 | 10/2014 | Agrawal et al. |
| 2014/0299362 A1 | 10/2014 | Park et al. |
| 2014/0304665 A1 | 10/2014 | Holz |
| 2014/0310595 A1 | 10/2014 | Acharya et al. |
| 2014/0330404 A1 | 11/2014 | Abdelghani et al. |
| 2014/0334083 A1 | 11/2014 | Bailey |
| 2014/0334653 A1 | 11/2014 | Luna et al. |
| 2014/0337861 A1 | 11/2014 | Chang et al. |
| 2014/0340857 A1 | 11/2014 | Hsu et al. |
| 2014/0344731 A1 | 11/2014 | Holz |
| 2014/0349257 A1 | 11/2014 | Connor |
| 2014/0354528 A1 | 12/2014 | Laughlin et al. |
| 2014/0354529 A1 | 12/2014 | Laughlin et al. |
| 2014/0355825 A1 | 12/2014 | Kim et al. |
| 2014/0358024 A1 | 12/2014 | Nelson et al. |
| 2014/0358825 A1 | 12/2014 | Phillipps |
| 2014/0359540 A1 | 12/2014 | Kelsey et al. |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0368424 A1 | 12/2014 | Choi et al. |
| 2014/0368428 A1 | 12/2014 | Pinault |
| 2014/0368474 A1 | 12/2014 | Kim et al. |
| 2014/0368896 A1 | 12/2014 | Nakazono et al. |
| 2014/0375465 A1 | 12/2014 | Fenuccio et al. |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0011857 A1 | 1/2015 | Henson et al. |
| 2015/0019135 A1 | 1/2015 | Kacyvenski |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0036221 A1 | 2/2015 | Stephenson |
| 2015/0045689 A1 | 2/2015 | Barone |

(56) References Cited

U.S. PATENT DOCUMENTS

| | | |
|---|---|---|
| 2015/0045699 A1 | 2/2015 | Mokaya et al. |
| 2015/0051470 A1 | 2/2015 | Bailey et al. |
| 2015/0057506 A1 | 2/2015 | Luna et al. |
| 2015/0057770 A1 | 2/2015 | Bailey et al. |
| 2015/0065840 A1 | 3/2015 | Bailey et al. |
| 2015/0070270 A1 | 3/2015 | Bailey et al. |
| 2015/0070274 A1 | 3/2015 | Morozov |
| 2015/0072326 A1 | 3/2015 | Mauri et al. |
| 2015/0084860 A1 | 3/2015 | Aleem et al. |
| 2015/0091790 A1 | 4/2015 | Forutanpour et al. |
| 2015/0094564 A1 | 4/2015 | Tashman et al. |
| 2015/0099946 A1 | 4/2015 | Sahin |
| 2015/0106052 A1 | 4/2015 | Balakrishnan et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0148728 A1 | 5/2015 | Sallum et al. |
| 2015/0157944 A1 | 6/2015 | Gottlieb |
| 2015/0160621 A1 | 6/2015 | Yilmaz |
| 2015/0169074 A1 | 6/2015 | Ataee et al. |
| 2015/0170421 A1 | 6/2015 | Mandella et al. |
| 2015/0177841 A1 | 6/2015 | Vanblon et al. |
| 2015/0182113 A1 | 7/2015 | Utter, II |
| 2015/0182130 A1 | 7/2015 | Utter, II |
| 2015/0182160 A1 | 7/2015 | Kim et al. |
| 2015/0182163 A1 | 7/2015 | Utter |
| 2015/0182164 A1 | 7/2015 | Utter, II |
| 2015/0182165 A1 | 7/2015 | Miller et al. |
| 2015/0185838 A1 | 7/2015 | Camacho-Perez et al. |
| 2015/0185853 A1 | 7/2015 | Clausen et al. |
| 2015/0186609 A1 | 7/2015 | Utter, II |
| 2015/0187355 A1 | 7/2015 | Parkinson et al. |
| 2015/0193949 A1 | 7/2015 | Katz et al. |
| 2015/0199025 A1 | 7/2015 | Holz |
| 2015/0205126 A1 | 7/2015 | Schowengerdt |
| 2015/0205134 A1 | 7/2015 | Bailey et al. |
| 2015/0213191 A1 | 7/2015 | Abdelghani et al. |
| 2015/0216475 A1 | 8/2015 | Luna et al. |
| 2015/0220152 A1 | 8/2015 | Tait et al. |
| 2015/0223716 A1 | 8/2015 | Korkala et al. |
| 2015/0230756 A1 | 8/2015 | Luna et al. |
| 2015/0234426 A1 | 8/2015 | Bailey et al. |
| 2015/0237716 A1 | 8/2015 | Su et al. |
| 2015/0242009 A1 | 8/2015 | Xiao et al. |
| 2015/0242120 A1 | 8/2015 | Rodriguez |
| 2015/0242575 A1 | 8/2015 | Abovitz et al. |
| 2015/0261306 A1 | 9/2015 | Lake |
| 2015/0261318 A1 | 9/2015 | Scavezze et al. |
| 2015/0272483 A1 | 10/2015 | Etemad et al. |
| 2015/0277575 A1 | 10/2015 | Ataee et al. |
| 2015/0288944 A1 | 10/2015 | Nistico et al. |
| 2015/0289995 A1 | 10/2015 | Wilkinson et al. |
| 2015/0296553 A1 | 10/2015 | DiFranco et al. |
| 2015/0302168 A1 | 10/2015 | De Sapio et al. |
| 2015/0305672 A1 | 10/2015 | Grey et al. |
| 2015/0309563 A1 | 10/2015 | Connor |
| 2015/0309582 A1 | 10/2015 | Gupta |
| 2015/0310766 A1 | 10/2015 | Alshehri et al. |
| 2015/0312175 A1 | 10/2015 | Langholz |
| 2015/0313496 A1 | 11/2015 | Connor |
| 2015/0323998 A1 | 11/2015 | Kudekar et al. |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0351690 A1 | 12/2015 | Toth et al. |
| 2015/0355716 A1 | 12/2015 | Balasubramanian et al. |
| 2015/0355718 A1 | 12/2015 | Slonneger |
| 2015/0362734 A1 | 12/2015 | Moser et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2015/0378161 A1 | 12/2015 | Bailey et al. |
| 2015/0378162 A1 | 12/2015 | Bailey et al. |
| 2015/0378164 A1 | 12/2015 | Bailey et al. |
| 2015/0379770 A1 | 12/2015 | Haley, Jr. et al. |
| 2016/0011668 A1 | 1/2016 | Gilad-Bachrach et al. |
| 2016/0020500 A1 | 1/2016 | Matsuda |
| 2016/0026853 A1 | 1/2016 | Wexler et al. |
| 2016/0033771 A1 | 2/2016 | Tremblay et al. |
| 2016/0049073 A1 | 2/2016 | Lee |
| 2016/0050037 A1 | 2/2016 | Webb |
| 2016/0071319 A1 | 3/2016 | Fallon et al. |
| 2016/0092504 A1 | 3/2016 | Mitri et al. |
| 2016/0099010 A1 | 4/2016 | Sainath et al. |
| 2016/0107309 A1 | 4/2016 | Walsh et al. |
| 2016/0113587 A1 | 4/2016 | Kothe et al. |
| 2016/0144172 A1 | 5/2016 | Hsueh et al. |
| 2016/0150636 A1 | 5/2016 | Otsubo |
| 2016/0156762 A1 | 6/2016 | Bailey et al. |
| 2016/0162604 A1 | 6/2016 | Xiaoli et al. |
| 2016/0170710 A1 | 6/2016 | Kim et al. |
| 2016/0187992 A1 | 6/2016 | Yamamoto et al. |
| 2016/0195928 A1 | 7/2016 | Wagner et al. |
| 2016/0199699 A1 | 7/2016 | Klassen |
| 2016/0202081 A1 | 7/2016 | Debieuvre et al. |
| 2016/0206206 A1 | 7/2016 | Avila et al. |
| 2016/0207201 A1 | 7/2016 | Herr et al. |
| 2016/0217614 A1 | 7/2016 | Kraver et al. |
| 2016/0235323 A1 | 8/2016 | Tadi et al. |
| 2016/0238845 A1 | 8/2016 | Alexander et al. |
| 2016/0239080 A1 | 8/2016 | Marcolina et al. |
| 2016/0242646 A1 | 8/2016 | Obma |
| 2016/0259407 A1 | 9/2016 | Schick |
| 2016/0262687 A1 | 9/2016 | Vaidyanathan et al. |
| 2016/0263458 A1 | 9/2016 | Mather et al. |
| 2016/0274365 A1 | 9/2016 | Bailey et al. |
| 2016/0274732 A1 | 9/2016 | Bang et al. |
| 2016/0274758 A1* | 9/2016 | Bailey .................... G06F 1/163 |
| 2016/0275726 A1 | 9/2016 | Mullins |
| 2016/0282947 A1 | 9/2016 | Schwarz et al. |
| 2016/0291768 A1 | 10/2016 | Cho et al. |
| 2016/0292497 A1 | 10/2016 | Kehtarnavaz et al. |
| 2016/0309249 A1 | 10/2016 | Wu et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0314623 A1 | 10/2016 | Coleman et al. |
| 2016/0327796 A1 | 11/2016 | Bailey et al. |
| 2016/0327797 A1 | 11/2016 | Bailey et al. |
| 2016/0342227 A1 | 11/2016 | Natzke et al. |
| 2016/0349514 A1 | 12/2016 | Alexander et al. |
| 2016/0349515 A1 | 12/2016 | Alexander et al. |
| 2016/0349516 A1 | 12/2016 | Alexander et al. |
| 2016/0350973 A1 | 12/2016 | Shapira et al. |
| 2016/0377865 A1 | 12/2016 | Alexander et al. |
| 2016/0377866 A1 | 12/2016 | Alexander et al. |
| 2017/0025026 A1 | 1/2017 | Ortiz Catalan |
| 2017/0031502 A1 | 2/2017 | Rosenberg et al. |
| 2017/0035313 A1 | 2/2017 | Hong et al. |
| 2017/0061817 A1 | 3/2017 | Mettler |
| 2017/0068095 A1 | 3/2017 | Holland et al. |
| 2017/0068445 A1 | 3/2017 | Lee et al. |
| 2017/0075426 A1 | 3/2017 | Camacho Perez et al. |
| 2017/0079828 A1 | 3/2017 | Pedtke et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0095178 A1 | 4/2017 | Schoen et al. |
| 2017/0097753 A1 | 4/2017 | Bailey et al. |
| 2017/0115483 A1 | 4/2017 | Aleem et al. |
| 2017/0119472 A1 | 5/2017 | Herrmann et al. |
| 2017/0123487 A1 | 5/2017 | Hazra et al. |
| 2017/0124474 A1 | 5/2017 | Kashyap |
| 2017/0124816 A1 | 5/2017 | Yang et al. |
| 2017/0127354 A1 | 5/2017 | Garland et al. |
| 2017/0147077 A1 | 5/2017 | Park et al. |
| 2017/0153701 A1 | 6/2017 | Mahon et al. |
| 2017/0161635 A1 | 6/2017 | Oono et al. |
| 2017/0188878 A1 | 7/2017 | Lee |
| 2017/0188980 A1 | 7/2017 | Ash |
| 2017/0197142 A1 | 7/2017 | Stafford et al. |

(56) References Cited

U.S. PATENT DOCUMENTS

| | | |
|---|---|---|
| 2017/0205876 A1 | 7/2017 | Vidal et al. |
| 2017/0209055 A1 | 7/2017 | Pantelopoulos et al. |
| 2017/0212290 A1 | 7/2017 | Alexander et al. |
| 2017/0212349 A1 | 7/2017 | Bailey et al. |
| 2017/0219829 A1 | 8/2017 | Bailey |
| 2017/0220923 A1 | 8/2017 | Bae et al. |
| 2017/0237789 A1 | 8/2017 | Harner et al. |
| 2017/0237901 A1 | 8/2017 | Lee et al. |
| 2017/0259167 A1 | 9/2017 | Cook et al. |
| 2017/0262064 A1 | 9/2017 | Ofir et al. |
| 2017/0277282 A1 | 9/2017 | Go |
| 2017/0285744 A1 | 10/2017 | Juliato |
| 2017/0285756 A1 | 10/2017 | Wang et al. |
| 2017/0285757 A1 | 10/2017 | Robertson et al. |
| 2017/0285848 A1 | 10/2017 | Rosenberg et al. |
| 2017/0296363 A1 | 10/2017 | Yetkin et al. |
| 2017/0299956 A1 | 10/2017 | Holland et al. |
| 2017/0301630 A1 | 10/2017 | Nguyen et al. |
| 2017/0308118 A1 | 10/2017 | Ito |
| 2017/0312614 A1 | 11/2017 | Tran et al. |
| 2017/0329392 A1 | 11/2017 | Keskin et al. |
| 2017/0329404 A1 | 11/2017 | Keskin et al. |
| 2017/0340506 A1 | 11/2017 | Zhang et al. |
| 2017/0344706 A1 | 11/2017 | Torres et al. |
| 2017/0347908 A1 | 12/2017 | Watanabe et al. |
| 2017/0371403 A1* | 12/2017 | Wetzler .................. G06F 3/01 |
| 2018/0000367 A1 | 1/2018 | Longinotti-Buitoni |
| 2018/0018825 A1 | 1/2018 | Kim et al. |
| 2018/0020285 A1 | 1/2018 | Zass |
| 2018/0020951 A1* | 1/2018 | Kaifosh .................. A61F 2/72 607/48 |
| 2018/0020978 A1 | 1/2018 | Kaifosh et al. |
| 2018/0020990 A1 | 1/2018 | Park et al. |
| 2018/0024634 A1 | 1/2018 | Kaifosh et al. |
| 2018/0024635 A1 | 1/2018 | Kaifosh et al. |
| 2018/0024641 A1 | 1/2018 | Mao et al. |
| 2018/0064363 A1 | 3/2018 | Morun et al. |
| 2018/0067553 A1 | 3/2018 | Morun et al. |
| 2018/0068489 A1 | 3/2018 | Kim et al. |
| 2018/0074332 A1 | 3/2018 | Li et al. |
| 2018/0081439 A1 | 3/2018 | Daniels |
| 2018/0088675 A1 | 3/2018 | Vogel et al. |
| 2018/0088765 A1 | 3/2018 | Bailey |
| 2018/0092599 A1 | 4/2018 | Kerth et al. |
| 2018/0093181 A1 | 4/2018 | Goslin et al. |
| 2018/0095542 A1 | 4/2018 | Mallinson |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0107275 A1 | 4/2018 | Chen et al. |
| 2018/0120948 A1 | 5/2018 | Aleem et al. |
| 2018/0133551 A1 | 5/2018 | Chang et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0168905 A1 | 6/2018 | Goodall et al. |
| 2018/0178008 A1 | 6/2018 | Bouton et al. |
| 2018/0217249 A1 | 8/2018 | La Salla et al. |
| 2018/0239430 A1 | 8/2018 | Tadi et al. |
| 2018/0240459 A1 | 8/2018 | Weng et al. |
| 2018/0247443 A1 | 8/2018 | Briggs et al. |
| 2018/0279919 A1 | 10/2018 | Bansbach et al. |
| 2018/0301057 A1 | 10/2018 | Hargrove et al. |
| 2018/0307314 A1 | 10/2018 | Connor |
| 2018/0314879 A1 | 11/2018 | Khwaja et al. |
| 2018/0321745 A1 | 11/2018 | Morun et al. |
| 2018/0321746 A1 | 11/2018 | Morun et al. |
| 2018/0330549 A1 | 11/2018 | Brenton |
| 2018/0333575 A1 | 11/2018 | Bouton |
| 2018/0344195 A1 | 12/2018 | Morun et al. |
| 2018/0356890 A1 | 12/2018 | Zhang et al. |
| 2018/0360379 A1 | 12/2018 | Harrison et al. |
| 2019/0008453 A1 | 1/2019 | Spoof |
| 2019/0025919 A1 | 1/2019 | Tadi et al. |
| 2019/0027141 A1 | 1/2019 | Strong et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0076716 A1 | 3/2019 | Chiou et al. |
| 2019/0089898 A1 | 3/2019 | Kim et al. |
| 2019/0113973 A1 | 4/2019 | Coleman et al. |
| 2019/0121305 A1 | 4/2019 | Kaifosh et al. |
| 2019/0121306 A1 | 4/2019 | Kaifosh et al. |
| 2019/0146809 A1 | 5/2019 | Lee et al. |
| 2019/0150777 A1* | 5/2019 | Guo .................. A61B 5/30 |
| 2019/0192037 A1 | 6/2019 | Morun et al. |
| 2019/0196585 A1 | 6/2019 | Laszlo et al. |
| 2019/0196586 A1 | 6/2019 | Laszlo et al. |
| 2019/0197778 A1 | 6/2019 | Sachdeva et al. |
| 2019/0209034 A1 | 7/2019 | Deno et al. |
| 2019/0212817 A1 | 7/2019 | Kaifosh et al. |
| 2019/0216619 A1 | 7/2019 | McDonnall et al. |
| 2019/0223748 A1 | 7/2019 | Al-Natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0247650 A1 | 8/2019 | Tran |
| 2019/0279407 A1 | 9/2019 | McHugh et al. |
| 2019/0294243 A1 | 9/2019 | Laszlo et al. |
| 2019/0056422 A1 | 10/2019 | Park et al. |
| 2019/0324549 A1 | 10/2019 | Araki et al. |
| 2019/0332140 A1* | 10/2019 | Wang .................. G06F 3/011 |
| 2019/0348026 A1 | 11/2019 | Berenzweig et al. |
| 2019/0348025 A1 | 11/2019 | Berenzweig et al. |
| 2019/0357787 A1 | 11/2019 | Barachant et al. |
| 2019/0362557 A1 | 11/2019 | Lacey et al. |
| 2020/0042089 A1 | 2/2020 | Ang et al. |
| 2020/0057661 A1 | 2/2020 | Bendfeldt |
| 2020/0065569 A1 | 2/2020 | Nduka et al. |
| 2020/0069210 A1 | 3/2020 | Berenzweig et al. |
| 2020/0069211 A1 | 3/2020 | Berenzweig et al. |
| 2020/0073483 A1 | 3/2020 | Berenzweig et al. |
| 2020/0077955 A1 | 3/2020 | Shui et al. |
| 2020/0097081 A1 | 3/2020 | Stone et al. |
| 2020/0097083 A1 | 3/2020 | Mao et al. |
| 2020/0111260 A1 | 4/2020 | Osborn et al. |
| 2020/0125171 A1 | 4/2020 | Morun et al. |
| 2020/0142490 A1 | 5/2020 | Xiong et al. |
| 2020/0143795 A1 | 5/2020 | Park et al. |
| 2020/0159322 A1 | 5/2020 | Morun et al. |
| 2020/0163562 A1* | 5/2020 | Neaves .................. A61B 5/00 |
| 2020/0205932 A1 | 7/2020 | Zar et al. |
| 2020/0225320 A1 | 7/2020 | Belskikh et al. |
| 2020/0245873 A1 | 8/2020 | Frank et al. |
| 2020/0249752 A1 | 8/2020 | Parshionikar |
| 2020/0275895 A1 | 9/2020 | Barachant |
| 2020/0301509 A1 | 9/2020 | Liu et al. |
| 2020/0305795 A1 | 10/2020 | Floyd et al. |
| 2020/0320335 A1 | 10/2020 | Shamun et al. |
| 2021/0109598 A1 | 4/2021 | Zhang et al. |
| 2021/0117523 A1 | 4/2021 | Kim et al. |
| 2021/0290159 A1 | 9/2021 | Bruinsma et al. |
| 2022/0256706 A1 | 8/2022 | Xiong et al. |

FOREIGN PATENT DOCUMENTS

| | | |
|---|---|---|
| CA | 2939644 A1 | 8/2015 |
| CN | 1838933 A | 9/2006 |
| CN | 101310242 A | 11/2008 |
| CN | 102246125 A | 11/2011 |
| CN | 102349037 A | 2/2012 |
| CN | 103777752 A | 5/2014 |
| CN | 103886215 A | 6/2014 |
| CN | 105009031 A | 10/2015 |
| CN | 105190477 A | 12/2015 |
| CN | 105190578 A | 12/2015 |
| CN | 105511615 A | 4/2016 |
| CN | 106067178 A | 11/2016 |
| CN | 106102504 A | 11/2016 |

(56) References Cited

FOREIGN PATENT DOCUMENTS

| | | |
|---|---|---|
| CN | 106108898 A | 11/2016 |
| CN | 107203272 A | 9/2017 |
| CN | 109620651 A | 4/2019 |
| CN | 110300542 A | 10/2019 |
| CN | 111616847 A | 9/2020 |
| CN | 111902077 A | 11/2020 |
| CN | 112074225 A | 12/2020 |
| CN | 112469469 A | 3/2021 |
| CN | 112822992 A | 5/2021 |
| DE | 4412278 A1 | 10/1995 |
| EP | 0301790 A2 | 2/1989 |
| EP | 1345210 A2 | 9/2003 |
| EP | 1408443 B1 | 10/2006 |
| EP | 2198521 B1 | 6/2012 |
| EP | 2541763 A1 | 1/2013 |
| EP | 2733578 A2 | 5/2014 |
| EP | 2959394 A1 | 12/2015 |
| EP | 3104737 A1 | 12/2016 |
| EP | 3200051 A1 | 8/2017 |
| EP | 3487395 A1 | 5/2019 |
| EP | 3697297 A4 | 12/2020 |
| EP | 2959394 B1 | 5/2021 |
| JP | S61198892 A | 9/1986 |
| JP | H05277080 A | 10/1993 |
| JP | H0639754 A | 2/1994 |
| JP | H07248873 A | 9/1995 |
| JP | 3103427 B2 | 10/2000 |
| JP | 2001054507 A | 2/2001 |
| JP | 2002287869 A | 10/2002 |
| JP | 2003303047 A | 10/2003 |
| JP | 2005095561 A | 4/2005 |
| JP | 2005352739 A | 12/2005 |
| JP | 2008192004 A | 8/2008 |
| JP | 2009050679 A | 3/2009 |
| JP | 2010520561 A | 6/2010 |
| JP | 2013160905 A | 8/2013 |
| JP | 2015512550 A | 4/2015 |
| JP | 2015514467 A | 5/2015 |
| JP | 2016507098 A | 3/2016 |
| JP | 2016507851 A | 3/2016 |
| JP | 2016540276 A | 12/2016 |
| JP | 2017509386 A | 4/2017 |
| JP | 2019023941 A | 2/2019 |
| JP | 2019185531 A | 10/2019 |
| JP | 2021072136 A | 5/2021 |
| KR | 20110040165 A | 4/2011 |
| KR | 20120094870 A | 8/2012 |
| KR | 20120097997 A | 9/2012 |
| KR | 20150123254 A | 11/2015 |
| KR | 20160121552 A | 10/2016 |
| KR | 20170067873 A | 6/2017 |
| KR | 20170107283 A | 9/2017 |
| KR | 10-1790147 B1 | 10/2017 |
| KR | 20190022329 A | 3/2019 |
| WO | 9527341 A1 | 10/1995 |
| WO | 2006086504 A2 | 8/2006 |
| WO | 2008109248 A2 | 9/2008 |
| WO | 2009042313 A1 | 4/2009 |
| WO | 2010095636 A1 | 8/2010 |
| WO | 2010104879 A2 | 9/2010 |
| WO | WO-2011011750 A1 | 1/2011 |
| WO | 2011070554 A2 | 6/2011 |
| WO | 2012155157 A1 | 11/2012 |
| WO | 2013154864 A1 | 10/2013 |
| WO | 2014130871 A1 | 8/2014 |
| WO | WO-2014155288 A2 | 10/2014 |
| WO | 2014186370 A1 | 11/2014 |
| WO | 2014194257 A1 | 12/2014 |
| WO | 2014197443 A1 | 12/2014 |
| WO | 2015027089 A1 | 2/2015 |
| WO | 2015/073713 A1 | 5/2015 |
| WO | WO-2015063520 A1 | 5/2015 |
| WO | 2015081113 A1 | 6/2015 |
| WO | 2015100172 A1 | 7/2015 |
| WO | 2015123445 A1 | 8/2015 |
| WO | WO-2015123775 A1 | 8/2015 |
| WO | 2015184760 A1 | 12/2015 |
| WO | 2015192117 A1 | 12/2015 |
| WO | 2015199747 A1 | 12/2015 |
| WO | 2016/041088 A1 | 3/2016 |
| WO | 2017062544 A1 | 4/2017 |
| WO | 2017075611 A1 | 5/2017 |
| WO | 2017092225 A1 | 6/2017 |
| WO | 2017120669 A1 | 7/2017 |
| WO | 2017172185 A1 | 10/2017 |
| WO | 2017208167 A1 | 12/2017 |
| WO | 2018022602 A1 | 2/2018 |
| WO | 2018098046 A2 | 5/2018 |
| WO | 2019099758 A1 | 5/2019 |
| WO | 2019147953 A1 | 8/2019 |
| WO | 2019147958 A1 | 8/2019 |
| WO | 2019147996 A1 | 8/2019 |
| WO | 2019217419 A2 | 11/2019 |
| WO | 2019226259 A1 | 11/2019 |
| WO | 2019231911 A1 | 12/2019 |
| WO | 2020047429 A1 | 3/2020 |
| WO | 2020061440 A1 | 3/2020 |
| WO | 2020061451 A1 | 3/2020 |
| WO | 2020072915 A1 | 4/2020 |

OTHER PUBLICATIONS

Extended European Search Report for European Application No. 18869441.8, dated Nov. 17, 2020, 20 Pages.
Extended European Search Report for European Application No. 19806723.3, dated Jul. 7, 2021, 13 pages.
Extended European Search Report for European Application No. 19810524.9, dated Mar. 17, 2021, 11 pages.
Extended European Search Report for European Application No. 19850130.6, dated Sep. 1, 2021, 14 Pages.
Extended European Search Report for European Application No. 19855191.3, dated Dec. 6, 2021, 11 pages.
Extended European Search Report for European Application No. 19883839.3, dated Dec. 15, 2021, 7 pages.
Farina D., et al., "Man/Machine Interface Based on the Discharge Timings of Spinal Motor Neurons After Targeted Muscle Reinnervation," Nature Biomedical Engineering, Feb. 6, 2017, vol. 1, Article No. 0025, pp. 1-12.
Favorskaya M., et al., "Localization and Recognition of Dynamic Hand Gestures Based on Hierarchy of Manifold Classifiers," International Archives of the Photogrammetry, Remote Sensing and Spatial Information Sciences, May 25-27, 2015, vol. XL-5/W6, pp. 1-8.
Final Office Action dated Jun. 2, 2020 for U.S. Appl. No. 15/882,858, filed Jan. 29, 2018, 127 Pages.
Final Office Action dated Jun. 2, 2020 for U.S. Appl. No. 16/557,383, filed Aug. 30, 2019, 66 Pages.
Final Office Action dated Nov. 3, 2020 for U.S. Appl. No. 15/974,430, filed May 8, 2018, 27 Pages.
Final Office Action dated Feb. 4, 2020 for U.S. Appl. No. 16/577,207, filed Sep. 20, 2019, 76 Pages.
Final Office Action dated Feb. 4, 2021 for U.S. Appl. No. 15/882,858, filed Jan. 29, 2018, 42 Pages.
Final Office Action dated Jun. 5, 2020 for U.S. Appl. No. 16/557,427, filed Aug. 30, 2019, 95 Pages.
Final Office Action dated Oct. 8, 2020 for U.S. Appl. No. 16/557,342, filed Aug. 30, 2019, 73 Pages.
Final Office Action dated Apr. 9, 2020 for U.S. Appl. No. 15/974,454, filed May 8, 2018, 19 Pages.
Final Office Action dated Dec. 11, 2019 for U.S. Appl. No. 15/974,430, filed May 8, 2018, 30 Pages.
Final Office Action dated Jan. 13, 2021 for U.S. Appl. No. 16/577,207, filed Sep. 20, 2019, 91 Pages.
Final Office Action dated Dec. 18, 2019 for U.S. Appl. No. 16/258,279, filed Jan. 25, 2019, 45 Pages.
Final Office Action dated Feb. 19, 2021 for U.S. Appl. No. 16/258,279, filed Jan. 25, 2019, 58 Pages.
Final Office Action dated Sep. 23, 2020 for U.S. Appl. No. 15/816,435, filed Nov. 17, 2017, 70 Pages.

(56) References Cited

OTHER PUBLICATIONS

Final Office Action dated Jan. 28, 2020 for U.S. Appl. No. 16/557,342, filed Aug. 30, 2019, 15 Pages.
Final Office Action dated Jul. 28, 2017 for U.S. Appl. No. 14/505,836, filed Oct. 3, 2014, 52 Pages.
Final Office Action dated Jun. 28, 2021 for U.S. Appl. No. 16/557,342, filed Aug. 30, 2019, 11 Pages.
Final Office Action dated Nov. 29, 2019 for U.S. Appl. No. 15/659,072, filed Jul. 25, 2017, 36 Pages.
Final Office Action dated Nov. 29, 2019 for U.S. Appl. No. 16/353,998, filed Mar. 14, 2019, 33 Pages.
Fong H.C., et al., "PepperGram With Interactive Control," 22nd International Conference on Virtual System & Multimedia (VSMM), Oct. 17, 2016, 5 pages.
Gallina A., et al., "Surface EMG Biofeedback," Surface Electromyography: Physiology, Engineering, and Applications, 2016, pp. 485-500.
Ghasemzadeh H., et al., "A Body Sensor Network With Electromyogram and Inertial Sensors: Multimodal Interpretation of Muscular Activities," IEEE Transactions on Information Technology in Biomedicine, Mar. 2010, vol. 14 (2), pp. 198-206.
Gopura R.A.R.C., et al., "A Human Forearm and Wrist Motion Assist Exoskeleton Robot With EMG-Based Fuzzy-Neuro Control," Proceedings of the 2nd Biennial IEEE/RAS-EMBS International Conference on Biomedical Robotics and Biomechatronics, Oct. 19-22, 2008, 6 pages.
Gourmelon L., et al., "Contactless Sensors for Surface Electromyography," Proceedings of the 28th IEEE EMBS Annual International Conference, New York City, NY, Aug. 30-Sep. 3, 2006, pp. 2514-2517.
Hauschild M., et al., "A Virtual Reality Environment for Designing and Fitting Neural Prosthetic Limbs," IEEE Transactions on Neural Systems and Rehabilitation Engineering, Mar. 2007, vol. 15 (1), pp. 9-15.
International Search Report and Written Opinion for International Application No. PCT/US2014/017799, dated May 16, 2014, 9 pages.
International Search Report and Written Opinion for International Application No. PCT/US2014/037863, dated Aug. 21, 2014, 10 pages.
International Preliminary Report on Patentability for International Application No. PCT/US2017/043693, dated Feb. 7, 2019, 7 Pages.
International Preliminary Report on Patentability for International Application No. PCT/US2017/043791, dated Feb. 7, 2019, 9 Pages.
International Preliminary Report on Patentability for International Application No. PCT/US2019/031114, dated Nov. 19, 2020, 16 pages.
International Preliminary Report on Patentability for International Application No. PCT/US2019/049094, dated Mar. 11, 2021, 24 Pages.
International Preliminary Report on Patentability for International Application No. PCT/US2019/052151, dated Apr. 1, 2021, 9 pages.
International Preliminary Report on Patentability for International Application No. PCT/US2014/017799, dated Sep. 3, 2015, 8 Pages.
International Preliminary Report on Patentability for International Application No. PCT/US2014/037863, dated Nov. 26, 2015, 8 pages.
International Preliminary Report on Patentability for International Application No. PCT/US2014/052143, dated Mar. 3, 2016, 7 pages.
International Preliminary Report on Patentability for International Application No. PCT/US2014/067443, dated Jun. 9, 2016, 7 pages.
International Preliminary Report on Patentability for International Application No. PCT/US2015/015675, dated Aug. 25, 2016, 8 Pages.
International Preliminary Report on Patentability for International Application No. PCT/US2017/043686, dated Feb. 7, 2019, 8 pages.
International Preliminary Report on Patentability for International Application No. PCT/US2017/043792, dated Feb. 7, 2019, 8 Pages.
International Preliminary Report on Patentability for International Application No. PCT/US2018/056768, dated Apr. 30, 2020, 7 pages.
International Preliminary Report on Patentability for International Application No. PCT/US2018/061409, dated May 28, 2020, 10 pages.
International Preliminary Report on Patentability for International Application No. PCT/US2019/015174, dated Aug. 6, 2020, 7 pages.
International Preliminary Report on Patentability for International Application No. PCT/US2019/015183, dated Aug. 6, 2020, 7 pages.
International Preliminary Report on Patentability for International Application No. PCT/US2019/015238, dated Aug. 6, 2020, 7 pages.
International Preliminary Report on Patentability for International Application No. PCT/US2019/028299, dated Dec. 10, 2020, 11 pages.
International Preliminary Report on Patentability for International Application No. PCT/US2019/034173, dated Dec. 10, 2020, 9 pages.
International Preliminary Report on Patentability for International Application No. PCT/US2019/046351, dated Feb. 25, 2021, 8 pages.
International Preliminary Report on Patentability for International Application No. PCT/US2019/052131, dated Apr. 1, 2021, 8 pages.
International Preliminary Report on Patentability for International Application No. PCT/US2019/054716, dated Apr. 15, 2021, 10 pages.
International Preliminary Report on Patentability for International Application No. PCT/US2019/061759, dated May 27, 2021, 12 pages.
International Preliminary Report on Patentability for International Application No. PCT/US2019/063587, dated Jun. 10, 2021, 13 pages.
International Preliminary Report on Patentability for International Application No. PCT/US2020/049274, dated Mar. 17, 2022, 14 pages.
International Preliminary Report on Patentability for International Application No. PCT/US2020/061392, dated Jun. 9, 2022, 11 pages.
International Search Report and Written Opinion for International Application No. PCT/US2014/052143, dated Nov. 21, 2014, 8 Pages.
International Search Report and Written Opinion for International Application No. PCT/US2014/067443, dated Feb. 27, 2015, 8 pages.
International Search Report and Written Opinion for International Application No. PCT/US2015/015675, dated May 27, 2015, 9 Pages.
International Search Report and Written Opinion for International Application No. PCT/US2017/043686, dated Oct. 6, 2017, 9 Pages.
International Search Report and Written Opinion for International Application No. PCT/US2017/043693, dated Oct. 6, 2017, 7 Pages.
International Search Report and Written Opinion for International Application No. PCT/US2017/043791, dated Oct. 5, 2017, 10 Pages.
International Search Report and Written Opinion for International Application No. PCT/US2018/056768, dated Jan. 15, 2019, 8 pages.
International Search Report and Written Opinion for International Application No. PCT/US2018/061409, dated Mar. 12, 2019, 11 pages.
International Search Report and Written Opinion for International Application No. PCT/US2018/063215, dated Mar. 21, 2019, 17 Pages.
International Search Report and Written Opinion for International Application No. PCT/US2019/015167, dated May 21, 2019, 7 Pages.
International Search Report and Written Opinion for International Application No. PCT/US2019/015174, dated May 21, 2019, 8 pages.
International Search Report and Written Opinion for International Application No. PCT/US2019/015244, dated May 16, 2019, 8 Pages.

(56) References Cited

OTHER PUBLICATIONS

International Search Report and Written Opinion for International Application No. PCT/US2019/020065, dated May 16, 2019, 10 Pages.
International Search Report and Written Opinion for International Application No. PCT/US2019/028299, dated Aug. 9, 2019, 12 pages.
International Search Report and Written Opinion for International Application No. PCT/US2019/031114, dated Dec. 20, 2019, 18 Pages.
International Search Report and Written Opinion for International Application No. PCT/US2019/034173, dated Sep. 18, 2019, 10 Pages.
International Search Report and Written Opinion for International Application No. PCT/US2019/037302, dated Oct. 11, 2019, 13 Pages.
International Search Report and Written Opinion for International Application No. PCT/US2019/042579, dated Oct. 31, 2019, 8 Pages.
International Search Report and Written Opinion for International Application No. PCT/US2019/046351, dated Nov. 7, 2019, 9 pages.
International Search Report and Written Opinion for International Application No. PCT/US2019/049094, dated Jan. 9, 2020, 27 Pages.
International Search Report and Written Opinion for International Application No. PCT/US2019/052131, dated Dec. 6, 2019, 8 pages.
International Search Report and Written Opinion for International Application No. PCT/US2019/052151, dated Jan. 15, 2020, 10 pages.
International Search Report and Written Opinion for International Application No. PCT/US2019/054716, dated Dec. 20, 2019, 11 Pages.
International Search Report and Written Opinion for International Application No. PCT/US2019/061759, dated Jan. 29, 2020, 12 pages.
International Search Report and Written Opinion for International Application No. PCT/US2019/063587, dated Mar. 25, 2020, 16 pages.
International Search Report and Written Opinion for International Application No. PCT/US2020/025735, dated Jun. 22, 2020, 10 pages.
International Search Report and Written Opinion for International Application No. PCT/US2020/025772, dated Aug. 3, 2020, 11 pages.
International Search Report and Written Opinion for International Application No. PCT/US2020/025797, dated Jul. 9, 2020, 10 pages.
International Search Report and Written Opinion for International Application No. PCT/US2020/049274, dated Feb. 1, 2021, 17 pages.
International Search Report and Written Opinion for International Application No. PCT/US2020/061392, dated Mar. 12, 2021, 12 pages.
International Search Report and Written Opinion for International Application No. PCT/US2017/043792, dated Oct. 5, 2017, 9 Pages.
International Search Report and Written Opinion for International Application No. PCT/US2019/015134, dated May 15, 2019, 11 Pages.
International Search Report and Written Opinion for International Application No. PCT/US2019/015180, dated May 28, 2019, 10 Pages.
International Search Report and Written Opinion for International Application No. PCT/US2019/015183, dated May 3, 2019, 8 Pages.
International Search Report and Written Opinion for International Application No. PCT/US2019/015238, dated May 16, 2019, 8 Pages.
Invitation to Pay Additional Fees for International Application No. PCT/US2019/031114, dated Aug. 6, 2019, 7 pages.
Invitation to Pay Additional Fees for International Application No. PCT/US2019/049094, dated Oct. 24, 2019, 2 Pages.
Jiang H., "Effective and Interactive Interpretation of Gestures by Individuals with Mobility Impairments," Thesis/Dissertation Acceptance, Purdue University Graduate School, Graduate School Form 30, Updated on Jan. 15, 2015, 24 pages.
Kainz et al., "Approach to Hand Tracking and Gesture Recognition Based on Depth-Sensing Cameras and EMG Monitoring," ACTA Informatica Pragensia, vol. 3, Jan. 1, 2014, pp. 104-112, Retrieved from the Internet: URL: https://aip.vse.cz/pdfs/aip/2014/01/08.pdf.
Kawaguchi J., et al., "Estimation of Finger Joint Angles Based on Electromechanical Sensing of Wrist Shape," IEEE Transactions on Neural Systems and Rehabilitation Engineering, Sep. 2017, vol. 25 (9), pp. 1409-1418.
Kim H., et al., "Real-Time Human Pose Estimation and Gesture Recognition from Depth Images Using Superpixels and SVM Classifier," Sensors, 2015, vol. 15, pp. 12410-12427.
Kipke D.R., et al., "Silicon-Substrate Intracortical Microelectrode Arrays for Long-Term Recording of Neuronal Spike Activity in Cerebral Cortex," IEEE Transactions on Neural Systems and Rehabilitation Engineering, Jun. 2003, vol. 11 (2), 5 pages, Retrieved on Oct. 7, 2019 [Oct. 7, 2019] Retrieved from the Internet: URL: https://www.ece.uvic.ca/-bctill/papers/neurimp/Kipke_etal_2003_01214707.pdf.
Koerner M.D., "Design and Characterization of the Exo-Skin Haptic Device: A Novel Tendon Actuated Textile Hand Exoskeleton," Abstract of thesis for Drexel University Masters Degree [online], Nov. 2, 2017, 5 pages, Retrieved from the Internet: URL: https://dialog.proquest.com/professional/docview/1931047627?accountid=153692.
Lee D.C., et al., "Motion and Force Estimation System of Human Fingers," Journal of Institute of Control, Robotics and Systems, 2011, vol. 17 (10), pp. 1014-1020.
Li Y., et al., "Motor Function Evaluation of Hemiplegic Upper-Extremities Using Data Fusion from Wearable Inertial and Surface EMG Sensors," Sensors, MDPI, 2017, vol. 17 (582), pp. 1-17.
Lopes J., et al., "Hand/Arm Gesture Segmentation by Motion Using IMU and EMG Sensing," ScienceDirect, Jun. 27-30, 2017, vol. 11, pp. 107-113.
Marcard T.V., et al., "Sparse Inertial Poser: Automatic 3D Human Pose Estimation from Sparse IMUs," arxiv.org, Computer Graphics Forum, 2017, vol. 36 (2), 12 pages, XP080759137.
Martin H., et al., "A Novel Approach of Prosthetic Arm Control using Computer Vision, Biosignals, and Motion Capture," IEEE Symposium on Computational Intelligence in Robotic Rehabilitation and Assistive Technologies (CIR2AT), 2014, 5 pages.
McIntee S.S., "A Task Model of Free-Space Movement-Based Geastures," Dissertation, Graduate Faculty of North Carolina State University, Computer Science, 2016, 129 pages.
Mendes Jr.J.J.A., et al., "Sensor Fusion and Smart Sensor in Sports and Biomedical Applications," Sensors, 2016, vol. 16 (1569), pp. 1-31.
Mohamed O.H., "Homogeneous Cognitive Based Biometrics for Static Authentication," Dissertation submitted to University of Victoria, Canada, 2010, [last accessed Oct. 11, 2019], 149 pages, Retrieved from the Internet: URL: http://hdl.handle.net/1828/321.
Morris D., et al., "Emerging Input Technologies for Always-Available Mobile Interaction," Foundations and Trends in Human-Computer Interaction, 2010, vol. 4 (4), pp. 245-316.
Naik G.R., et al., "Source Separation and Identification issues in Bio Signals: A Solution using Blind Source Separation," Chapter 4 of Recent Advances in Biomedical Engineering, Intech, 2009, 23 pages.
Naik G.R., et al., "Real-Time Hand Gesture Identification for Human Computer Interaction Based on ICA of Surface Electromyogram," IADIS International Conference Interfaces and Human Computer Interaction, 2007, pp. 83-90.
Naik G.R., et al., "Subtle Hand Gesture Identification for HCI Using Temporal Decorrelation Source Separation BSS of Surface EMG," Digital Image Computing Techniques and Applications, IEEE Computer Society, 2007, pp. 30-37.
Negro F., et al., "Multi-Channel Intramuscular and Surface EMG Decomposition by Convolutive Blind Source Separation," Journal of Neural Engineering, Feb. 29, 2016, vol. 13, 18 Pages.

(56) References Cited

OTHER PUBLICATIONS

Non-Final Office Action dated Mar. 2, 2021 for U.S. Appl. No. 15/974,430, filed May 8, 2018, 32 Pages.
Non-Final Office Action dated Sep. 2, 2020 for U.S. Appl. No. 15/882,858, filed Jan. 29, 2018, 66 Pages.
Non-Final Office Action dated Aug. 3, 2020 for U.S. Appl. No. 16/593,446, filed Oct. 4, 2019, 44 pages.
Non-Final Office Action dated Jun. 3, 2021 for U.S. Appl. No. 15/816,435, filed Nov. 17, 2017, 32 Pages.
Non-Final Office Action dated Jun. 5, 2020 for U.S. Appl. No. 15/659,072, filed Jul. 25, 2017, 59 Pages.
Non-Final Office Action dated Sep. 6, 2019 for U.S. Appl. No. 16/424,144, filed May 28, 2019, 11 Pages.
Non-Final Office Action dated Feb. 8, 2021 for U.S. Appl. No. 16/557,342, filed Aug. 30, 2019, 11 Pages.
Non-Final Office Action dated Oct. 8, 2020 for U.S. Appl. No. 16/577,207, filed Sep. 20, 2019, 51 Pages.
Non-Final Office Action dated Apr. 9, 2019 for U.S. Appl. No. 16/258,409, filed Jan. 25, 2019, 71 Pages.
Non-Final Office Action dated Aug. 11, 2021 for U.S. Appl. No. 16/577,207, filed Sep. 20, 2019, 35 Pages.
Non-Final Office Action dated Jun. 13, 2019 for U.S. Appl. No. 16/258,279, filed Jan. 25, 2019, 38 Pages.
Non-Final Office Action dated Jun. 15, 2020 for U.S. Appl. No. 16/557,342, filed Aug. 30, 2019, 46 Pages.
Non-Final Office Action dated Jan. 16, 2020 for U.S. Appl. No. 16/389,419, filed Apr. 19, 2019, 26 Pages.
Non-Final Office Action dated May 16, 2019 for U.S. Appl. No. 15/974,384, filed May 8, 2018, 13 Pages.
Non-Final Office Action dated May 16, 2019 for U.S. Appl. No. 15/974,430, filed May 8, 2018, 12 Pages.
Non-Final Office Action dated Nov. 19, 2019 for U.S. Appl. No. 16/577,207, filed Sep. 20, 2019, 32 Pages.
Non-Final Office Action dated Aug. 20, 2020 for U.S. Appl. No. 15/974,454, filed May 8, 2018, 59 Pages.
Non-Final Office Action dated Dec. 20, 2019 for U.S. Appl. No. 15/974,454, filed May 8, 2018, 41 Pages.
Non-Final Office Action dated Jan. 22, 2020 for U.S. Appl. No. 15/816,435, filed Nov. 17, 2017, 35 Pages.
Non-Final Office Action dated Oct. 22, 2019 for U.S. Appl. No. 16/557,342, filed Aug. 30, 2019, 16 Pages.
Non-Final Office Action dated Dec. 23, 2019 for U.S. Appl. No. 16/557,383, filed Aug. 30, 2019, 53 Pages.
Non-Final Office Action dated Dec. 23, 2019 for U.S. Appl. No. 16/557,427, filed Aug. 30, 2019, 52 Pages.
Non-Final Office Action dated Feb. 23, 2017 for U.S. Appl. No. 14/505,836, filed Oct. 3, 2014, 54 Pages.
Non-Final Office Action dated Jul. 23, 2020 for U.S. Appl. No. 16/593,446, filed Oct. 4, 2019, 28 pages.
Non-Final Office Action dated May 24, 2019 for U.S. Appl. No. 16/353,998, filed Mar. 14, 2019, 20 Pages.
Non-Final Office Action dated May 26, 2020 for U.S. Appl. No. 16/353,998, filed Mar. 14, 2019, 60 Pages.
Non-Final Office Action dated Nov. 27, 2020 for U.S. Appl. No. 16/258,279, filed Jan. 25, 2019, 44 Pages.
Non-Final Office Action dated Apr. 29, 2019 for U.S. Appl. No. 16/257,979, filed Jan. 25, 2019, 63 Pages.
Non-Final Office Action dated Apr. 30, 2019 for U.S. Appl. No. 15/659,072, filed Jul. 25, 2017, 99 Pages.
Non-Final Office Action dated Apr. 30, 2020 for U.S. Appl. No. 15/974,430, filed May 8, 2018, 57 Pages.
Non-Final Office Action dated Dec. 30, 2019 for U.S. Appl. No. 16/593,446, filed Oct. 4, 2019, 43 pages.
Non-Final Office Action dated Jun. 30, 2016 for U.S. Appl. No. 14/505,836, filed Oct. 3, 2014, 37 Pages.
Non-Final Office Action dated Oct. 30, 2019 for U.S. Appl. No. 15/882,858, filed Jan. 29, 2018, 22 Pages.
Al-Jumaily A., et al., "Electromyogram(EMG) Driven System based Virtual Reality for Prosthetic and Rehabilitation Devices," Proceedings of the 11th InternationalConference on Information Integration andWeb-Based Applications & Services, Jan. 1, 2009, pp. 582-586.
Al-Mashhadany Y.I., "Inverse Kinematics Problem (IKP) of 6-DOF Manipulator By Locally Recurrent Neural Networks (LRNNs)," Management and Service Science (MASS), International Conference on Management and Service Science., IEEE, Aug. 24, 2010, 5 pages.
Al-Timemy A.H., et al., "Improving the Performance Against Force Variation of EMG Controlled Multifunctional Upper-Limb Prostheses for Transradial Amputees," IEEE Transactions on Neural Systems and Rehabilitation Engineering, Jun. 2016, vol. 24 (6), 12 Pages.
Arkenbout E.A., et al., "Robust Hand Motion Tracking through Data Fusion of 5DT Data Glove and Nimble VR Kinect Camera Measurements," Sensors, 2015, vol. 15, pp. 31644-31671.
Benko H., et al., "Enhancing Input On and Above the Interactive Surface with Muscle Sensing," The ACM International Conference on Interactive Tabletops and Surfaces (ITS), Nov. 23-25, 2009, pp. 93-100.
Berenzweig A., et al., "Wearable Devices and Methods for Improved Speech Recognition," U.S. Appl. No. 16/785,680, filed Feb. 10, 2020, 67 pages.
Boyali A., et al., "Spectral Collaborative Representation based Classification for Hand Gestures Recognition on Electromyography Signals," Biomedical Signal Processing and Control, 2016, vol. 24, pp. 11-18.
Brownlee J., "Finite State Machines (FSM): Finite State Machines as a Control Technique in Artificial Intelligence (AI)," FSM, Jun. 2002, 12 pages.
Cannan J., et al., "A Wearable Sensor Fusion Armband for Simple Motion Control and Selection for Disabled and Non-Disabled Users," Computer Science and Electronic Engineering Conference, IEEE, Sep. 12, 2012, pp. 216-219, XP032276745.
Cheng J., et al., "A Novel Phonology- and Radical-Coded Chinese Sign Language Recognition Framework Using Accelerometer and Surface Electromyography Sensors," Sensors, 2015, vol. 15, pp. 23303-23324.
Communication Pursuant to Article 94(3) for European Patent Application No. 17835112.8, dated Dec. 14, 2020, 6 Pages.
Communication Pursuant to Rule 164(1) EPC, Partial Supplementary European Search Report for European Application No. 14753949.8, dated Sep. 30, 2016, 7 pages.
Co-pending U.S. Appl. No. 15/659,072, inventors Patrick; Kaifosh et al., filed Jul. 25, 2017.
Co-pending U.S. Appl. No. 15/816,435, inventors Ning; Guo et al., filed Nov. 17, 2017.
Co-pending U.S. Appl. No. 15/882,858, inventors Stephen; Lake et al., filed Jan. 29, 2018.
Co-pending U.S. Appl. No. 15/974,430, inventors Adam; Berenzweig et al., filed May 8, 2018.
Co-pending U.S. Appl. No. 16/353,998, inventors Patrick; Kaifosh et al., filed Mar. 14, 2019.
Co-pending U.S. Appl. No. 16/557,383, inventors Adam; Berenzweig et al., filed Aug. 30, 2019.
Co-pending U.S. Appl. No. 16/557,427, inventors Adam; Berenzweig et al., filed Aug. 30, 2019.
Co-Pending U.S. Appl. No. 15/974,430, filed May 8, 2018, 44 Pages.
Co-Pending U.S. Appl. No. 16/353,998, filed Mar. 14, 2019, 43 pages.
Co-Pending U.S. Appl. No. 16/557,383, filed Aug. 30, 2019, 94 Pages.
Co-Pending U.S. Appl. No. 16/557,427, filed Aug. 30, 2019, 93 Pages.
Co-Pending U.S. Appl. No. 16/577,207, filed Sep. 20, 2019, 67 Pages.
Co-Pending U.S. Appl. No. 14/505,836, filed Oct. 3, 2014, 59 Pages.
Co-Pending U.S. Appl. No. 15/816,435, filed Nov. 17, 2017, 24 Pages.
Co-Pending U.S. Appl. No. 15/882,858, filed Jan. 29, 2018, 54 Pages.

(56) References Cited

OTHER PUBLICATIONS

Co-Pending U.S. Appl. No. 15/974,384, filed May 8, 2018, 44 Pages.

Co-Pending U.S. Appl. No. 15/974,454, filed May 8, 2018, 45 Pages.

Co-Pending U.S. Appl. No. 16/557,342, filed Aug. 30, 2019, 93 Pages.

Corazza S., et al.,"A Markerless Motion Capture System to Study Musculoskeletal Biomechanics: Visual Hull and Simulated Annealing Approach," Annals of Biomedical Engineering, Jul. 2006, vol. 34 (6), pp. 1019-1029, [Retrieved on Dec. 11, 2019], 11 pages, Retrieved from the Internet: URL: https://www.researchgate.net/publication/6999610_A_Markerless_Motion_Capture_System_to_Study_Musculoskeletal_Biomechanics_Visual_Hull_and_Simulated_Annealing_Approach.

Costanza E., et al., "EMG as a Subtle Input Interface for Mobile Computing," Mobile HCI, LNCS 3160, 2004, pp. 426-430.

Costanza E., et al., "Toward Subtle Intimate Interfaces for Mobile Devices Using an EMG Controller," CHI, Proceedings of the SIGCHI Conference on Human Factors in Computing Systems, Apr. 2-7, 2005, pp. 481-489.

Cote-Allard U., et al., "Deep Learning for Electromyographic Hand Gesture Signal Classification Using Transfer Learning," IEEE Transactions on Neural Systems and Rehabilitation Engineering, Jan. 26, 2019, vol. 27 (4), 11 Pages.

Csapo A.B., et al., "Evaluation of Human-Myo Gesture Control Capabilities in Continuous Search and Select Operations," 7th IEEE International Conference on Cognitive Infocommunications, Oct. 16-18, 2016, pp. 000415-000420.

Davoodi R., et al., "Development of a Physics-Based Target Shooting Game to Train Amputee Users of Multi joint Upper Limb Prostheses," Presence, Massachusetts Institute of Technology, 2012, vol. 21 (1), pp. 85-95.

Delis A.L., et al., "Development of a Myoelectric Controller Based on Knee Angle Estimation," Biodevices, International Conference on Biomedical Electronics and Devices, Jan. 17, 2009, 7 pages.

Diener L., et al., "Direct Conversion From Facial Myoelectric Signals to Speech Using Deep Neural Networks," International Joint Conference on Neural Networks (IJCNN), Oct. 1, 2015, 7 pages.

Ding I-J., et al., "HMM with Improved Feature Extraction-Based Feature Parameters for Identity Recognition of Gesture Command Operators by Using a Sensed Kinect-Data Stream," Neurocomputing, 2017, vol. 262, pp. 108-119.

European Search Report for European Application No. 19861903.3, dated Oct. 12, 2021, 2 pages.

European Search Report for European Application No. 19863248.1, dated Oct. 19, 2021, 2 pages.

European Search Report for European Application No. 19868789.9, dated May 9, 2022, 9 pages.

European Search Report for European Application No. 19890394.0, dated Apr. 29, 2022, 9 pages.

Extended European Search Report for European Application No. 18879156.0, dated Mar. 12, 2021, 11 pages.

Extended European Search Report for European Application No. 19743717.1, dated Mar. 3, 2021, 12 pages.

Extended European Search Report for European Application No. 19744404.5, dated Mar. 29, 2021, 11 pages.

Extended European Search Report for European Application No. 19799947.7, dated May 26, 2021, 10 pages.

Extended European Search Report for European Application No. 17835111.0, dated Nov. 21, 2019, 6 pages.

Extended European Search Report for European Application No. 17835112.8, dated Feb. 5, 2020, 17 pages.

Extended European Search Report for European Application No. 17835140.9, dated Nov. 26, 2019, 10 Pages.

Notice of Allowance dated Aug. 22, 2022 for U.S. Appl. No. 15/882,858, filed Jan. 29, 2018, 9 pages.

Notice of Allowance dated Nov. 2, 2020 for U.S. Appl. No. 15/974,454, filed May 8, 2018, 24 Pages.

Notice of Allowance dated Nov. 4, 2019 for U.S. Appl. No. 15/974,384, filed May 8, 2018, 39 Pages.

Notice of Allowance dated Feb. 6, 2020 for U.S. Appl. No. 16/424,144, filed May 28, 2019, 28 Pages.

Notice of Allowance dated Feb. 9, 2022 for U.S. Appl. No. 15/882,858, filed Jan. 29, 2018, 9 pages.

Notice of Allowance dated Nov. 10, 2021 for U.S. Appl. No. 15/882,858, filed Jan. 29, 2018, 6 pages.

Notice of Allowance dated Jul. 15, 2021 for U.S. Appl. No. 15/882,858, filed Jan. 29, 2018, 2 pages.

Notice of Allowance dated Dec. 16, 2020 for U.S. Appl. No. 16/593,446, filed Oct. 4, 2019, 44 pages.

Notice of Allowance dated May 18, 2020 for U.S. Appl. No. 16/258,279, filed Jan. 25, 2019, 42 Pages.

Notice of Allowance dated May 18, 2022 for U.S. Appl. No. 15/882,858, filed Jan. 29, 2018, 10 pages.

Notice of Allowance dated Aug. 19, 2020 for U.S. Appl. No. 16/557,427, filed Aug. 30, 2019, 22 Pages.

Notice of Allowance dated Jul. 19, 2019 for U.S. Appl. No. 16/258,409, filed Jan. 25, 2019, 36 Pages.

Notice of Allowance dated May 20, 2020 for U.S. Appl. No. 16/389,419, filed Apr. 19, 2019, 28 Pages.

Notice of Allowance dated Oct. 22, 2021 for U.S. Appl. No. 15/882,858, filed Jan. 29, 2018 , 8 pages.

Notice of Allowance dated Aug. 23, 2021 for U.S. Appl. No. 15/974,430, filed May 8, 2018, 12 pages.

Notice of Allowance dated Dec. 23, 2020 for U.S. Appl. No. 15/659,072, filed Jul. 25, 2017, 26 Pages.

Notice of Allowance dated Jun. 28, 2021 for U.S. Appl. No. 15/882,858, filed Jan. 29, 2018, 18 pages.

Notice of Allowance dated Jul. 31, 2019 for U.S. Appl. No. 16/257,979, filed Jan. 25, 2019, 22 Pages.

Office action for European Application No. 17835112.8, dated Feb. 11, 2022, 11 Pages.

Office Action for European Patent Application No. 19743717.1, dated Apr. 11, 2022, 10 pages.

Partial Supplementary European Search Report for European Application No. 18879156.0, dated Dec. 7, 2020, 9 pages.

Picard R.W., et al., "Affective Wearables," Proceedings of the IEEE 1st International Symposium on Wearable Computers, ISWC, Cambridge, MA, USA, Oct. 13-14, 1997, pp. 90-97.

Preinterview First Office Action dated Jun. 24, 2020 for U.S. Appl. No. 16/785,680, filed Feb. 10, 2020, 90 Pages.

Rekimoto J., "GestureWrist and GesturePad: Unobtrusive Wearable Interaction Devices," ISWC Proceedings of the 5th IEEE International Symposium on Wearable Computers, 2001, 7 pages.

Saponas T.S., et al., "Demonstrating the Feasibility of Using Forearm Electromyography for Muscle-Computer Interfaces," CHI Proceedings, Physiological Sensing for Input, Apr. 5-10, 2008, pp. 515-524.

Saponas T.S., et al., "Enabling Always-Available Input with Muscle-Computer Interfaces," Conference: Proceedings of the 22nd Annual ACM Symposium on User Interface Software and Technology, Oct. 7, 2009, pp. 167-176.

Saponas T.S., et al., "Making Muscle-Computer Interfaces More Practical," CHI, Atlanta, Georgia, USA, Apr. 10-15, 2010, 4 pages.

Sartori M., et al., "Neural Data-Driven Musculoskeletal Modeling for Personalized Neurorehabilitation Technologies," IEEE Transactions on Biomedical Engineering, May 5, 2016, vol. 63 (5), pp. 879-893.

Sato M., et al., "Touche: Enhancing Touch Interaction on Humans, Screens, Liquids, and Everyday Objects," CHI, Austin, Texas, May 5-10, 2012, 10 pages.

Sauras-Perez P., et al., "A Voice and Pointing Gesture Interaction System for Supporting Human Spontaneous Decisions in Autonomous Cars," Clemson University, All Dissertations, May 2017, 174 pages.

Shen S., et al., "I Am a Smartwatch and I Can Track My User's Arm," University of Illinois at Urbana-Champaign, MobiSys, Jun. 25-30, 2016, 12 pages.

Son M., et al., "Evaluating the Utility of Two Gestural Discomfort Evaluation Methods," PLoS One, Apr. 19, 2017, 21 pages.

(56) References Cited

OTHER PUBLICATIONS

Strbac M., et al., "Microsoft Kinect-Based Artificial Perception System for Control of Functional Electrical Stimulation Assisted Grasping," Hindawi Publishing Corporation, BioMed Research International [online], 2014, Article No. 740469, 13 pages, Retrieved from the Internet: URL: https://dx.doi.org/10.1155/2014/740469.
Torres T., "Myo Gesture Control Armband," PCMag, Jun. 8, 2015, 9 pages, Retrieved from the Internet: URL: https://www.pcmag.com/article2/0,2817,2485462,00.asp.
Ueno A., et al., "A Capacitive Sensor System for Measuring Laplacian Electromyogram through Cloth: A Pilot Study," Proceedings of the 29th Annual International Conference of the IEEE EMBs, Cite Internationale, Lyon, France, Aug. 23-26, 2007, pp. 5731-5734.
Ueno A., et al., "Feasibility of Capacitive Sensing of Surface Electromyographic Potential through Cloth," Sensors and Materials, 2012, vol. 24 (6), pp. 335-346.
Valero-Cuevas F.J., et al., "Computational Models for Neuromuscular Function," IEEE Reviews in Biomedical Engineering, 2009, vol. 2, NIH Public Access Author Manuscript [online], Jun. 16, 2011 [Retrieved on Jul. 29, 2019], 52 pages, Retrieved from the Internet: URL: https://www.ncbi.nlm.nih.gov/pmc/articles/PMC3116649/.
Wittevrongel B., et al., "Spatiotemporal Beamforming: A Transparent and Unified Decoding Approach to Synchronous Visual Brain-Computer Interfacing," Frontiers in Neuroscience, Nov. 15, 2017, vol. 11, Article No. 630, 13 Pages.
Wodzinski M., et al., "Sequential Classification of Palm Gestures Based on A* Algorithm and MLP Neural Network for Quadrocopter Control," Metrology and Measurement Systems, 2017, vol. 24 (2), pp. 265-276.
Xiong A., et al., "A Novel HCI based on EMG and IMU," Proceedings of the 2011 IEEE International Conference on Robotics and Biomimetics, Phuket, Thailand, Dec. 7-11, 2011, pp. 2653-2657.
Xu Z., et al., "Hand Gesture Recognition and Virtual Game Control Based on 3D Accelerometer and EMG Sensors," Proceedings of the 14th International Conference on Intelligent User Interfaces, D211 Sanibel Island, Florida, Feb. 8-11, 2009, pp. 401-406.
Xue Y., et al., "Multiple Sensors Based Hand Motion Recognition Using Adaptive Directed Acyclic Graph," Applied Sciences, MDPI, 2017, vol. 7 (358), pp. 1-14.
Yang Z., et al., "Surface EMG Based Handgrip Force Predictions Using Gene Expression Programming," Neurocomputing, 2016, vol. 207, pp. 568-579.
Zacharaki E.I., et al., "Spike Pattern Recognition by Supervised Classification in Low Dimensional Embedding Space," Brain Informatics, 2016, vol. 3, pp. 73-83.
Zhang X., et al., "A Framework for Hand Gesture Recognition Based on Accelerometer and EMG Sensors," IEEE Transactions on Systems, Man, and Cybernetics—Part A: Systems and Humans, Nov. 2011, vol. 41 (6), pp. 1064-1076.
Tibold R., et al., "Prediction of Muscle Activity during Loaded Movements of The Upper Limb," Journal of NeuroEngineering Rehabilitation, 2015 vol. 12, No. 6, DOI: https://doi.org/10.1186/1743-0003-12-6, 12 pages.
Amitai Y., "P-27: A Two-Dimensional Aperture Expander for Ultra-Compact, High-Performance Head-Worn Displays," SID Symposium Digest of Technical Papers, 2005, vol. 36 (1), pp. 360-363.
Ayras P., et al., "Exit Pupil Expander With a Large Field of View Based on Diffractive Optics," Journal of the SID, 2009, vol. 17 (8), pp. 659-664.
Bailey et al., Wearable Muscle Interface Systems, Devices and Methods That Interact With Content Displayed on an Electronic Display, Office Action dated Mar. 31, 2015, for U.S. Appl. No. 14/155,107, 17 pages.
Bailey et al., "Muscle Interface Device and Method for Interacting With Content Displayed on Wearable Head Mounted Displays," Amendment filed Aug. 25, 2015, for U.S. Appl. No. 14/155,087, 10 pages.

Bailey et al., "Muscle Interface Device and Method for Interacting With Content Displayed on Wearable Head Mounted Displays," Amendment filed Aug. 9, 2016, for U.S. Appl. No. 14/155,087, 8 pages.
Bailey et al., "Muscle Interface Device and Method for Interacting With Content Displayed on Wearable Head Mounted Displays," Amendment filed May 17, 2016, for U.S. Appl. No. 14/155,087, 13 pages.
Bailey et al., "Muscle Interface Device and Method for Interacting With Content Displayed on Wearable Head Mounted Displays," Office Action dated Feb. 17, 2016, for U.S. Appl. No. 14/155,087, 16 pages.
Bailey et al., "Muscle Interface Device and Method for Interacting With Content Displayed on Wearable Head Mounted Displays," Office Action dated Jul. 20, 2015, for U.S. Appl. No. 14/155,087, 14 pages.
Bailey et al., "Muscle Interface Device and Method for Interacting With Content Displayed on Wearable Head Mounted Displays," Office Action dated Jul. 8, 2016, for U.S. Appl. No. 14/155,087, 16 pages.
Bailey et al., "Muscle Interface Device and Method for Interacting With Content Displayed on Wearable Head Mounted Displays," Office Action dated Mar. 31, 2015, for U.S. Appl. No. 14/155,087, 15 pages.
Bailey et al., "Muscle Interface Device and Method for Interacting With Content Displayed on Wearable Head Mounted Displays," Preliminary Amendment filed Jan. 28, 2014, for U.S. Appl. No. 14/155,087, 8 pages.
Bailey et al., "Wearable Muscle Interface Systems, Devices and Methods That Interact With. Content Displayed on an Electronic Display," Amendment filed Aug. 9, 2016, for U.S. Appl. No. 14/155,107, 8 pages.
Bailey et al., "Wearable Muscle Interface Systems, Devices and Methods That Interact With Content Displayed on an Electronic Display," Amendment filed May 11, 2016, for U.S. Appl. No. 14/155,107, 15 pages.
Bailey et al., Wearable Muscle Interface Systems, Devices and Methods That Interact With Content Displayed on an Electronic Display/ Office Action dated Feb. 11, 2016, for U.S. Appl. No. 14/155,107, 20 pages.
Bailey et al., Wearable Muscle Interface Systems, Devices and Methods That Interact With Content Displayed on an Electronic Display, Office Action dated Jul. 16, 2015, for U.S. Appl. No. 14/155,107, 20 pages.
Bailey et al., Wearable Muscle Interface Systems. Devices and Methods That Interact With Content Displayed on an Electronic Display/ Office Action dated Jul. 8, 2016, for U.S. Appl. No. 14/155,107, 21 pages.
Bailey., et al., "Wearable Muscle Interface Systems, Devices And Methods That Interact With Content Displayed on an Electronic Display," Office Action dated Mar. 31, 2015, for U.S. Appl. No. 14/155,107, 17 pages.
Chellappan K.V., et al., "Laser-Based Displays: A Review," Applied Optics, Sep. 1, 2010, vol. 49 (25), pp. F79-F98.
Co-Pending U.S. Appl. No. 16/430,299, filed Jun. 3, 2019, 42 Pages.
Cui L., et al., "Diffraction From Angular Multiplexing Slanted Volume Hologram Gratings," Optik, 2005, vol. 116, pp. 118-122.
Curatu C., et al., "Dual Purpose Lens for an Eye-Tracked Projection Head-Mounted Display," International Optical Design Conference SPIE-OSA, 2006, vol. 6342, pp. 63420X-1-63420X-7.
Curatu C., et al., "Projection-Based Head-Mounted Display With Eye-Tracking Capabilities," Proceedings of SPIE, 2005, vol. 5875, pp. 58750J-1-58750J-9.
Essex D., "Tutorial on Optomechanical Beam Steering Mechanisms," OPTI 521 Tutorial, College of Optical Sciences, University of Arizona, 2006, 8 pages.
Farina D., et al., "The Extraction of Neural Information from the Surface EMG for the Control of Upper-Limb Prostheses: Emerging Avenues and Challenges," IEEE Transactions on Neural Systems andRehabilitation Engineering, vol. 22, No. 4, Jul. 1, 2014, pp. 797-809.
Fernandez E., et al., "Optimization of a Thick Polyvinyl Alcohol-Acrylamide Photopolymer for Data Storage Using a Combination of

(56) References Cited

OTHER PUBLICATIONS

Angular and Peristrophic Holographic Multiplexing," Applied Optics, Oct. 10, 2009, vol. 45 (29), pp. 7661-7666.
Final Office Action dated Jan. 3, 2019 for U.S. Appl. No. 14/465,194, filed Aug. 21, 2014, 61 Pages.
Final Office Action dated Jan. 10, 2018 for U.S. Appl. No. 14/465,194, filed Aug. 21, 2014, 50 Pages.
Final Office Action dated Nov. 18, 2020 for U.S. Appl. No. 14/461,044, filed Aug. 15, 2014, 14 Pages.
Final Office Action dated Oct. 21, 2021 for U.S. Appl. No. 16/899,843, filed Jun. 12, 2020, 29 Pages.
Final Office Action dated Jul. 23, 2021 for U.S. Appl. No. 14/461,044, filed Aug. 15, 2014, 15 Pages.
Final Office Action received for U.S. Appl. No. 14/155,087 dated Dec. 16, 2016, 32 pages.
Final Office Action received for U.S. Appl. No. 14/155,087 dated Jul. 20, 2015, 27 pages.
Final Office Action received for U.S. Appl. No. 14/155,087 dated Jul. 8, 2016, 27 pages.
Final Office Action received for U.S. Appl. No. 14/155,087 dated Nov. 27, 2017, 40 pages.
Final Office Action received for U.S. Appl. No. 14/155,107 dated Dec. 19, 2016, 35 pages.
Final Office Action received for U.S. Appl. No. 14/155,107 dated Jan. 17, 2019, 46 pages.
Final Office Action received for U.S. Appl. No. 14/155, 107 dated Jul. 16, 2015, 28 pages.
Final Office Action received for U.S. Appl. No. 14/155, 107 dated Jul. 8, 2016, 31 pages.
Final Office Action received for U.S. Appl. No. 14/155, 107 dated Nov. 27, 2017, 44 pages.
First Office Action dated Nov. 25, 2020, for Canadian Application No. 2921954, filed Aug. 21, 2014, 4 pages.
Hainich R.R., et al., "Chapter 10: Near-Eye Displays," Displays: Fundamentals & Applications, AK Peters/CRC Press, 2011, 65 pages.
Hornstein S., et al., "Maradin's Micro-Mirror—System Level Synchronization Notes," SID Digest, 2012, pp. 981-984.
"IEEE 100 The Authoritative Dictionary of IEEE Standards Terms," Seventh Edition, Standards Information Network IEEE Press, Dec. 2000, 3 pages.
International Search Report and Written Opinion for International Application No. PCT/US2016/018293, dated Jun. 8, 2016, 17 Pages.
International Search Report and Written Opinion for International Application No. PCT/US2016/018298, dated Jun. 8, 2016, 14 Pages.
International Search Report and Written Opinion for International Application No. PCT/US2016/018299, dated Jun. 8, 2016, 12 Pages.
International Search Report and Written Opinion for International Application No. PCT/US2016/067246, dated Apr. 25, 2017, 10 Pages.
Itoh Y., et al., "Interaction-Free Calibration for Optical See-Through Head-Mounted Displays based on 3D Eye Localization," IEEE Symposium on 3D User Interfaces (3DUI), 2014, pp. 75-82.
Janssen C., "Radio Frequency (RF)," 2013, [Retrieved on Jul. 12, 2017], 2 pages, Retrieved from the Internet: URL: https://web.archive.org/web/20130726153946/https://www.techopedia.com/definition/5083/radio-frequency-rf.
Kessler D., "Optics of Near to Eye Displays (NEDs)," Presentation—Oasis, Tel Aviv, Feb. 19, 2013, 37 pages.
Krees B.C., et al., "Diffractive and Holographic Optics as Optical Combiners in Head Mounted Displays," UbiComp, Zurich, Switzerland, Sep. 8-12, 2013, pp. 1479-1482.
Kress B., et al., "A Review of Head-Mounted Displays (HMD) Technologies and Applications for Consumer Electronics," Proceedings of SPIE, 2013, vol. 8720, pp. 87200A-1-87200A-13.
Kress B., "Optical Architectures for See-Through Wearable Displays," Presentation, Bay Area SID Seminar, Apr. 30, 2014, 156 pages.
Lake et al., "Method and Apparatus for Analyzing Capacitive EMG and IMU Sensor Signals for Gesture Control," Amendment filed Aug. 21, 2015, for U.S. Appl. No. 14/186,878, 13 pages.
Lake et al., "Method and Apparatus for Analyzing Capacitive EMG and IMU Sensor Signals for Gesture Control," Office Action dated Jun. 17, 2015, for U.S. Appl. No. 14/186,878, 13 pages.
Lake et al.' "Method and Apparatus for Analyzing Capacitive EMG and IMU Sensor Signals for Gesture Control," Preliminary Amendment filed May 9, 2014, for U.S. Appl. No. 14/186,878, 9 pages.
Lake et al., "Method and Apparatus for Analyzing Capacitive EMG and IMU Sensor Signals for Gesture Control," U.S. Appl. No. 14/186,878, filed Feb. 21, 2014, 29 pages.
Lake et al., "Methods and Devices for Combining Muscle Activity Sensor Signals and Inertial Sensor Signals for Gesture-Based Control," Amendment filed Jan. 8, 2016, for U.S. Appl. No. 14/186,889, 16 pages.
Lake et al., "Methods and Devices for Combining Muscle Activity Sensor Signals and Inertial Sensor Signals for Gesture-Based Control," Amendment filed Jul. 13, 2016, for U.S. Appl. No. 14/186,889, 12 pages.
Lake et al., "Methods and Devices for Combining Muscle Activity Sensor Signals and Inertial Sensor Signals for Gesture-Based Control," Office Action dated Jun. 16, 2016, for U.S. Appl. No. 14/186,889, 13 pages.
Lake et al., "Methods and Devices for Combining Muscle Activity Sensor Signals and Inertial Sensor Signals for Gesture-Based Control," Office Action dated Nov. 5, 2015, for U.S. Appl. No. 14/186,889, 11 pages.
Lake et al., "Methods and Devices That Combine Muscle Activity Sensor Signals and Inertial Sensor Signals for Gesture-Based Control," U.S. Appl. No. 14/186,889, filed Feb. 21, 2014, 58 pages.
Levola T., "7.1: Invited Paper: Novel Diffractive Optical Components for Near to Eye Displays," SID Symposium Digest of Technical Papers, 2006, vol. 37 (1), pp. 64-67.
Liao C.D., et al., "The Evolution of MEMS Displays," IEEE Transactions on Industrial Electronics, Apr. 2009, vol. 56 (4), pp. 1057-1065.
Lippert T.M., "Chapter 6: Display Devices: RSD™ (Retinal Scanning Display)," The Avionics Handbook, CRC Press, 2001, 8 pages.
Majaranta P., et al., "Chapter 3: Eye Tracking and Eye-Based Human-Computer Interaction," Advances in Physiological Computing, Springer-Verlag London, 2014, pp. 39-65.
Merriam-Webster, "Radio Frequencies," download date Jul. 12, 2017, 2 pages, Retrieved from the Internet: URL: https://www.merriam-webster.com/table/collegiate/radiofre.htm.
Morun C., et al., "Systems, Articles, and Methods for Capacitive Electromyography Sensors," U.S. Appl. No. 16/437,351, filed Jun. 11, 2019, 51 pages.
Non-Final Office Action dated Mar. 1, 2018 for U.S. Appl. No. 14/553,657, filed Nov. 25, 2014, 29 Pages.
Non-Final Office Action dated May 2, 2018 for U.S. Appl. No. 15/799,628, filed Oct. 31, 2017, 25 Pages.
Non-Final Office Action dated Oct. 5, 2022 for U.S. Appl. No. 17/576,815, filed Jan. 14, 2022, 14 pages.
Non-Final Office Action dated Nov. 6, 2018 for U.S. Appl. No. 16/057,573, filed Aug. 7, 2018, 14 Pages.
Non-Final Office Action dated May 7, 2021 for U.S. Appl. No. 16/899,843, filed Jun. 12, 2020, 24 Pages.
Non-Final Office Action dated Oct. 7, 2022 for U.S. Appl. No. 17/141,646, filed Jan. 5, 2021, 6 pages.
Non-Final Office Action dated Sep. 11, 2019 for U.S. Appl. No. 14/465,194, filed Aug. 21, 2014, 72 Pages.
Non-Final Office Action dated May 12, 2022 for U.S. Appl. No. 16/899,843, filed Jun. 12, 2020, 34 Pages.
Non-Final Office Action dated Sep. 14, 2017 for U.S. Appl. No. 14/539,773, filed Nov. 12, 2014, 28 pages.
Non-Final Office Action dated Aug. 15, 2018 for U.S. Appl. No. 14/465,194, filed Aug. 21, 2014, 64 Pages.
Non-Final Office Action dated Jun. 15, 2020 for U.S. Appl. No. 16/292,609, filed Mar. 5, 2019, 26 Pages.

(56) References Cited

OTHER PUBLICATIONS

Non-Final Office Action dated Aug. 17, 2017 for U.S. Appl. No. 14/465,194, filed Aug. 21, 2014, 81 Pages.
Non-Final Office Action dated Dec. 17, 2018 for U.S. Appl. No. 16/137,960, filed Sep. 21, 2018, 10 pages.
Non-Final Office Action dated Jan. 18, 2018 for U.S. Appl. No. 15/799,621, filed Oct. 31, 2017, 10 pages.
Non-Final Office Action dated Jun. 22, 2017 for U.S. Appl. No. 14/461,044, filed Aug. 15, 2014, 21 Pages.
Non-Final Office Action dated Feb. 25, 2021 for U.S. Appl. No. 14/461,044, filed Aug. 15, 2014, 17 Pages.
Non-Final Office Action dated Aug. 28, 2018 for U.S. Appl. No. 16/023,276, filed Jun. 29, 2018, 10 pages.
Non-Final Office Action dated Aug. 28, 2018 for U.S. Appl. No. 16/023,300, filed Jun. 29, 2018, 11 pages.
Non-Final Office Action dated Jun. 28, 2021 for U.S. Appl. No. 16/550,905, filed Aug. 26, 2019, 5 Pages.
Non-Final Office Action received for U.S. Appl. No. 14/155,087 dated Aug. 16, 2016, 28 pages.
Non-Final Office Action received for U.S. Appl. No. 14/155,087 dated Aug. 7, 2017, 28 pages.
Non-Final Office Action received for U.S. Appl. No. 14/155,087 dated Feb. 17, 2016, 26 pages.
Non-Final Office Action received for U.S. Appl. No. 14/155,087 dated Mar. 31, 2015, 22 pages.
Non-Final Office Action received for U.S. Appl. No. 14/155,107 dated Aug. 17, 2016, 37 pages.
Non-Final Office Action received for U.S. Appl. No. 14/155,107 dated Aug. 7, 2017, 34 pages.
Non-Final Office Action received for U.S. Appl. No. 14/155,107 dated Feb. 11, 2016, 42 pages.
Non-Final Office Action received for U.S. Appl. No. 14/155, 107 dated Jul. 13, 2018, 45 pages.
Non-Final Office Action received for U.S. Appl. No. 14/155,107 dated Mar. 31, 2015, 26 pages.
Notice of Allowance dated May 1, 2019 for U.S. Appl. No. 16/137,960, filed Sep. 21, 2018, 14 pages.
Notice of Allowance dated Mar. 5, 2019 for U.S. Appl. No. 16/057,573, filed Aug. 7, 2018, 31 Pages.
Notice of Allowance dated Feb. 8, 2019 for U.S. Appl. No. 16/023,276, filed Jun. 29, 2018, 15 pages.
Notice of Allowance dated Mar. 11, 2020 for U.S. Appl. No. 14/465,194, filed Aug. 21, 2014, 29 Pages.
Notice of Allowance dated Jun. 15, 2018 for U.S. Appl. No. 15/799,621, filed Oct. 31, 2017, 27 pages.
Notice of Allowance dated Jul. 18, 2022 for U.S. Appl. No. 16/550,905, filed Aug. 26, 2019, 7 pages.
Notice of Allowance dated Apr. 20, 2022 for U.S. Appl. No. 14/461,044, filed Aug. 15, 2014, 08 pages.
Notice of Allowance dated Sep. 24, 2020 for U.S. Appl. No. 16/292,609, filed Mar. 5, 2019, 20 Pages.
Notice of Allowance dated Mar. 25, 2022 for U.S. Appl. No. 16/550,905, filed Aug. 26, 2019, 7 pages.
Notice of Allowance dated Sep. 25, 2018 for U.S. Appl. No. 14/553,657, filed Nov. 25, 2014, 25 Pages.
Notice of Allowance dated Jan. 28, 2019 for U.S. Appl. No. 16/023,300, filed Jun. 29, 2018, 31 pages.
Notice of Allowance dated Nov. 3, 2022 for U.S. Appl. No. 16/899,843, filed Jun. 12, 2020, 10 pages.
Notice of Allowance dated Mar. 30, 2018 for U.S. Appl. No. 14/539,773, filed Nov. 12, 2014, 17 pages.
Notice of Allowance dated Nov. 30, 2018 for U.S. Appl. No. 15/799,628, filed Oct. 31, 2017, 19 Pages.
Notice of Allowance received for U.S. Appl. No. 14/155,107 dated Aug. 30, 2019, 16 pages.

Office Action for European Application No. 19806723.3, dated Oct. 27, 2022, 8 pages.
Office Action dated Sep. 28, 2022 for Chinese Application No. 201780059093.7, filed Jul. 25, 2017, 16 pages.
Restriction Requirement dated Aug. 8, 2017 for U.S. Appl. No. 14/553,657, filed Nov. 25, 2014, 7 Pages.
Schowengerdt B.T., et al., "Stereoscopic Retinal Scanning Laser Display With Integrated Focus Cues for Ocular Accommodation," Proceedings of SPIE-IS&T Electronic Imaging, 2004, vol. 5291, pp. 366-376.
Silverman N.L., et al., "58.5L: Late-News Paper: Engineering a Retinal Scanning Laser Display with Integrated Accommodative Depth Cues," SID 03 Digest, 2003, pp. 1538-1541.
Takatsuka Y., et al., "Retinal Projection Display Using Diffractive Optical Element," Tenth International Conference on Intelligent Information Hiding and Multimedia Signal Processing, IEEE, 2014, pp. 403-406.
Urey H., "Diffractive Exit-Pupil Expander for Display Applications," Applied Optics, Nov. 10, 2001, vol. 40 (32), pp. 5840-5851.
Urey H., et al., "Optical Performance Requirements for MEMS-Scanner Based Microdisplays," Conferences on MOEMS and Miniaturized Systems, SPIE, 2000, vol. 4178, pp. 176-185.
Viirre E., et al., "The Virtual Retinal Display: A New Technology for Virtual Reality and Augmented Vision in Medicine," Proceedings of Medicine Meets Virtual Reality, IOS Press and Ohmsha, 1998, pp. 252-257.
Wijk U., et al., "Forearm Amputee's Views of Prosthesis Use and Sensory Feedback," Journal of Hand Therapy, Jul. 2015, vol. 28 (3), pp. 269-278.
Written Opinion for International Application No. PCT/US2014/057029, dated Feb. 24, 2015, 9 Pages.
Office Action dated Feb. 7, 2023 for European Application No. 19810524.9, filed May 28, 2019, 7 pages.
Notice of Allowance dated Dec. 14, 2022 for U.S. Appl. No. 15/882,858, filed Jan. 29, 2018, 10 pages.
Office Action dated Jan. 20, 2023 for Chinese Application No. 201780059093.7, filed Jul. 25, 2017, 16 pages.
European Search Report for European Patent Application No. 23186202.0, dated Aug. 2, 2023, 7 pages.
Khezri M., et al., "A Novel Approach to Recognize Hand Movements Via sEMG Patterns," 2007 Annual International Conference of the IEEE Engineering in Medicine and Biology Society, Aug. 22, 2007, pp. 4907-4910.
Naik G.R., et al., "SEMG for Identifying Hand Gestures using ICA," In Proceedings of the 2nd International Workshop on Biosignal Processing and Classification, Jan. 31, 2006, pp. 61-67.
Office Action dated Sep. 14, 2023 for Chinese Application No. 201980035465.1, filed May 28, 2019, 9 pages.
Office Action dated Aug. 15, 2023 for Japanese Patent Application No. 2021-507757, filed on Feb. 15, 2021, 9 pages.
Office Action dated Aug. 16, 2023 for Chinese Application No. 201880082887.X, filed Oct. 19, 2018, 17 pages.
Office Action dated Aug. 16, 2023 for Chinese Application No. 202080062417.4, filed Sep. 3, 2020, 11 pages.
Office Action dated Aug. 21, 2023 for Chinese Patent Application No. 201980062920.7, filed Sep. 20, 2019, 21 pages.
Office Action dated Jun. 22, 2023 for European Patent Application No. 19863248.1, filed on Sep. 20, 2019, 5 pages.
Office Action dated Aug. 29, 2023 for Japanese Application No. 2021-506985, filed Feb. 9, 2021, 6 pages.
Office Action dated Aug. 31, 2023 for Chinese Application No. 201980045972.3, filed May 7, 2021, 20 pages.
Valero-Cuevas F. J., et al. "Computational Models for Neuromuscular Function," IEEE reviews in Biomedical Engineering, Dec. 31, 2009, vol. 2, pp. 110-135.

* cited by examiner

ELECTROMAGNETIC INTERFERENCE REDUCTION IN EXTENDED REALITY ENVIRONMENTS

CROSS REFERENCE TO RELATED APPLICATION

This application claims the benefit of U.S. Provisional Application No. 62/826,574, filed Mar. 29, 2019, the disclosure of which is incorporated, in its entirety, by this reference.

BRIEF DESCRIPTION OF THE DRAWINGS

The accompanying drawings illustrate a number of exemplary embodiments and are a part of the specification. Together with the following description, these drawings demonstrate and explain various principles of the present disclosure.

FIG. 3A illustrates a schematic of a control device of the computer-based system and FIG. 3B illustrates an example dongle portion that may be connected to a computer, where the dongle portion is configured to communicate with the control device (and a similar configuration may be used within a head-mounted device in communication with the control device).

FIG. 6A illustrates a first configuration in which an anti-aliasing filter is positioned away from an analog-to-digital converter, and FIG. 6B illustrates a second configuration in which the anti-aliasing filter is located proximate to the analog-to-digital converter.

FIG. 8A shows a power spectrum of a first channel and FIG. 8B shows a power spectrum of a second channel of a 16-channel EMG control interface.

FIG. 8C shows a power spectrum of the same channel as FIG. 8A, and FIG. 8D shows a power spectrum of the same channel as FIG. 8B.

Figure 1A:
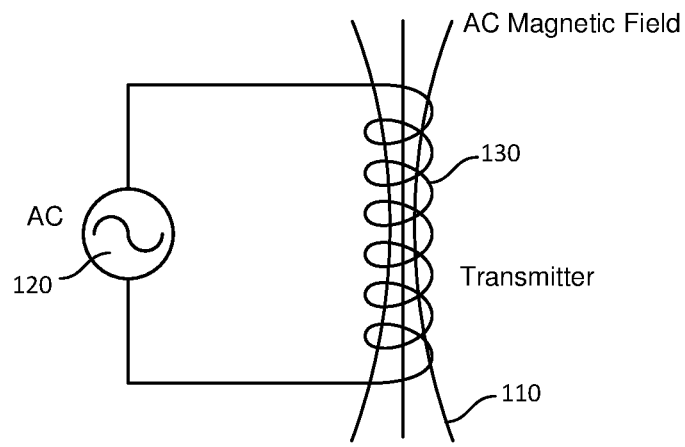
FIGS. 1A-1C illustrate, respectively, how an AC magnetic field is generated in a magnetic tracking system transmitter, how the generated AC magnetic field induces a current in a closed-loop conductor, and how the generated AC magnetic field induces a voltage in an open-loop conductor.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and are described in detail herein. However, the exemplary embodiments described herein are not intended to be limited to the particular forms disclosed. Rather, the present disclosure covers all modifications, equivalents, and alternatives falling within the scope of the appended claims.

DETAILED DESCRIPTION OF EXEMPLARY EMBODIMENTS

Extended reality systems, such as augmented reality or virtual reality systems, often include one or more sensors configured to detect the actions or intent of a user. Such sensors may be included in a control device, such as a wearable device configured to be worn by the user. For example, a wearable control device may include a plurality of electromyography (EMG) sensors that include electrodes designed to contact the skin of a user when the device is worn. EMG signals generated by these EMG sensors may, in turn, be used to generate a control signal that may be used to modify the extended reality experience of the user. However, these EMG signals are often susceptible to noise, such as electromagnetic noise generated by an electronic circuit of the control device and/or other components (such as magnetic trackers). Unfortunately, these noise signals often have undesirable effects on the control signal and, hence, on the extended reality experience of the user.

As is explained in greater detail below, the instant disclosure describes a variety of approaches to reducing or substantially eliminating the effects of noise, from any source, on detected sensor signals. For example, a control device according to the principles described herein may include an analog circuit with an amplifier configured to receive sensor signals from a plurality of electrodes, an analog-to-digital converter (ADC) configured to receive analog sensor signals from the analog circuit and to provide digital sensor signals, and a processor configured to receive the digital sensor signals and provide digital control signals based on the sensor signals.

In some examples, the control device may be configured to reduce the effects of electromagnetic noise. For example, the amplifier and/or the ADC may be configured to reduce noise signals, and an anti-aliasing filter may also be introduced into the analog circuit to prevent problematic under-sampling of the noise signal. The control device may also be shielded, and the arrangement of components within the control device may be configured to reduce the amplitude of the noise signal. Improved control signals may then be generated by the control device, allowing improved control of an extended reality view in response to the control signals.

FIG. 1A illustrates generation of a magnetic field 110 by passing AC current from a current source 120 through coil 130. In some examples, the coil 130 may be a component of the transmitter of a magnetic tracker.

Figure 1B:
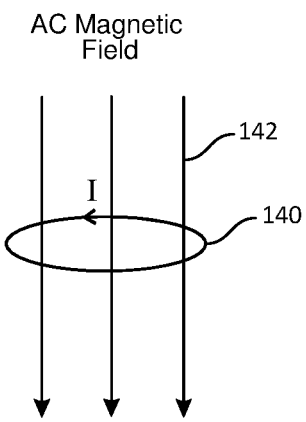

FIG. 1B illustrates that an alternating magnetic field 142 (that may be generated by the transmitter of a magnetic tracker) may induce a current (denoted I) in a closed-loop conductor 140. The current I may be an alternating current, so the arrow direction may be arbitrary. This may create noise problems, particularly when the closed-loop conductor is located near the transmitter.

Figure 1C:
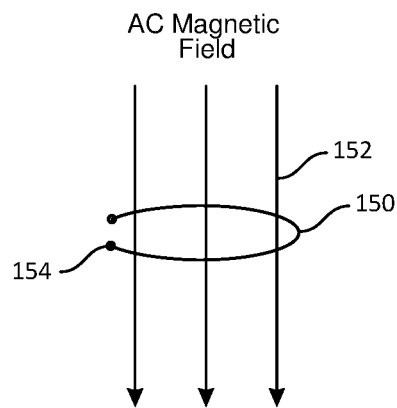

FIG. 1C illustrates that the alternating magnetic field 152 (that may be generated by the transmitter of a magnetic tracker) may induce an alternating voltage in an open-loop conductor 150. A noise voltage may be generated between the open ends of the open-loop conductor (e.g., end 154). This may also create noise problems, particularly when the open-loop conductor is located near the transmitter. In general, an open-loop or closed-loop conductor located close to the magnetic tracker transmitter may result in a noise signal (a noise voltage and/or a noise current) being induced in the conductor.

Figure 2A:
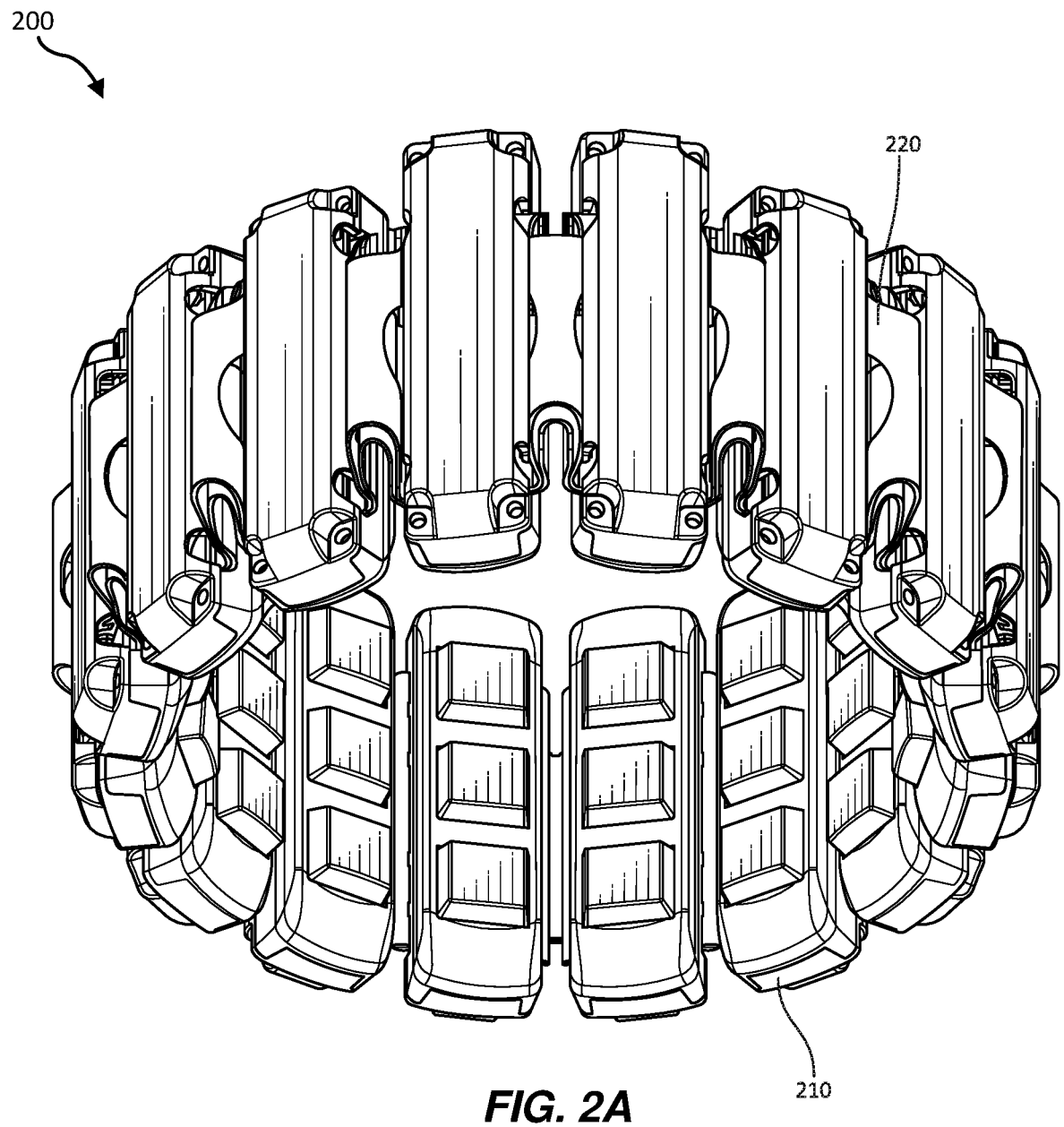
FIG. 2A illustrates a wearable system with sixteen EMG sensors arranged circumferentially around an elastic band configured to be worn around a user's lower arm or wrist, in accordance with some embodiments.

FIG. 2A illustrates an example device, that may include one or more of the following: a human-machine interface, an interface device, a control device, and/or a control interface. In this example, the device may include a control device 200, which in this example includes sixteen neuromuscular sensors 210 (e.g., EMG sensors) arranged circumferentially around an elastic band 220 configured to be worn around a user's lower arm or wrist. As shown, EMG sensors 210 are arranged circumferentially around elastic band 220. Any suitable number of neuromuscular sensors may be used. The number and arrangement of neuromuscular sensors may depend on the particular application for which the control device is used. For example, a wearable control device configured as an armband, wristband, or chest-band may be used to generate control information for controlling an augmented reality system, controlling a robot, controlling a vehicle, scrolling through text, controlling a virtual avatar, or any other suitable control task. As shown, the sensors may be coupled together using flexible electronics incorporated into the wireless device.

Figure 2B:
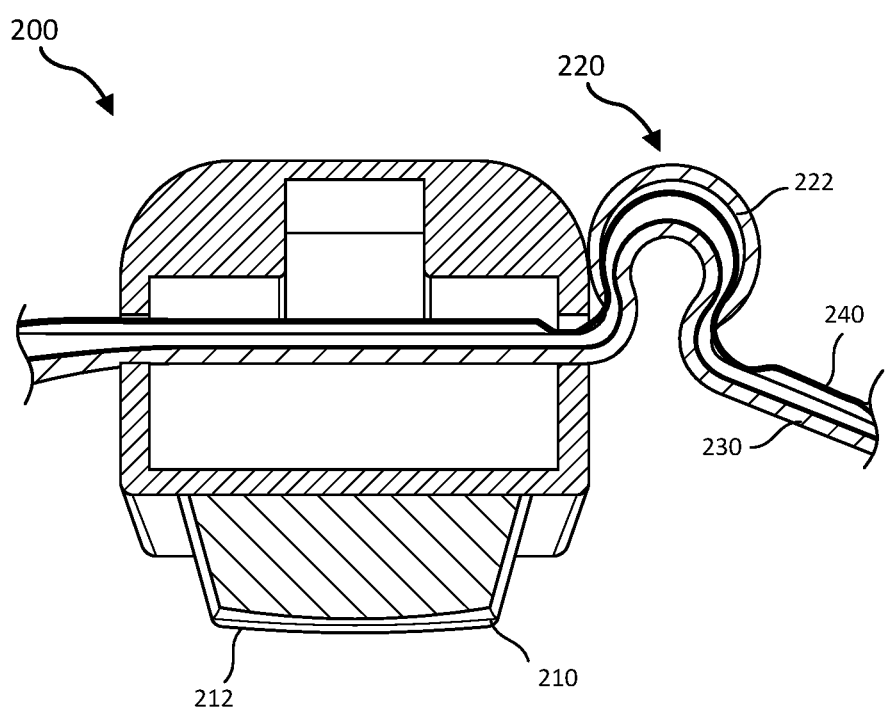
FIG. 2B is a cross-sectional view through one of the sixteen EMG sensors illustrated in FIG. 2A.

FIG. 2B illustrates a cross-sectional view through one of the sensors 210 of the control device 200 shown in FIG. 2A. The sensor 210 may include a plurality of electrodes located within a skin-contacting surface 212. The elastic band 220 may include an outer flexible layer 222 and an inner flexible layer 230, that may at least in part enclose a flexible electrical connector 240 which may interconnect the sensors.

In some embodiments, the output of one or more of the sensing components may be optionally processed using hardware signal processing circuit (e.g., to perform amplification, filtering, and/or rectification). In some embodiments, at least some signal processing of the output of the sensing components may be performed in software. Thus, signal processing of signals sampled by the sensors may be performed in hardware, software, or by any suitable combination of hardware and software, as aspects of the technology described herein are not limited in this respect. A non-limiting example of a signal processing chain used to process sensor data from sensors 210 is discussed in more detail below, for example, with reference to FIGS. 3A and 3B.

Figure 3A:
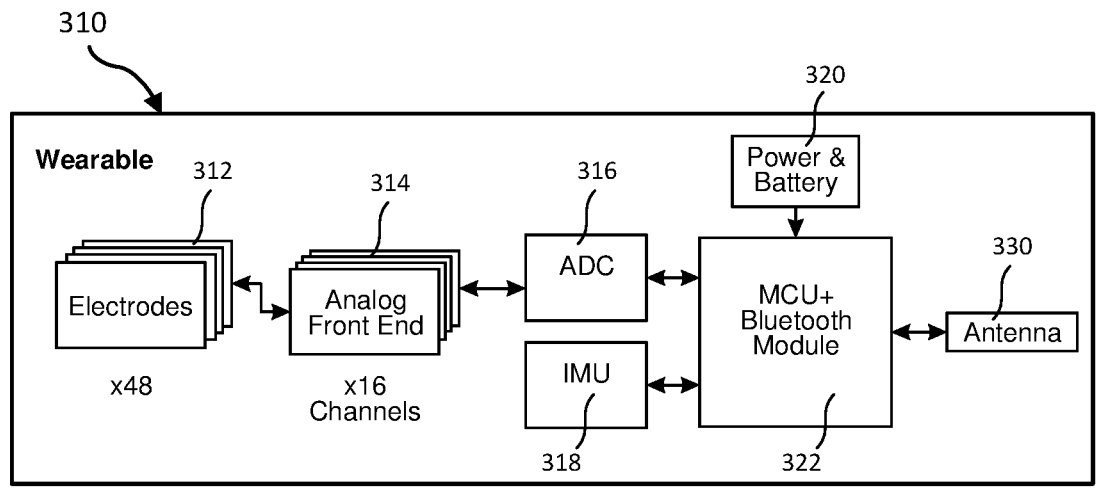
FIGS. 3A and 3B schematically illustrate components of a computer-based system on which some embodiments are implemented.
Figure 3B:
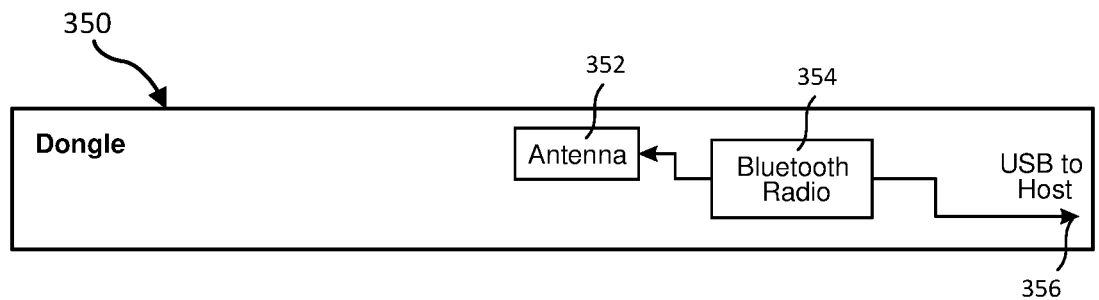

FIGS. 3A and 3B illustrate a schematic diagram with internal components of an apparatus including EMG sensors. In some examples, there may be sixteen EMG sensors, though this and other numerical examples are non-limiting and other numbers of sensors may be used. The apparatus may include a control device 310 (FIG. 3A) and a dongle portion 350 (FIG. 3B) in communication with the control device 310 (e.g., via BLUETOOTH or another suitable short range wireless communication technology). In some examples, the function of the dongle portion may be included within a head-mounted device, allowing the control device to communicate with the head-mounted device.

FIG. 3A shows that the control device 310 may include a plurality of sensors 312, that may include the example EMG sensors 210 described in connection with FIGS. 2A and 2B, or other sensors. The sensor signals from the sensors 312 may be provided to analog front end 314, that may be configured to perform analog processing (e.g., noise reduction, filtering, etc.) of the sensor signals. The processed analog signals may then be provided to analog-to-digital converter 316, which converts the processed analog signals to digital signals that may be processed by one or more computer processors. An example computer processor, that may be used in accordance with some embodiments, is microcontroller (MCU) 322. The MCU may also receive signals from other sensors (e.g., an inertial sensor such as inertial measurement unit (IMU) sensor 318, or other suitable sensors). The control device 310 may also include, or receive power from, a power supply 320, that may include a battery module or other power source. The output of the processing performed by MCU 322 may be provided to antenna 330 for transmission to the dongle portion 350 shown in FIG. 3B, or to another device such as a head-mounted device.

FIG. 3B shows an example dongle portion 350 that may include an antenna 352, that may be configured to communicate with antenna 330 associated with control device 310. Communication between antennas 330 and 352 may occur using any suitable wireless technology and protocol, non-limiting examples of which include radiofrequency signaling and BLUETOOTH. As shown, the signals received by antenna 352 of dongle portion 350 may be received by a BLUETOOTH radio (or other receiver circuit), and provided to a host computer through output 356 (e.g., a USB output) for further processing, display, and/or for effecting control of a particular physical or virtual object or objects.

In some examples, the dongle may be inserted into a separate computer device, that may be located within the same environment as the user, but not carried by the user. This separate computer may receive signals from the control device and further process these signals to provide control signals to the head-mounted device. In some examples, the dongle may be network enabled, allowing communication with a remote computer through the network, and the remote computer may provide control signals to the head-mounted device to modify an extended reality (XR) image (e.g., VR or AR image) presented to the user. In some examples, a dongle may be inserted into a head-mounted device to provide improved communications functionality, and the head-mounted device may perform further processing (e.g., modification of the XR image) based on the control signal received from the control device 310.

In some examples, an apparatus may not include a separate dongle portion. The configuration of the dongle portion may be included in a head-mounted device, such as an extended reality headset, or other device such as a remote computer device. In some examples, the circuit described above in FIG. 3B may be provided by (e.g., integrated within) components of the head-mounted device. In some examples, the control device may communicate with the head-mounted device using the described wireless communications, and/or a similar schematic circuit, or a circuit having similar functionality.

A head-mounted device may include an antenna similar to antenna 352 described above in relation to FIG. 3B. The antenna of a head-mounted device may be configured to communicate with the antenna associated with the control device. Communication between antennas of the control device and the head-mounted device may occur using any suitable wireless technology and protocol, non-limiting examples of which include radiofrequency signaling and BLUETOOTH. Signals, such as control signals, received by an antenna of a head-mounted device may be received by a BLUETOOTH radio (or other receiver circuit) and provided to a processor within the head-mounted device, that may be programmed to modify an extended reality view for the user in response to the control signals.

Although the examples provided with reference to FIGS. 2A, 2B and FIGS. 3A, 3B are discussed in the context of interfaces with EMG sensors, techniques described herein for reducing electromagnetic interference may also be implemented in wearable interfaces with other types of sensors including, but not limited to, mechanomyography (MMG) sensors, sonomyography (SMG) sensors, and electrical impedance tomography (EIT) sensors.

In some examples, electromagnetic interference may be reduced by increasing the distance between a device and its associated analog circuit and a magnetic tracker transmitter that generates an AC magnetic field. In some embodiments, a shielding material may be arranged around at least a portion of the analog circuit to shield the circuit, at least in part, from the effects of the AC magnetic field. In yet further embodiments, one or more components of the analog circuit of the EMG control device may be configured to reduce electromagnetic interference induced on one or more conductors of the EMG control device. One or more of the various techniques for reducing electromagnetic interference described herein may be used alone or in combination.

Figure 4:
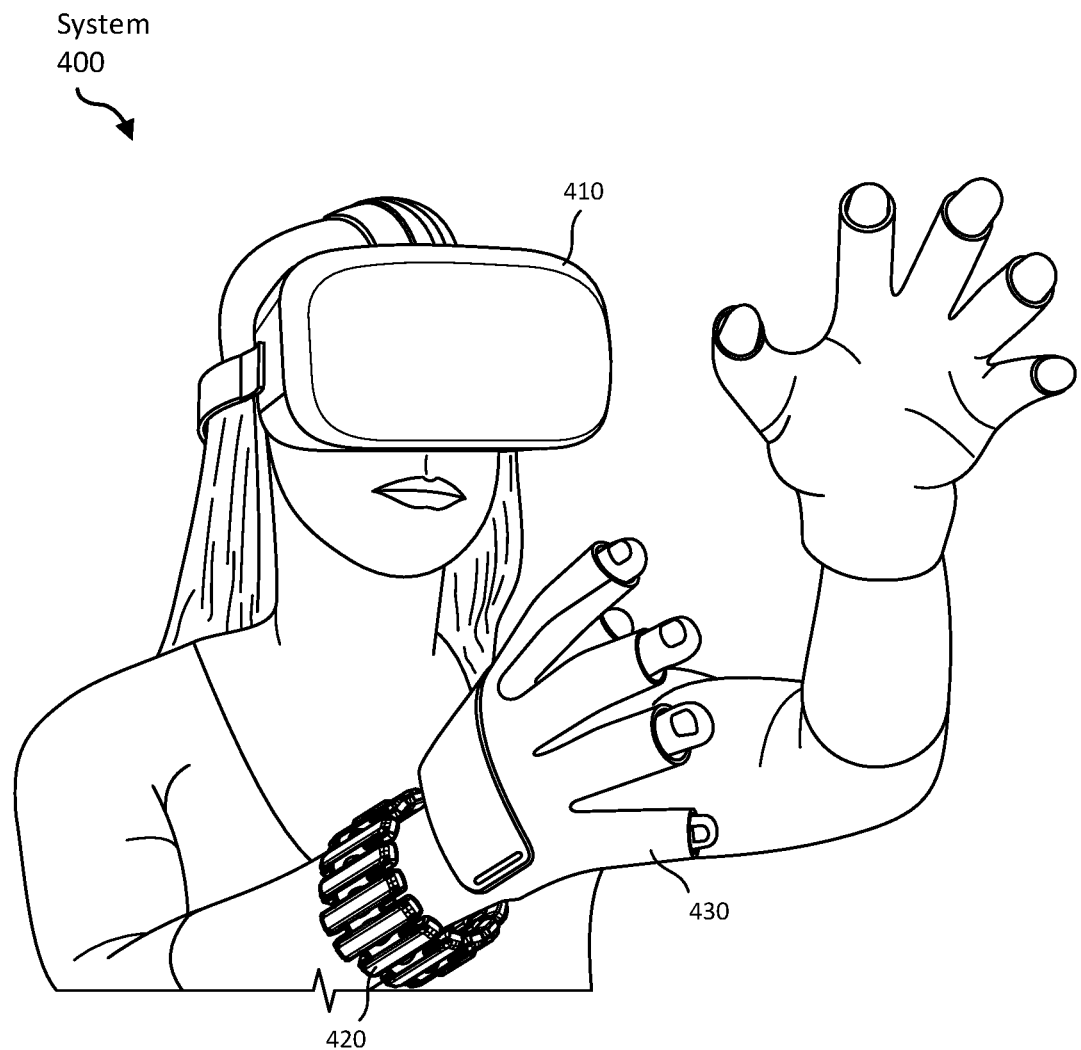
FIG. 4 illustrates components of an extended reality system, in accordance with some embodiments.

FIG. 4 illustrates an example XR system 400, such as an augmented reality system or virtual reality system, that may include a headset 410 and a control device 420 (that may represent a wearable control device). In some examples, the system 400 may include a magnetic tracker. In some examples, the transmitter for the magnetic tracker may be associated with (e.g., mounted on or in) the control device 420, and the receiver for the magnetic tracker may be mounted on the headset 410. In some examples, the transmitter for the magnetic tracker may be associated with (e.g., mounted on or in) the headset, or otherwise located within the environment. In some embodiments, the system 400 may also include one or more optional control gloves 430. In some examples, many or all functions of a control glove may be provided by the control device 420. In some examples, the control glove 430 may include a plurality of magnetic tracker receivers. The orientation and/or location of various parts of the hand of a user may be determined using magnetic tracker receivers, or other sensors.

In some examples, the control glove 430 (that may be more simply referred to as a glove) may include one or more magnetic tracker receivers. For example, a finger of the glove may include at least one receiver coil, and detection of a tracker signal from the at least one receiver coil induced by a magnetic tracker transmitter may be used to determine the position and/or orientation of at least portion of the finger. One or more receiver coils may be associated with each portion of a hand, such as a finger (such as the thumb), palm, and the like. The glove may also include other sensors providing sensor signals indicative of the position and/or configuration of the hand, such as electroactive sensors. Sensor signals, such as magnetic tracker receiver signals, may be transmitted to a control device, such as a wearable control device. In some examples, a control device (such as a wrist-mounted control device) may be in communication with a control glove, and receive sensor data from the control glove using wired and/or wireless communication. For example, a flexible electrical connector may extend between a control device (e.g., a wrist-mounted control device) and the glove.

In some examples, the control device 420 may include an EMG control interface similar to the device illustrated in FIGS. 2A-2B. Locating the magnetic tracker transmitter on or near the control device 420 may result in the introduction of noise into the signals recorded by the control device 420 due to induced currents and/or voltages. In some embodiments, electromagnetic interference caused by the magnetic tracker transmitter may be reduced by locating the transmitter at a distance further away from the control device 420. For example, the transmitter may be mounted on the headset 410, and the magnetic tracker receiver may be mounted on the control device 420. This configuration works well, for example, when the user keeps their arms away from their head, but may not work as well if the user moves their arms in close proximity to the headset. However, many XR applications do not require extensive proximity between the head and the hands of the user.

Electromagnetic interference reduction techniques may be integrated with magnetic trackers having configurations similar to the configuration shown in FIG. 4, or other configurations, such as configurations in which the magnetic tracker transmitter is positioned in a computer device separate from the headset 410 shown in FIG. 4, or at another remote locations, such as located within the same room as the user.

In some examples, electromagnetic interference may be reduced by increasing the physical distance between the magnetic tracker transmitter and the EMG control interface. In some embodiments, electromagnetic noise induced in the circuit of the EMG control interface may be reduced, at least in part, prior to analog-to-digital conversion using additional circuit components introduced in the analog signal chain. Although introducing additional circuit components into the analog signal chain increases the amount of area that the analog signal chain circuit consumes on a printed circuit broad, in some embodiments, the increase in area is offset by noise reduction benefits, such as those described in more detail below.

Figure 5:
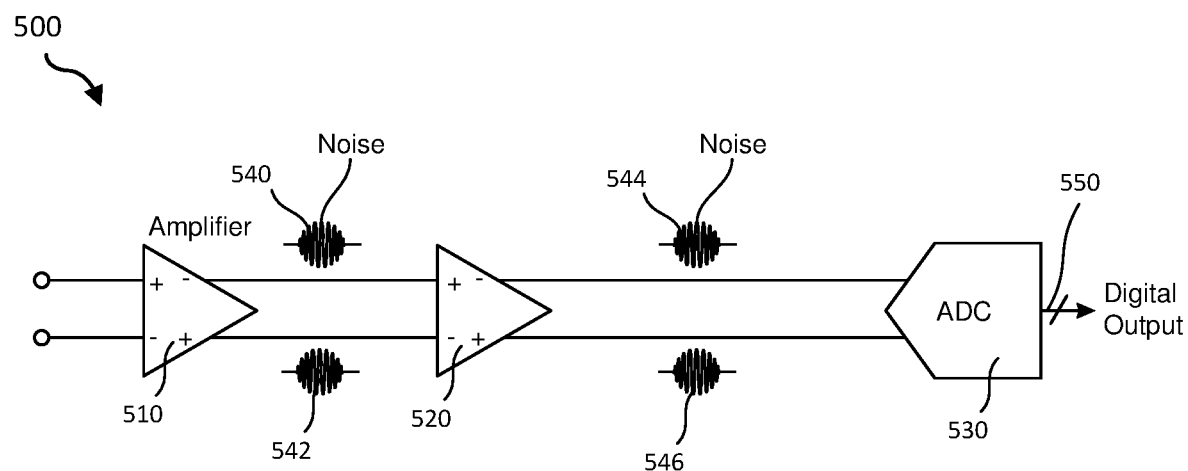
FIG. 5 illustrates a fully differential analog circuit in accordance with some embodiments.

FIG. 5 illustrates a portion of a device 500, including an electromagnetic interference reduction circuit in which the analog circuit of the device (e.g., the input analog signal chain of device, such as an EMG control interface) may include one or more fully differential amplifiers. As shown, the analog circuit may include a first fully differential amplifier stage 510 that receives a differential input signal from the sensors (such as EMG sensors, described in relation to FIG. 2) and a second fully differential amplifier stage 520 coupled to the output of the first fully differential amplifier stage 510, which provides a signal to the ADC (analog to digital converter) 530. In such a configuration, electromagnetic noise induced within the analog circuit is reduced due to subtraction of the differential signals at the output of each of the fully differential amplifier stages. The first fully differential amplifier 510 may be configured to cancel common mode noise signals in the sensor data. In this context, the term "cancel" may refer to subtraction of a signal from a similar signal (or vice versa) to give an approximately null result. Various noise signals may arise from a similar source (such as the transmitter signal), and hence may have similar amplitudes and phases, and may be canceled using subtraction of one signal from another. In some examples, noise signals 540 and 542, that may be induced by the transmitter signal within circuit traces (e.g., PCB tracks) may effectively cancel each other out due to the operation of the fully differential amplifier 520. The ADC 530 (which may be a differential ADC) is coupled to the output of the fully differential amplifier 520, and may be configured to subtract the noise signal from both input connections provided as input to the ADC (e.g., noise signals 544 and 546). This may be achieved, for example, by digitizing the difference signal between the two inputs. The ADC 530 may thereafter convert the noise-reduced signal into a digital representation. Hence, the ADC may be configured to effectively cancel out the noise signals 544 and 546 so that the output 550 has a reduced noise component.

In some examples, the ADC 530 may be a differential ADC, configured to output a digital signal based on the difference between two analog input voltages. If there is similar noise signal in both analog input voltages, the difference between the input voltages, and hence the digital signal, may be generally independent of the electromagnetic noise. For example, noise signals 544 and 546 may be present in both ADC inputs, and may have reduced or effectively no effect on the output of ADC 530 functioning as a differential ADC. In some examples, two digital signals may be generated, and digital subtraction (or division, or other comparison method) may be used to remove common mode noise signals. Alternatively, a difference signal may be generated and digitized. In this context, a common mode noise signal may refer to similar noise signals present in multiple sensor signals, or data channels derived therefrom.

In some examples, a device may include an analog circuit configured so that a first noise signal present at the non-inverting input of a differential amplifier may be similar to, and in phase with, a second noise signal generated at the inverting input of the differential amplifier. The differential amplifier may then effectively subtract the second noise signal from the first noise signal, so that the differential amplifier output may be effectively noise free, or have reduced noise in the differential amplifier output (e.g., compared to the output of a non-differential amplifier used in a similar circuit). In some examples, a device may include one or more fully differential amplifiers, where the difference between the two output voltages may be based on the difference between the two input voltages (optionally including multiplication by the gain, if any). For both differential amplifiers and fully differential amplifiers, the noise signal may be a common mode signal, having a similar form in both inputs, that is thereby greatly reduced or substantially eliminated in the output voltage(s). In some examples, negative feedback may be provided to reduce the gain and/or improve the signal bandwidth.

Figure 6A:
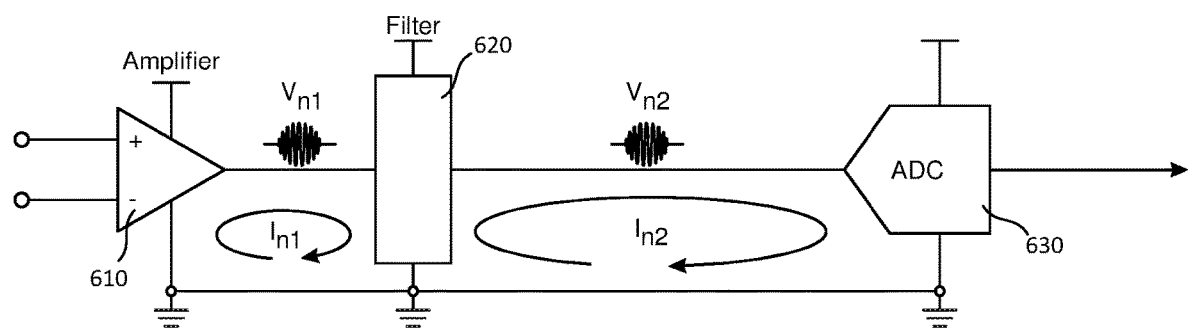
FIGS. 6A and 6B illustrate an analog circuit for filtering electromagnetic noise induced by an electromagnetic field in accordance with some embodiments.
Figure 6B:
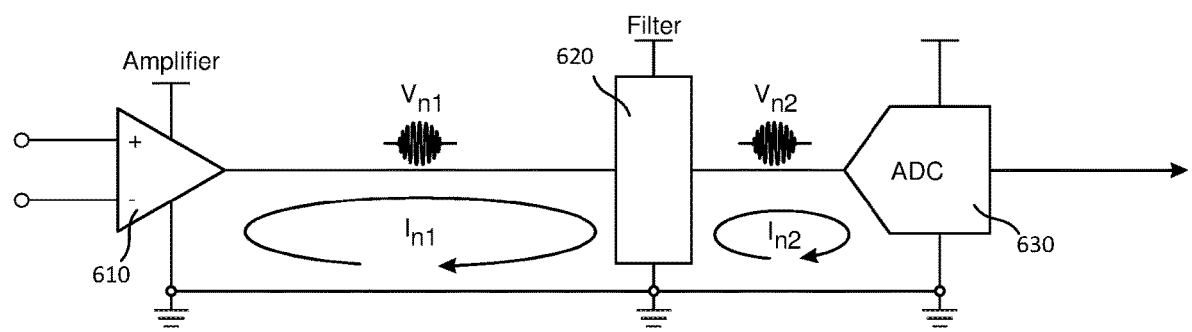

FIGS. 6A and 6B illustrate an example in which an anti-aliasing filter is included in the analog circuit (e.g., the EMG control interface) of an example control device. As shown in both FIGS. 6A and 6B, amplifier 610 may receive a differential signal from one or more sensors, such as one or more EMG sensors. Anti-aliasing filter 620 may be located between the output of amplifier 610 and the ADC 630, and may be configured to filter noise on the trace (e.g., a PCB conducting track or other electrical conductor) between the output of the amplifier 610 and the ADC 630. The configuration shown in FIG. 6A may experience a larger induced noise voltage ($V_{n2}$) and noise current ($I_{n2}$) between the anti-aliasing filter 620 and the ADC 630, compared to the induced noise voltage ($V_{n1}$) and noise current ($I_{n1}$) generated between the amplifier 610 and the anti-aliasing filter 620 (e.g., $V_{n2} > V_{n1}$, and $I_{n2} > I_{n1}$).

FIG. 6B shows a configuration in which the anti-aliasing filter 620 is located close to the ADC 630, such that the induced noise voltage and noise currents observed at the input to the ADC 630 are reduced compared to the configuration in FIG. 6A. For example, in the configuration of FIG. 6B, the following relationships may be observed; $V_{n1} > V_{n2}$, and $I_{n1} > I_{n2}$. The longer the trace between the anti-aliasing filter 620 and the ADC 630, the larger the resulting induced noise voltage/current may be introduced at the input of the ADC. Noise signals may be reduced by locating the anti-aliasing filter close to the ADC, thereby reducing the conducting track length between the output of the anti-aliasing filter and the ADC. In some examples, the electrically conducting path between the output of the anti-aliasing filter and the input of the ADC may be less than approximately 15 mm, such as less than approximately 10 mm. In some examples, the electrical conductor between the filter 620 and the ADC 630 may be shielded, for example using an electrically conducting and/or magnetically shielding layer or other suitable structure.

In some examples, the ADC and anti-aliasing filter may be integrated into a single package, for example, a single integrated circuit (IC, or chip). Shielding may be located proximate, adjacent, or within the ADC/anti-aliasing chip to reduce noise generation in the chip.

Figure 7A:
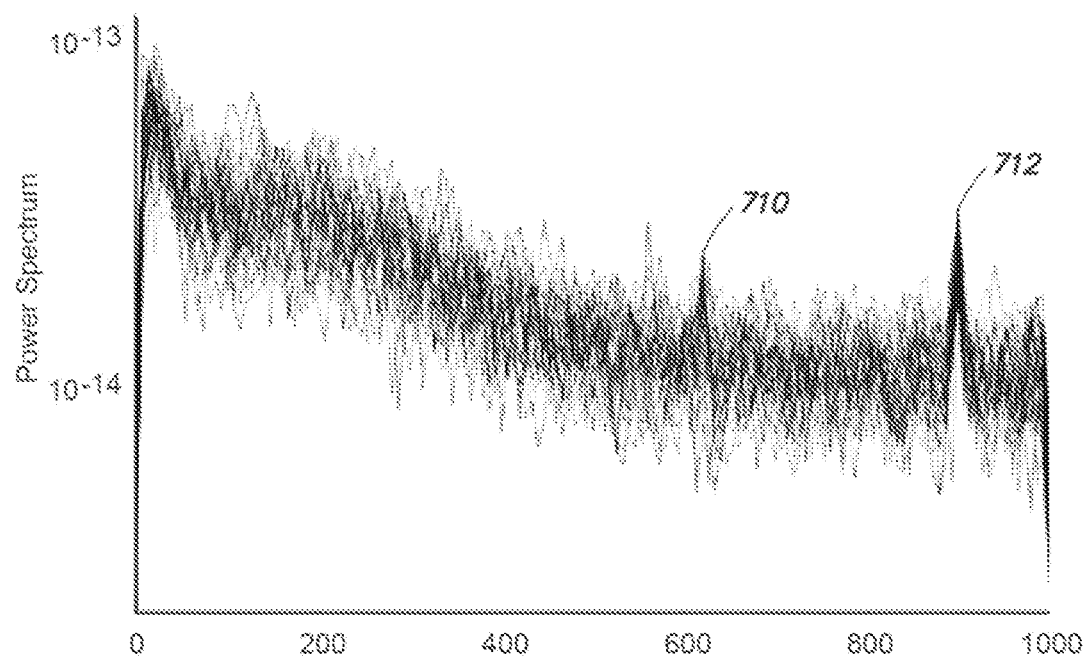
FIGS. 7A and 7B illustrate results of an experiment in which the configuration of FIG. 6A was used.
Figure 7B:
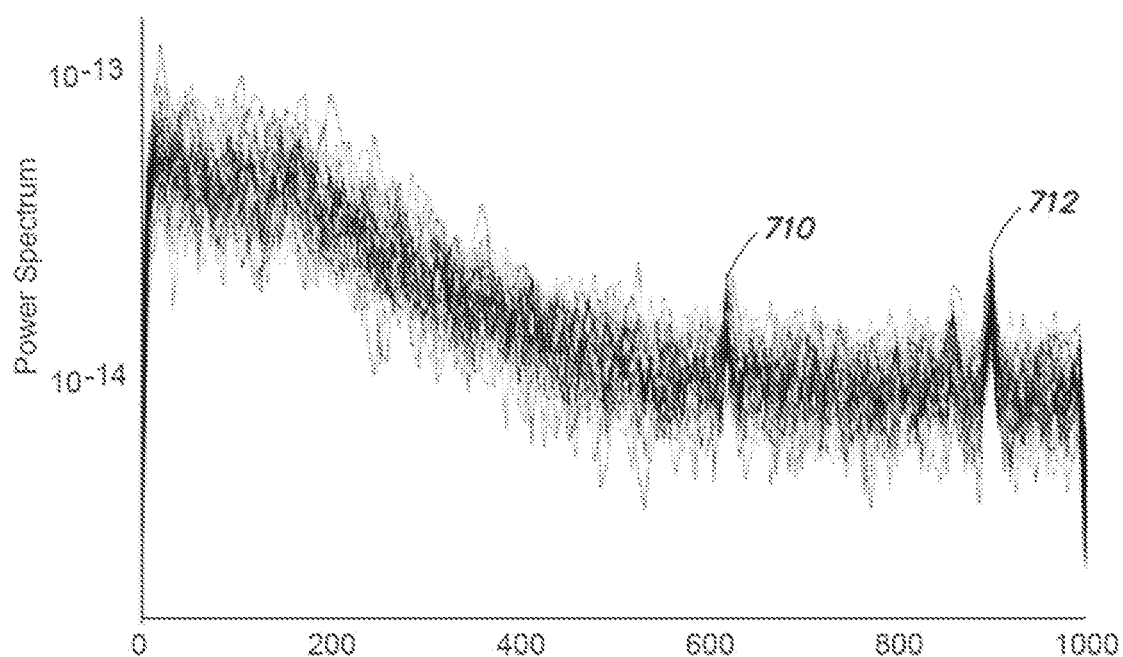
Figure 7C:
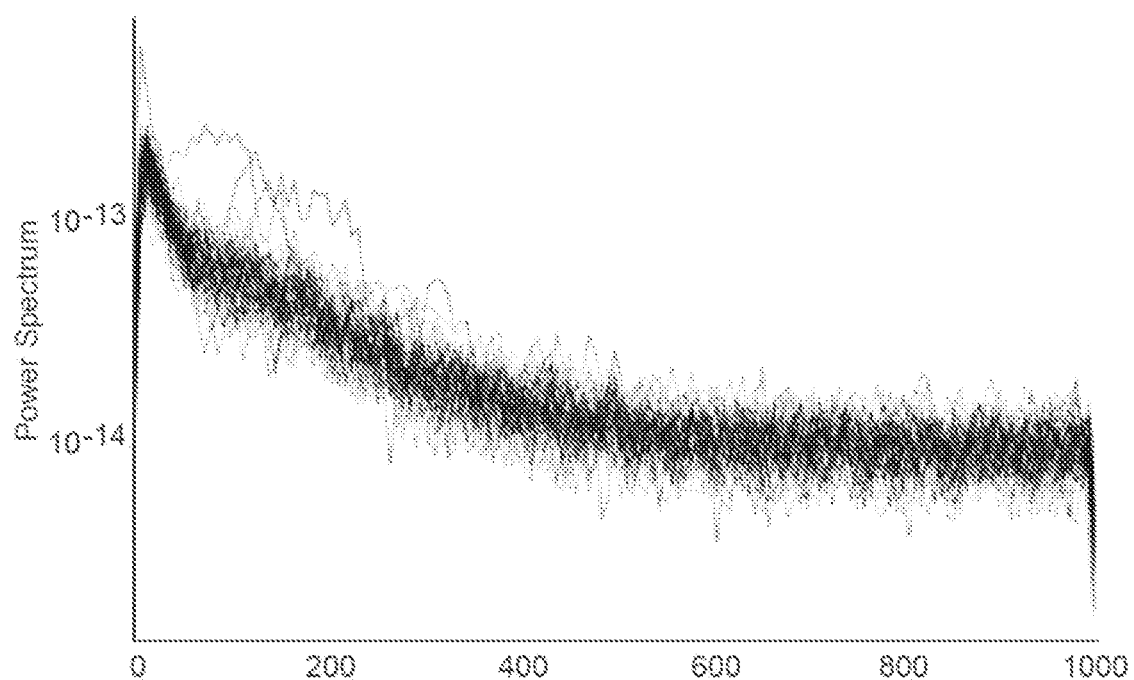
FIG. 7C illustrates results of an experiment in which the configuration of FIG. 6B was used, showing removal of noise peaks previously observable in a power spectrum for the first channel.

FIGS. 7A-C illustrate results from an experiment in which the effects of locating the anti-aliasing filter closer to (as shown in FIG. 6B) or farther from (as shown in FIG. 6A) the ADC were observed. FIGS. 7A and 7B show the power spectrum for two channels of a 16 channel EMG control interface when the anti-aliasing filter was located a distance of 24 cm from the ADC of the EMG control interface. Two noise peaks 710 and 712 may be observed at approximately 600 Hz and 900 Hz in both channels.

FIG. 7C shows results for the first channel of the 16-channel EMG control interface, when the anti-aliasing filter was located a distance of 1.5 cm from the ADC of the EMG control interface. The noise peaks previously observable in FIG. 7A are attenuated, and may no longer be observable when the distance between the anti-aliasing filter and the input of the ADC is reduced. A similar improvement was seen for the second channel, where the noise peaks previously observable in FIG. 7B were no longer visible when the anti-aliasing filter was located closer to the ADC. The x-axis unit is frequency in Hz.

In some embodiments, attenuation of noise generated by an external electromagnetic source may be achieved using a higher-order anti-aliasing filter arranged between an input amplifier and an ADC within an analog-signal chain of an EMG control interface. The higher-order anti-aliasing filter may, for example, in combination with the amplifier, provide a transfer function such that the amplified in-band signals are at least 90 dB higher than the attenuated noise signals.

Figure 8A:
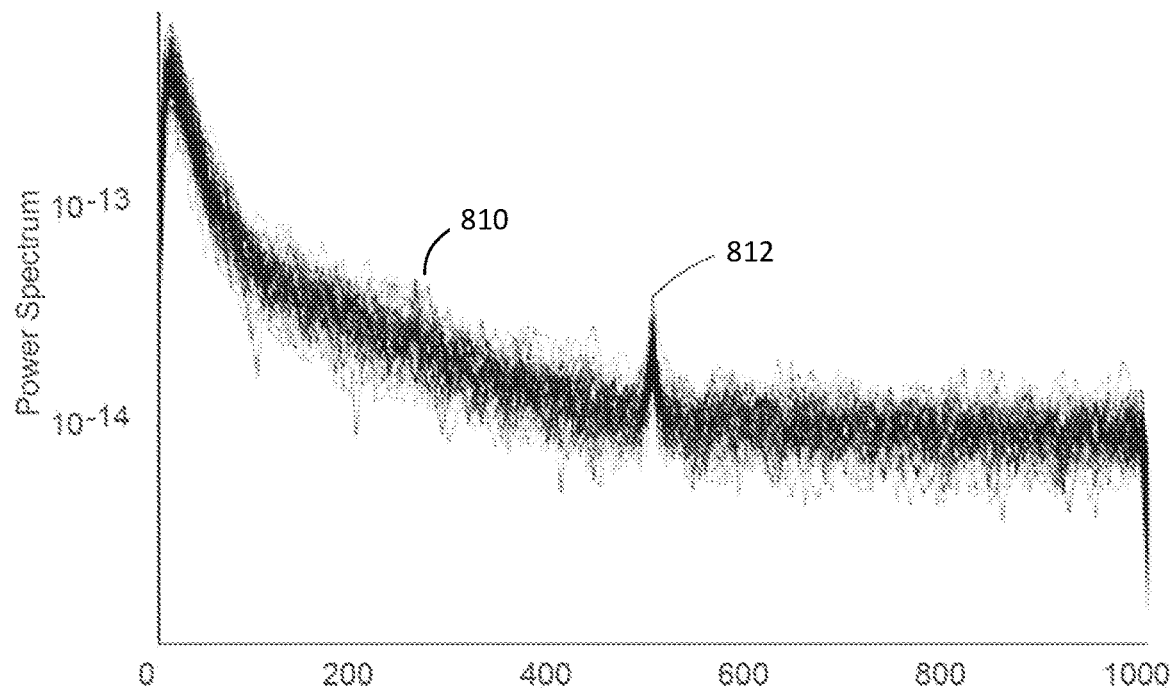
FIGS. 8A and 8B illustrate results of an experiment in which the configuration of FIG. 6B was used with a single anti-aliasing filter, where
Figure 8B:
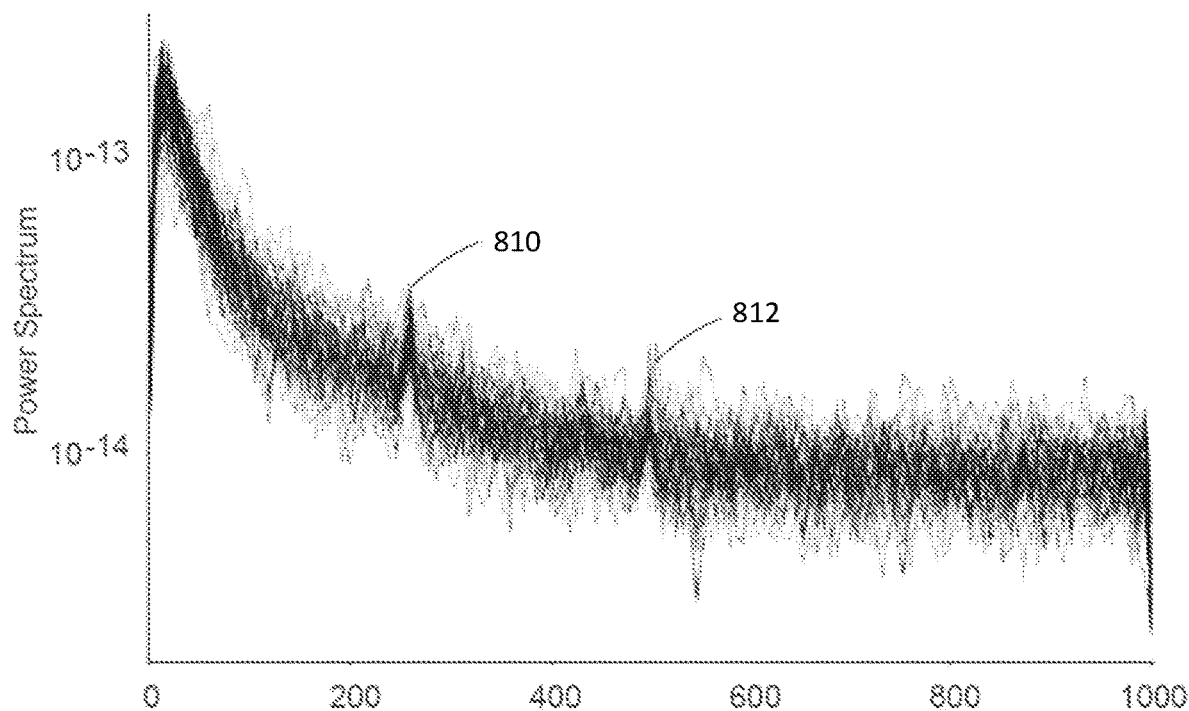
Figure 8C:
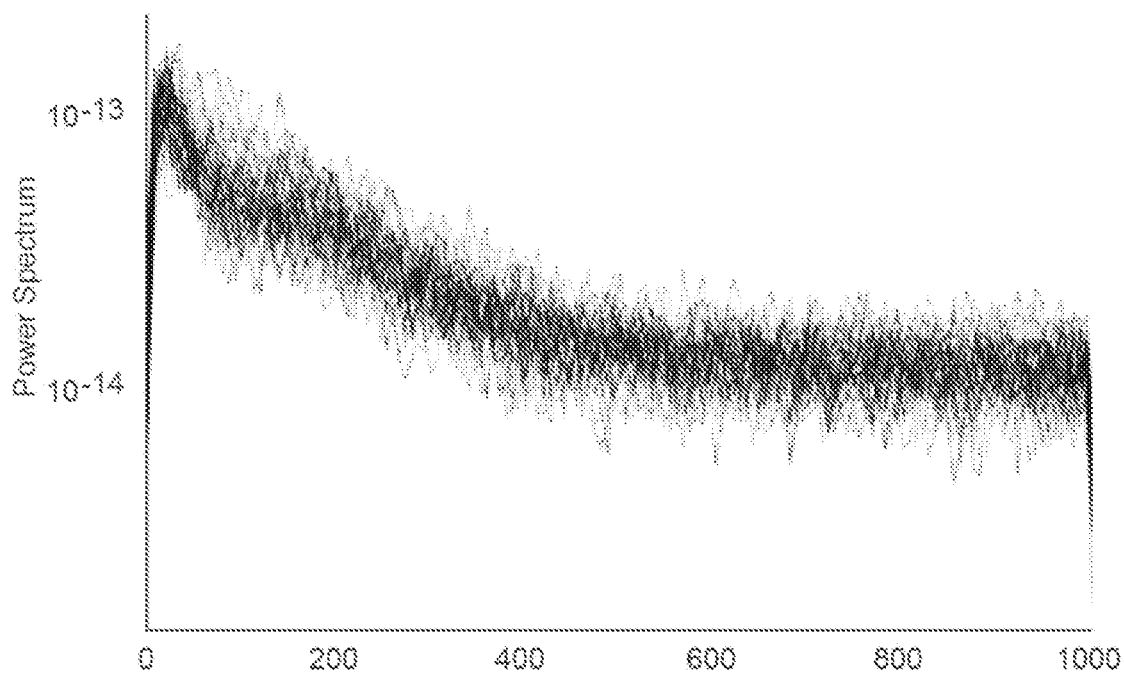
FIGS. 8C and 8D illustrate results of an experiment in which an additional anti-aliasing filter was used, thereby creating a two-stage filter, where
Figure 8D:
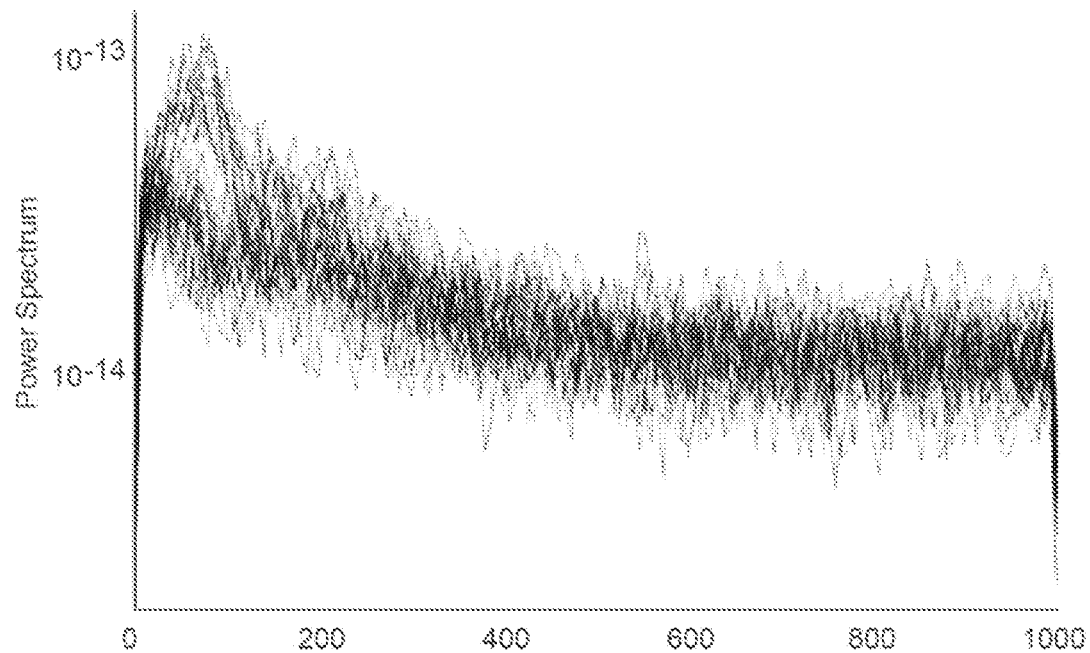

FIGS. 8A-D illustrate results from an experiment in which the effect of implementing a higher-order anti-aliasing filter was observed. FIGS. 8A and 8B illustrate two channels of a 16-channel EMG control interface, where a single anti-aliasing filter was arranged 1.5 cm from the ADC of the EMG control interface. A first noise peak 810 at approximately 250 Hz is observed in the channel shown in FIG. 8B and a second noise peak 812 at approximately 500 Hz is observed in both channels shown in FIGS. 8A and 8B. FIGS. 8C and 8D illustrate the same two channels of the 16-channel EMG control interface, where a second anti-aliasing filter is added close to the amplifier output such that the analog signal chain may include two filters (or alternatively, a two-stage filter). As observed in FIGS. 8C and 8D, the previously observed noise peaks at 250 and 500 Hz are no longer observed, providing evidence that a higher-order filter attenuated the noise induced in the analog signal chain. For these plots, the x-axis unit is frequency in Hz.

In some embodiments, electromagnetic noise may be reduced by changing a characteristic of the ADC circuit. Conventional ADC circuit is often susceptible to the aliasing effect, as discussed above. In some embodiments, a continuous-time ADC is used in the analog signal chain of the EMG control interface, which does not have the same aliasing properties. Although continuous-time ADCs may be more expensive and consume more power than a conventional ADC circuit, the tradeoff of improved electromagnetic interference reduction may be suitable for some applications.

Figure 9:
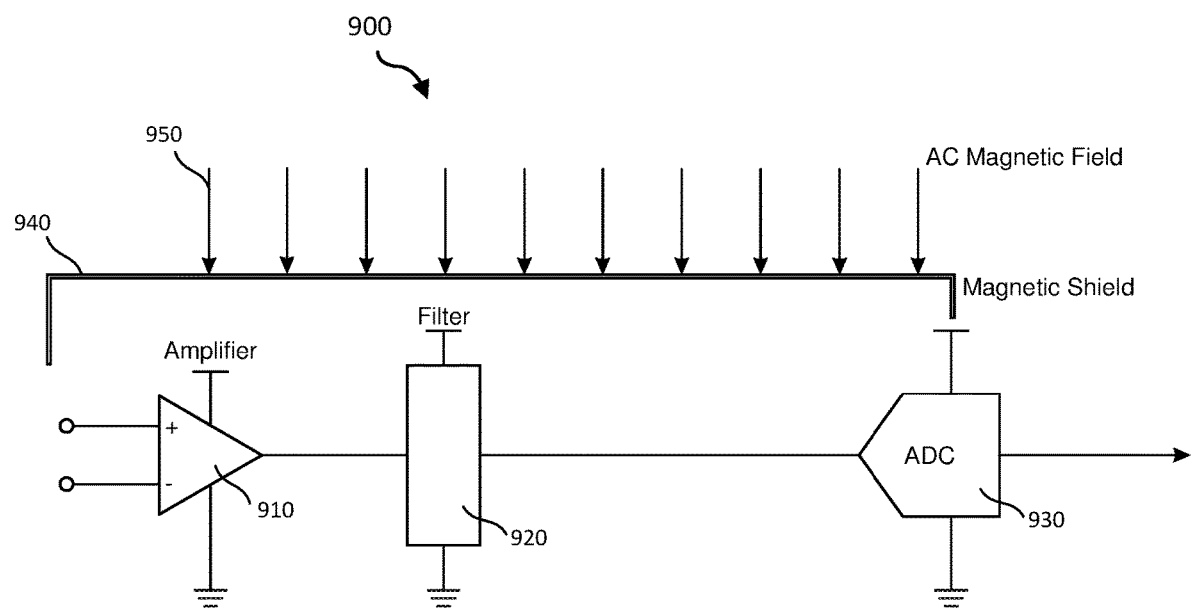
FIG. 9 illustrates a technique for reducing electromagnetic noise using a shielding material, in accordance with some embodiments.

FIG. 9 illustrates example approaches for reducing electromagnetic interference, in accordance with some embodiments. The figure shows an analog circuit portion of a device 900, (e.g., including an EMG control interface), that may include an amplifier 910, an anti-aliasing filter 920, and ADC 930. The device also includes a shielding material 940, that may be configured to shield the analog circuit from an electromagnetic field schematically represented by arrows 950. In some embodiments, the shielding material 940 includes a magnetic shielding material, such as a composition including a ferrite material, and may be configured such that the magnetic shielding material redirects the AC magnetic field around the analog circuit.

In some examples, the shielding material may include an electrically conductive material. A shielding material may include a metal layer, such as an aluminum layer, having a metal layer thickness of 2 mm or less, for example, a thickness of 1 mm or less. In some embodiments, multiple layers of shielding material may be used, for example, if one layer of magnetic shielding does not offer the desired attenuation of noise signals. The shielding material as disclosed herein can be formed from or include any suitable material (including flexible and lightweight materials) provided it achieves the functionality described herein. In addition to the those mentioned above, such materials include but are not limited to: one or more metals and/or alloys or compounds (e.g., those comprising aluminum, bronze, tin, copper, and/or mu-metals), carbon-filled nylon, conductive paint (e.g., silver and/or carbon-based paint), conductive fabric (e.g., silver nanowire), conductive polymers (e.g., carbon or graphene filled polylactic acid (PLA)), conductive plastics, conductive rubbers, conductive silicones, or combinations thereof. The shielding material may also include one or more non-conductive components that may be combined with any one or more conductive components, such as the aforementioned examples.

Figure 10:
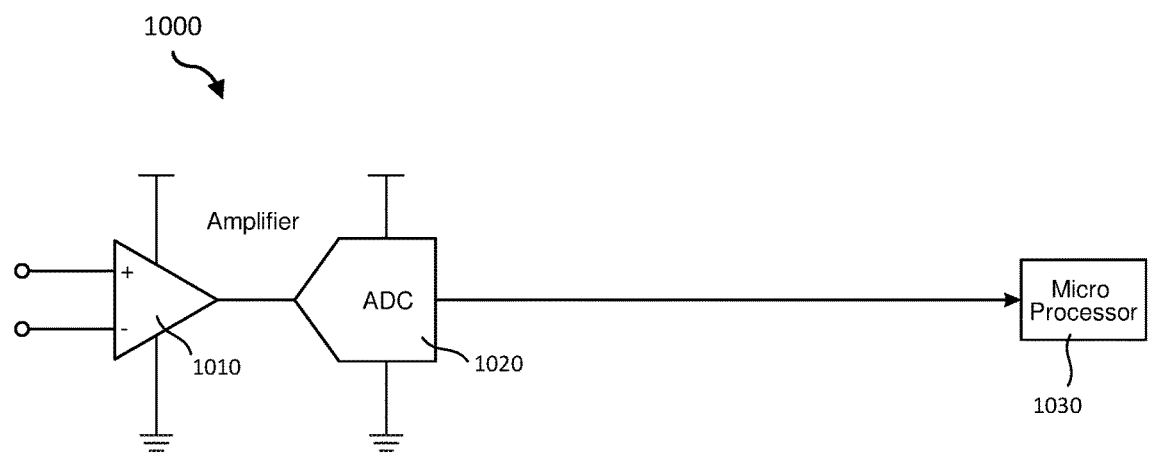
FIG. 10 illustrates a technique for reducing electromagnetic noise by employing an ADC for each channel of a multi-channel control interface, in accordance with some embodiments.

FIG. 10 illustrates an example technique for reducing electromagnetic interference in accordance with some embodiments. FIG. 10 shows a portion of a device 1000 including an analog circuit including an ADC 1030 located within each analog channel. The ADC may be located as close to the output of amplifier 1020 as possible. By locating an ADC close to each amplifier output for the analog channels, the analog signal may be converted into a corresponding digital signal as it is outputted by the amplifier 610, using a trace that may be around a few mm in length. In some embodiments, the trace length may not exceed 20 mm to avoid noise signal generation through an AC magnetic field. The digital signal may then be provided to microprocessor 1010. Noise generation may not be a problem for the digital signals in this example.

In some examples, a method of reducing electromagnetic interference in an analog circuit of a control device for an extended reality (XR) system may include: providing an analog signal chain circuit that includes at least one amplifier and an analog-to-digital converter coupled to an amplifier by one or more electrical conductors; and reducing electromagnetic interference induced on the one or more electrical conductors by an external AC magnetic field by configuring at least one component of the control device to reduce the electromagnetic interference. The step of reducing the electromagnetic interference may include providing, in the analog signal chain circuit, at least one fully differential amplifier configured to subtract electromagnetic noise present on the one or more electrical conductors, that may include providing at least two fully differential amplifiers in the analog signal chain circuit. Reducing the electromagnetic interference may also include providing, in the analog signal chain circuit, at least one anti-aliasing filter arranged between an amplifier and the analog-to-digital converter, and/or arranging an anti-aliasing filter to be closer to the analog-to-digital converter than an amplifier. An anti-aliasing filter may include an anti-aliasing filter having at least two stages. In addition, reducing the electromagnetic interference may include forming a shielding material around at least a portion of the analog signal chain circuit. In one example, the method may also include providing, in the analog signal chain circuit, a plurality of analog-to-digital converters, each of which is configured to process the output of a single signal channel of a plurality of signal channels. In another example, the method may also include reducing the electromagnetic interference by integrating a magnetic tracker receiver within the control device and configuring a distance between the magnetic tracker receiver and a magnetic tracker transmitter of the XR system to reduce the electromagnetic interference.

Figure 11:
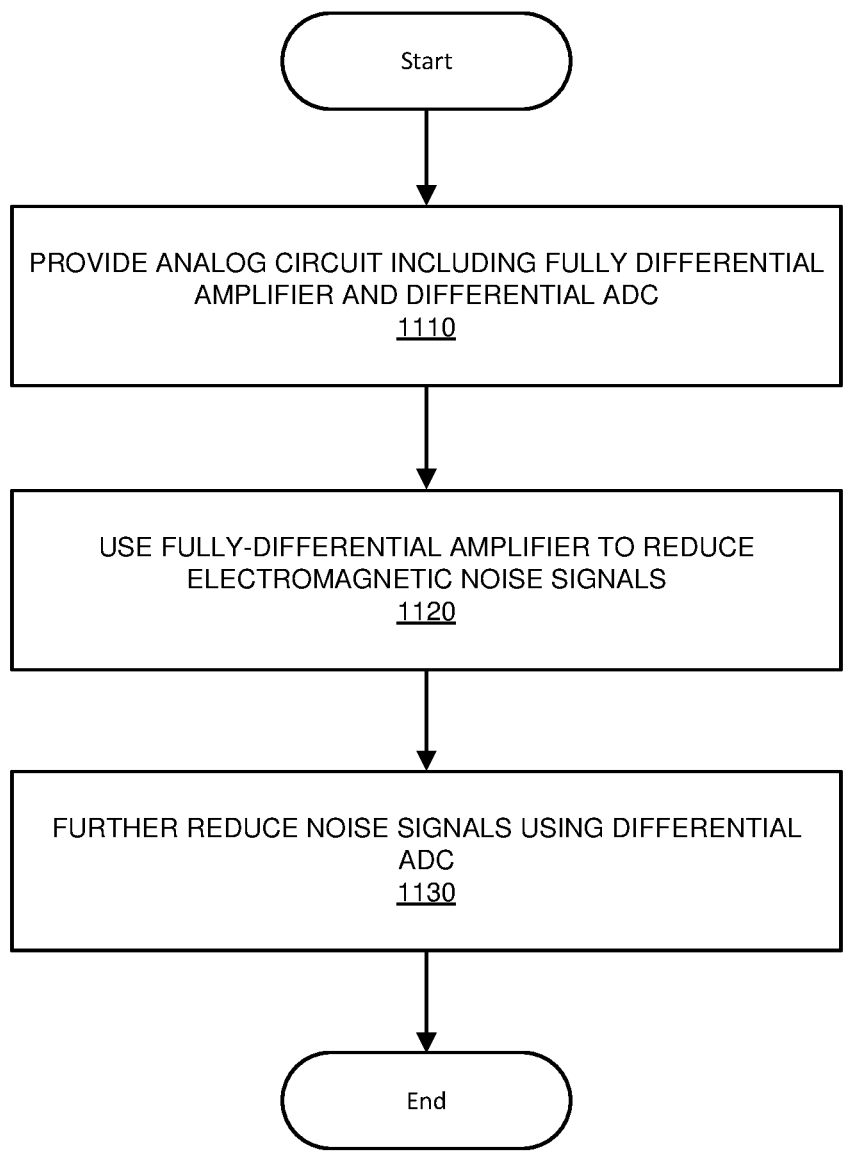
FIGS. 11-12 show example methods, in accordance with some embodiments.

FIG. 11 illustrates an example method 1100 for reducing electromagnetic noise in an analog circuit of a device, such as a control device for an extended reality (XR) system. In this example, the method may include: providing an analog circuit including a differential amplifier (such as a fully differential amplifier) and an analog-to-digital converter (ADC, such as a differential ADC) (1110), where the ADC is coupled to the amplifier by one or more electrical conductors; reducing the electromagnetic noise induced in the analog circuit by using the differential amplifier to cancel common mode noise signals (1120); and further reducing the noise signal using the differential ADC (1130). In this example, a differential ADC may output a digital signal based on the difference between two analog input voltages. If there is similar noise signal in both analog input voltages, the difference between the input voltages, and hence the digital signal, may be generally independent of the electromagnetic noise.

Figure 12:
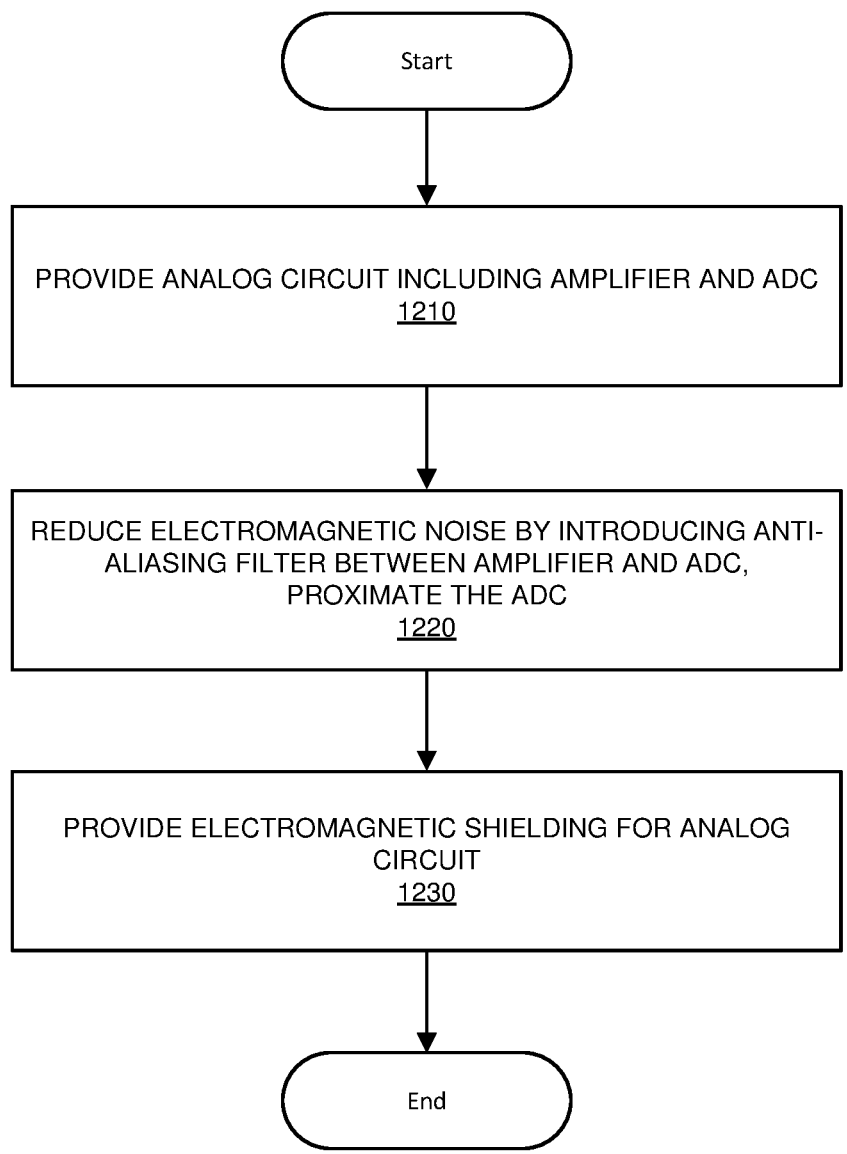

FIG. 12 illustrates another example method 1200 of reducing electromagnetic noise in the analog circuit of a device, such as a control device for an extended reality (XR) system, such as an augmented reality or virtual reality system. In this example, the method may include: providing an analog circuit including a differential amplifier and an analog-to-digital converter (ADC) (1210), where the ADC is coupled to the amplifier by one or more electrical conductors; reducing the electromagnetic noise induced in the analog circuit by providing at least one anti-aliasing filter located between the amplifier and the analog-to-digital converter (ADC), proximate the ADC (1220); and (optionally) providing shielding, at least for the analog circuit portion of the device, from electromagnetic radiation (1230). The analog circuit may be configured to receive sensor signals, such as EMG signals. The electrical connection between the anti-aliasing filter and the ADC may have a length of less than or approximately 15 mm, such as less than or approximately 5 mm, and in some examples less than or approximately 3 mm. In some examples, the anti-aliasing filter and ADC may be combined into a single package, or combined within a single shielded component, or combination of components having at least a partially shielded enclosure.

In some examples, electromagnetic noise reduction may include the use of hardware, software, or a combination thereof. When implemented in software, the software code may be executed on any suitable processor or collection of processors, whether provided in a single computer or distributed among multiple computers. Any component or collection of components that perform the functions described above may be generically considered as one or more controllers that control the above-discussed functions. The one or more controllers may be implemented in numerous ways, such as with dedicated hardware or with one or more processors programmed using microcode or software to perform the functions recited above.

In some examples, a device may include at least one non-transitory computer readable storage medium (e.g., a computer memory, a portable memory, a compact disk, etc.) encoded with a computer program (i.e., a plurality of instructions), which, when executed on a processor, performs the above-discussed functions of the described examples. The computer-readable storage medium may be transportable such that the program stored thereon may be loaded onto any computer resource to implement any suitable aspects of the described examples. In addition, the reference to a computer program which, when executed, performs the above-discussed functions, is not limited to an application program running on a host computer. Rather, the term computer program may be used herein to reference any type of computer code (e.g., software or microcode) that may be employed to program a processor to implement the one or more aspects of the described example In some examples, a device (such as a control device for an extended reality (XR) system) includes an analog signal chain circuit including at least one amplifier configured to amplify analog electrical signals recorded from a body of a user on which the device is worn, and an analog-to-digital converter configured to convert the amplified analog electrical signals to digital signals. In these examples, at least one component of the device is configured to reduce electromagnetic interference induced on one or more conductors within the analog signal chain circuit by an external AC magnetic field.

In some examples, the amplifier may include at least one fully differential amplifier configured to reduce the electromagnetic interference. In some examples, the amplifier may include at least two fully differential amplifiers. In some examples, the analog signal chain circuit may further include an anti-aliasing filter arranged between an amplifier and a respective analog-to-digital converter, where the anti-aliasing filter is configured to reduce electromagnetic interference. In some examples, the anti-aliasing filter may include an anti-aliasing filter arranged closer to the analog-to-digital converter than the amplifier. In some examples, the distance between the anti-aliasing filter and the analog-to-digital converter is less than 2 cm. The anti-aliasing filter may have one or more stages, such as at least two stages. An example device may further include a shielding material formed around at least a portion of the analog signal chain circuit, where the shielding material is configured to reduce the electromagnetic interference.

In some examples, a device includes a plurality of signal channels, where each signal channel is configured to record an analog electrical signal from the body of the user. The analog signal chain circuit may further include a plurality of analog-to-digital converters, each of which is configured to process the analog electrical signal from one of the plurality of signal channels. In some examples, the control device may include a magnetic tracker receiver. The distance between the magnetic tracking receiver and the magnetic tracking system transmitter of the XR system may be configured to reduce the electromagnetic interference. An example device, such as a control device, may include a plurality of EMG sensors configured to record a plurality of EMG signals from the body of the user, with an amplifier coupled to one or more of the plurality of EMG sensors. The analog-to-digital converter may include a continuous-time analog-to-digital converter configured to reduce the electromagnetic interference.

In some examples, a method of reducing electromagnetic interference in an analog circuit of a control device for an extended reality (XR) system includes: providing an analog signal chain circuit including at least one amplifier and an analog-to-digital converter coupled to an amplifier by one or more electrical conductors; and reducing electromagnetic interference induced on the one or more electrical conductors by an external AC magnetic field by configuring at least one component of the control device to reduce the electromagnetic interference. The step of reducing the electromagnetic interference may include providing, in the analog signal chain circuit, at least one fully differential amplifier configured to subtract electromagnetic noise present on the one or more electrical conductors, that may include providing at least two fully differential amplifiers in the analog signal chain circuit. Reducing the electromagnetic interference may also include providing, in the analog signal chain circuit, at least one anti-aliasing filter arranged between an amplifier and the analog-to-digital converter, and/or arranging an anti-aliasing filter to be closer to the analog-to-digital converter than an amplifier. An anti-aliasing filter may include an anti-aliasing filter having at least two stages. Reducing the electromagnetic interference may include forming a shielding material around at least a portion of the analog signal chain circuit. An example method may further include providing, in the analog signal chain circuit, a plurality of analog-to-digital converters, each of which is configured to process output of a single signal channel of a plurality of signal channels. An example method may further include reducing the electromagnetic interference by integrating a magnetic tracker receiver within the control device such that a distance between the magnetic tracker receiver and a magnetic tracker transmitter of the XR system is configured to reduce the electromagnetic interference. In some examples, the magnetic tracker transmitter may be located within or supported by a head-mounted device or positioned in another location away from the sensors within the control device. The control device may include one or more magnetic tracker receiver coils, and/or receive signals from one or more magnetic tracker receiver coils. Receiver coils may be located on, for example, the hand, wrist, limb segments, joints, head, or other locations on the user's body.

In some examples, an extended reality (XR) system may include a head-mounted device, such as a headset configured to be worn on a user's head, and a control device configured to be worn on the user's arm or wrist. In these examples, the control device includes an analog signal chain circuit including at least one amplifier configured to amplify analog electrical signals recorded from a body of the user and an analog-to-digital converter configured to convert the amplified analog electrical signals to digital signals. In addition, at least one component of the XR system may be configured to reduce electromagnetic interference induced on one or more conductors within the analog signal chain circuit by an external AC magnetic field.

As detailed above, an electromagnetic field, such as a transmitter signal, may induce noise signals within the receiver of an apparatus. This transmitter signal may be generated by passing an alternating current from an alternating voltage source through a coil. The transmitter signal may generate a noise signal within a closed-loop or open-loop conductor within the receiver due, for example, to an interaction with the transmitter signal. A closed-loop or open-loop conductor may be formed, at least in part, by conducting tracks within the receiver circuit.

An example control device may include EMG sensors arranged circumferentially around a band, such as an elastic band configured to be worn around a body part of a user, such as the lower arm, wrist, one or more fingers, ankle, foot, head, or chest. Any suitable number of neuromuscular sensors may be used. The number and arrangement of neuromuscular sensors within a device may depend on the particular application for which the control device is used. In some examples, the sensors of an apparatus may be coupled together, for example, using flexible electronics incorporated into a control device, for example, within a flexible band.

In some examples, an apparatus, such as a control device (e.g., including an armband, wristband, and/or a head-mounted device) may be configured to generate a control signal for controlling an external device. The external device that may be controlled by the apparatus may include one or more of the following: an augmented reality system, a robot, an appliance (such as a television, radio, or other audiovisual device), an in-house system (such as heating or air conditioning), a vehicle, or other electronic device including a screen (e.g., to scroll through text, interact with a user interface, or control the operation of software). In some examples, an apparatus may be configured to control a virtual avatar within an augmented reality or virtual reality environment, or to perform any other suitable control task.

In some embodiments, the output of one or more of the sensors may be optionally processed using hardware signal processing circuit (e.g., to perform amplification, filtering, and/or rectification). In some embodiments, at least some signal processing of the output of the sensors may be performed in software. Thus, signal processing of signals sampled by the sensors may be performed in hardware, software, or by any suitable combination of hardware and software, as aspects of the technology described herein are not limited in this respect.

An example device may include a control device and one or more dongle portions in communication with the control device (e.g., via BLUETOOTH or another suitable short-range wireless communication technology). The control device may include one or more sensors, that may include electrical sensors including one or more electrodes. The electrical outputs from the electrodes, that may be referred to as sensor signals, may be provided to an analog circuit configured to perform analog processing (e.g., filtering, etc.) of the sensor signals. The processed sensor signals may then be provided to an analog-to-digital converter (ADC), that may be configured to convert analog signals to digital signals that may be processed by one or more computer processors. Example computer processors may include one or more microcontrollers (MCU), such as the nRF52840 (manufactured by NORDIC SEMICONDUCTOR). The MCU may also receive inputs from one or more other sensors. The device may include one or more other sensors, such as an orientation sensor, that may be an absolute orientation sensor and may include an inertial measurement unit. An example orientation sensor may include a BNO055 inertial measurement unit (manufactured by BOSCH SENSORTEC). The device may also include a dedicated power supply, such as a power and battery module. The output of the processing performed by MCU may be provided to an antenna for transmission to the dongle portion or another device. Other sensors may include mechanomyography (MMG) sensors, sonomyography (SMG) sensors, electrical impedance tomography (EIT) sensors, and other suitable type of sensors.

A dongle portion may include one or more antennas configured to communicate with the control device and/or other devices. Communication between device components may use any suitable wireless protocol, such as radio-frequency signaling and BLUETOOTH. Signals received by the antenna of dongle portion may be provided to a computer through an output, such as a USB output, for further processing, display, and/or for effecting control of a particular physical or virtual object or objects.

In some examples, a magnetic tracker transmitter may be provided by a separate device, such a separate computer device that may not be supported by a user. For example, a magnetic tracker transmitter may be located at a fixed location relative to the environment (e.g., a room) in which the user is located.

In some examples, a device according to the principles disclosed herein may include a higher-order anti-aliasing filter to attenuate the noise signals. This filter, plus the amplifier block, may offer a transfer function such that the amplified in-band signals are at least 90 dB higher than the attenuated noise signals. Such a configuration may use traces between ADC inputs and anti-aliasing filters outputs that are as short as practically possible. The noise signal coupled into unprotected traces may be negligible if such traces are kept short (e.g., approximately 3 mm in length, or less.)

In some examples, an ADC may be located within each analog channel, and may be located as close to the amplifier output as possible. For example, the analog signal may be converted into a corresponding digital form soon after it is outputted by the amplifier, for example, using a trace (e.g., a PCB track or other electrical conductor) having a length of approximately 3 mm or less. In some examples, the trace length may be approximately equal to or less than 2 mm to substantially avoid noise generation through the alternating electromagnetic field.

Examples include various methods and apparatuses for reducing electromagnetic interference in sensors used in extended reality (XR) environments, such as augmented reality (AR) or virtual reality (VR) environments. As is explained in greater detail below, positional tracking may be used in XR environments (such as AR or VR environments) to track movements, for example, with six degrees of freedom. A corresponding computing device may be configured to estimate a position of an object relative to the environment using one or more positional tracking approaches. Positional tracking may include magnetic tracking, in which the magnitude of a magnetic field may be measured in different directions.

An example apparatus may include a control device, that may be configured to be worn on the wrist of a user, and a head-mounted device. The control device, such as a wearable control device, may be configured to be supported on the wrist or lower arm of a user, and may include one or more sensors. The head-mounted device may include a headset, augmented reality spectacles, or other device configured to be supported by the head of a user, for example, by one or more frame elements, straps, and/or other support elements. The headset may take the form of a visor or helmet, or may be supported by a frame similar to those of spectacles. The head-mounted device may be configured to provide an extended reality environment to a user, such as a virtual reality or augmented reality environment. The control device and the head-mounted device may be in communication with one another, such as via wireless or wired communication components. The control device may detect gestures or other movements of the hands of the user, and provide control signals to the head-mounted device. The control signals may be used to modify augmented or virtual reality image elements displayed to a user. In some examples, control signals may be used to control real (physical) devices, that may be viewed by the user as part of an extended reality experience. In some examples, the apparatus may include a control element used to send control signals to a computer device.

An example magnetic tracker (that may also be referred to as a magnetic tracking system or magnetic tracker) may determine the intensity of a magnetic field using one or more electromagnetic sensors, such as magnetic sensors. The magnetic tracker may include a base station having a transmitter configured to generate an alternating or static electromagnetic field, and one or more sensors that may be configured to send sensor data to a computing device. The sensor data may be related to a position and/or orientation of the sensor with respect to the transmitter. The magnetic tracker may also be configured to enable the determination of object orientation. For example, if a tracked object is rotated, the distribution of the magnetic field along various axes (e.g., orthogonal axes in relation to the sensor) may change. The resulting change in the sensor signal may be used to determine the orientation of the sensor, and, optionally, the orientation of an object on which the sensor is located.

In one embodiment, an example apparatus may include an improved human-machine interface for XR devices, such as AR or VR devices, and an apparatus configured to control computing devices or other electronic devices. This example apparatus may also include a control device configured to receive and process electrical signals derived from the body of a user to provide a control signal. The control signal may be used for object manipulation within an XR environment, control of a computing device, or control of any other suitable electronic device. The control device may include one or more sensors, that may include one or more of an electromyography (EMG) sensor, mechanomyography (MMG) sensor, sonomyography (SMG) sensor, electrical impedance tomography (EIT) sensor, and/or any other suitable sensor.

In some examples, an apparatus, such as a control device, may include one or more printed circuit boards (PCBs), that may be electrically interconnected. In some examples, a PCB may include a plurality of electrically conducting traces, which in some examples may be configured to sense signals, such as signals from the body of a user. The apparatus may be configured to include one or more electronic circuits configured to provide signal amplification, data acquisition, wireless transmission, or other suitable signal acquisition and processing operations.

An apparatus including a magnetic tracker may allow, for example, manipulation of objects in XE environments. An alternating or static magnetic field produced by a transmitter of a magnetic tracker may induce voltage and/or current within an apparatus. For example, electromagnetic fields generated by the transmitter may induce electrical signals within the apparatus, for example, due to electromagnetic coupling to electrical conductors within the apparatus, such as copper tracks within a PCB. In some examples, copper tracks may help form electrically conducting loops, and stray signals may be induced within such loops. The stray signals may induce noise signals within the device, and the noise signals may have the same frequency as the transmitter. The transmitter frequency may be, for example, in the range of approximately 10 kHz to approximately 50 kHz. The transmitter frequency may be higher than the frequency of signals obtained from the body of the user, for instance higher than electromyography signals, which normally are in the frequency range of between approximately 20 Hz to approximately 3 kHz. A sampling frequency, that may be twice the frequency of the biometric signals (e.g., approximately 6 kHz), may be used to convert the analog signals into digital. Even though the induced noise frequency may be much higher than the biometric signals from human bodies, after the analog-digital conversion stage, the noise may be under-sampled, and alias signals originating from the under-sampling of the noise signal may be introduced into the frequency band of the biometric signals. Effectively, high-frequency noise signals may be "down-converted" in the frequency band and be combined with the biometric signals of interest. The noise signal may become stronger as the transmitter is moved closer to the apparatus.

Positional tracking may be used in XR environments to track movements with up to and including six degrees of freedom. Computer devices may be configured, with hardware and/or software, to estimate the positions of objects relative to the environment using positional tracking technologies. Magnetic tracking is a technique in which the magnitude of a magnetic field may be measured in different directions to track positions of one or more objects in an environment.

A magnetic tracking system (or magnetic tracker) may be configured to measure the intensity of an inhomogeneous magnetic field using one or more electromagnetic sensors. An example magnetic tracker may include a transmitter configured to generate an alternating or static electromagnetic field, and one or more electromagnetic sensors configured to provide a respective sensor position (e.g., with respect to the transmitter) to a computer device. The orientation of an object may also be determined using a magnetic tracker. For instance, if a tracked object is rotated, the distribution of the magnetic field along the various axes may change, and these changes may be used to determine the object's orientation.

An example apparatus may include control devices configured as human-machine interfaces, and may be used for immersive XR applications (such as virtual reality applications), and more generally to control computer devices. An example interface device may be configured to process electrical signals derived from the body of a user, and may be used to achieve realistic object manipulation in an XR environment. Example devices may include one or more sensors, including one or more electromyography (EMG) sensors, mechanomyography (MMG) sensors, sonomyography (SMG) sensors, electrical impedance tomography (EIT) sensors, and/or other suitable sensors. Example devices may include one or more printed circuit boards (PCBs), that may include boards connected together, that may include many (e.g., thousands) of electrically conductive traces routed together to achieve certain functionalities such as sensing signals from a user body, signal amplification, data acquisition, wireless transmission, and/or other suitable signal acquisition and processing operations.

Example devices including a magnetic tracker may enable, for example, manipulation of objects in XR environments. However, an alternating or static magnetic field produced by the transmitter of a magnetic tracker may induce a voltage or current within open or closed electrically conductive loops within the device. An electrically conductive loop may include device components (e.g., copper traces on a PCB, electronic components, wires, and the like), resulting in noise being introduced into the device. The introduced noise may fluctuate at the same frequency used by the magnetic tracker, that may operate, for example, at a frequency within a range of 10 kHz to 50 kHz. In some examples, a magnetic tracker transmitter and/or a corresponding magnetic tracker receiver may include at least one coil, such as a 3-axis coil arrangement. Signal processing may be used to establish the three-dimensional relationship between transmitter and receiver coil arrangements.

Magnetic tracker frequencies may be higher than frequencies associated with signals recorded and/or derived from the user's body. For instance, frequencies associated with EMG signals typically range between ~20 Hz to ~3 KHz. In some examples, a device may use a signal sampling frequency twice as large as the highest frequency of the signal of interest (e.g., around ~6 kHz) to convert the analog signals into digital signals (e.g., using analog to digital conversion (ADC) circuit). Despite the induced noise frequency being substantially higher than the frequency of the recorded biometric signals, when the high frequency noise is provided as input to the ADC circuit, it may be undersampled and an aliased image of the noise may interfere with the frequency band of interest associated with the biometric signals. The high frequency noise signal may be "down-converted" into the frequency band of interest by the ADC circuit. In some examples, a device is configured to reduce electromagnetic interference in a control device, such as a wearable control device.

In some examples, an apparatus may include a control device for an extended reality system. The control device may include analog signal chain circuit including at least one amplifier configured to amplify analog electrical signals recorded from a body of a user on which the control device is worn, and an analog-to-digital converter configured to convert the amplified analog electrical signals to digital signals, where at least one component of the control device is configured to reduce electromagnetic interference induced on one or more conductors within the analog signal chain circuit by an external AC magnetic field. In some examples, an amplifier may include at least one fully differential amplifier configured to reduce the electromagnetic interference. In some examples, an amplifier includes at least two fully differential amplifiers. In some examples, the analog signal chain circuit may further include at least one anti-aliasing filter arranged between an amplifier and the analog-to-digital converter, where an anti-aliasing filter may be configured to reduce the electromagnetic noise within the analog circuit. In some examples, an anti-aliasing filter may be located closer to the analog-to-digital converter than the associated amplifier. In some examples, a distance between the anti-aliasing filter and the analog-to-digital converter may be less than 20 mm, and in some examples may be less than 5 mm, such as less than 2 mm. In some examples, an anti-aliasing filter may have at least two stages. In some examples, the control device may further include a shielding material formed around at least a portion of analog circuit.

In some examples, a device, such as a control device, may further include a plurality of signal channels, where each signal channel is configured to record an analog electrical signal from the body of the user, and where the analog circuit further includes a plurality of analog-to-digital converters, each of which is configured to process the analog electrical signal within one of the plurality of signal channels. The analog circuit may include a plurality of signal channels, and each signal channel may include an analog-to-digital converter.

In some examples, a device, such as a control device, may further include a magnetic tracking system receiver (also referred to as a magnetic tracker receiver), where, in some examples, a distance between the magnetic tracker receiver and the magnetic tracker transmitter of the XR system may be configured to reduce the electromagnetic noise in the analog circuit. For example, the magnetic tracker receiver may be located adjacent or otherwise proximate the head of the user. In some examples, the control device may further include a plurality of EMG sensors configured to record a plurality of EMG signals from the body of the user, where an amplifier coupled to one or more of the plurality of EMG sensors. In some examples, the analog-to-digital converter may include a continuous-time analog-to-digital converter configured to reduce the electromagnetic interference. In some examples, the magnetic tracker system may be trained, for example, by comparison of receiver signals with analysis of images determined using an optical imaging system, or using a training process where a user places body parts, such as hands, into predetermined configurations. Magnetic tracker receivers may be distributed over the body of a user, for example, distributed over the torso, limb segments, and joints of a user. The magnetic tracking data may also be used in conjunction with a musculo-skeletal model of the user.

Some embodiments are directed to methods of reducing electromagnetic interference in analog circuit of a control device for an extended reality system. An example method may include providing an analog circuit including at least one amplifier and an analog-to-digital converter coupled to an amplifier by one or more electrical conductors, and reducing electromagnetic interference induced on the one or more electrical conductors by an external AC magnetic field by configuring at least one component of the control device to reduce the electromagnetic interference.

In some examples, a method reducing the electromagnetic interference includes providing in the analog signal chain circuit at least one fully differential amplifier configured to subtract electromagnetic noise present on the one or more electrical conductors. In some examples, the analog circuit may include at least one fully differential amplifier, such as at least two fully differential amplifiers. In some examples, reducing the electromagnetic interference includes providing in the analog circuit at least one anti-aliasing filter arranged between an amplifier and the analog-to-digital converter. In some examples, reducing the electromagnetic interference further includes arranging an anti-aliasing filter closer to the analog-to-digital converter than to an amplifier. In some examples, an anti-aliasing filter may include an anti-aliasing filter having at least two stages. In some examples, reducing the electromagnetic interference may include forming a shielding material around at least a portion of the analog signal chain circuit.

In some examples, a method includes reducing electromagnetic noise induced in an analog circuit by using the fully differential amplifier to reduce the effect of electromagnetic noise signals (e.g., present in both inputs of the fully differential amplifier) on the outputs of the fully differential amplifier, and further reducing the noise signal using the differential analog-to-digital converter configured to receive the outputs of the fully differential amplifier. The electromagnetic noise may be generated by a transmitter of a magnetic tracker system. The analog circuit may be configured to receive and process sensor signals from a plurality of electromyography sensors. In some examples, a method may further include using an anti-aliasing filter to further reduce the electromagnetic noise.

In some examples, the method may further include providing in the analog signal chain circuit a plurality of analog-to-digital converters, each of which is configured to process output of a single signal channel of a plurality of signal channels. In some examples, reducing the electromagnetic interference may include integrating a magnetic tracking system receiver with the control device such that a distance between the magnetic tracking system receiver and a magnetic tracking system transmitter of the XR system is configured to reduce the electromagnetic interference.

Some embodiments are directed to an XR system. The XR system may include a headset configured to be worn on a user's head, and a control device configured to be worn on the user's arm or wrist. The control device may include analog signal chain circuit including at least one amplifier configured to amplify analog electrical signals recorded from a body of the user, and an analog-to-digital converter configured to convert the amplified analog electrical signals to digital signals, where at least one component of the XR system is configured to reduce electromagnetic interference induced on one or more conductors within the analog signal chain circuit by an external AC magnetic field. All combinations of the concepts discussed herein are contemplated as being part of the disclosed subject matter (provided such concepts are not mutually inconsistent).

In some examples, an apparatus may include at least one physical processor, and physical memory including computer-executable instructions that, when executed by the physical processor, cause the physical processor to provide control signals to an extended reality headset (or other head-mounted device) based on detected EMG signals and/or to perform any of the other methods described herein.

In some examples, a non-transitory computer-readable medium may include one or more computer-executable instructions that, when executed by at least one processor of a computing device, cause the computing device to provide control signals to an extended reality headset (or other head-mounted device) based on detected EMG signals and/or to perform any of the other methods described herein.

Example Embodiments

Example 1. An example apparatus includes a head-mounted device that, when worn by a user, is configured to present an extended reality view to the user; and a control device including one or more electrodes that, when worn on a wrist of the user, contact the skin of the user, the control device including: an analog circuit including an amplifier configured to receive sensor signals from the one or more electrodes; an analog-to-digital converter (ADC) configured to receive analog sensor signals from the analog circuit and provide digital sensor signals; a processor configured to receive the digital sensor signals and provide control signals based on the digital sensor signals; and a control device antenna configured to transmit the control signals to the head-mounted device, wherein the head-mounted device is configured to modify the extended reality view in response to the control signals.

Example 2. The apparatus of example 1, wherein the amplifier includes a differential amplifier configured to remove electromagnetic noise generated within the analog circuit.

Example 3. The apparatus of any of examples 1-2, wherein the differential amplifier includes a fully differential amplifier.

Example 4. The apparatus of any of examples 1-3, wherein the ADC includes a differential ADC configured to remove electromagnetic noise generated within the analog circuit.

Example 5. The apparatus of any of examples 1-4, wherein the analog circuit includes a plurality of analog channels, and each analog channel has an associated one of a plurality of ADCs, wherein the plurality of ADCs includes the ADC.

Example 6. The apparatus of any of examples 1-5, wherein the analog circuit includes an anti-aliasing filter.

Example 7. The apparatus of any of examples 1-6, wherein the anti-aliasing filter is located proximate the ADC such that an electrical connection between the anti-aliasing filter and the ADC is shorter than approximately 1.5 cm.

Example 8. The apparatus of any of examples 1-7, wherein the amplifier is located proximate the ADC such that an electrical connection between an output of the amplifier and an input of the ADC is less than approximately 3 mm.

Example 9. The apparatus of any of examples 1-8, further including a magnetic tracker including a transmitter and a plurality of receivers.

Example 10. The apparatus of any of example 9, wherein the transmitter of the magnetic tracker is supported by the head-mounted device.

Example 11. The apparatus of any of examples 9-10, wherein at least one of the plurality of receivers of the magnetic tracker is configured to determine an orientation of a finger of the user.

Example 12. The apparatus of any of examples 9-11, wherein the plurality of receivers of the magnetic tracker are located within a control glove configured to be worn on a hand of the user, and the control glove is in communication with the control device.

Example 13. The apparatus of any of examples 1-12, wherein the control device includes a shielding layer configured to shield the analog circuit from electromagnetic radiation.

Example 14. The apparatus of example 13, wherein the shielding layer includes a ferrite material.

Example 15. The apparatus of any of examples 13-14, wherein the shielding layer includes at least one of the following: a metal layer, alloy layer, conductive polymer, carbon-filled nylon, conductive paint, conductive fabric, conductive plastic, conductive rubber, and/or conductive silicone.

Example 16. The apparatus of any of examples 1-15, wherein the head-mounted device includes at least one of a virtual-reality headset or augmented reality spectacles.

Example 17. The apparatus of any of examples 1-16, wherein the control device includes one or more electromyography sensors, wherein: the one or more electromyography sensors include the one or more electrodes, and the one or more sensors provides the sensor signals received by the analog circuit.

Example 18. The apparatus of any of examples 1-17, wherein the processor further receives inertial sensor signals from an inertial sensor, and the control signals are based on the digital sensor signals and the inertial sensor signals.

Example 19. An example method includes reducing electromagnetic noise in an analog circuit by: applying a fully differential amplifier to at least one output of the analog circuit; and further reducing the electromagnetic noise in the analog circuit by applying a differential analog-to-digital converter to at least one output of the fully differential amplifier, wherein the analog circuit is configured to receive and process sensor signals from one or more neuromuscular sensors.

Example 20. The method of example 19, further including applying an anti-aliasing filter to at least one output of the analog circuit to further reduce the electromagnetic noise.

Example 21. The method of any of examples 19-20, wherein the one or more neuromuscular sensors include sensors for detecting EMG signals.

Example 22. An example apparatus includes: a head-mounted device that includes a magnetic tracking system transmitter, and when worn by a user, is configured to present an extended reality view to the user; a control device including one or more electromyography electrodes that contact the skin of the user when worn by the user, the control device including: an analog circuit including an anti-aliasing filter and an amplifier configured to receive electromyography sensor signals from the one or more electrodes; a shielding layer configured to shield the analog circuit from electromagnetic radiation; an analog-to-digital converter (ADC) configured to receive analog sensor signals from the analog circuit and provide digital sensor signals; a processor configured to receive the digital sensor signals and provide control signals based on the digital sensor signals; a magnetic tracking system receiver; and a control device antenna configured to transmit the control signals to the head-mounted device, wherein the head-mounted device is configured to modify the extended reality view in response to the control signals.

Embodiments of the present disclosure may include or be implemented in conjunction with various types of artificial reality systems. Artificial reality is a form of reality that has been adjusted in some manner before presentation to a user, that may include, for example, a virtual reality, an augmented reality, a mixed reality, a hybrid reality, or some combination and/or derivative thereof. Artificial-reality content may include completely computer-generated content or computer-generated content combined with captured (e.g., real-world) content. The artificial-reality content may include video, audio, haptic feedback, or some combination thereof, any of that may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, for example, create content in an artificial reality and/or are otherwise used in (e.g., to perform activities in) an artificial reality.

Artificial-reality systems may be implemented in a variety of different form factors and configurations. Some artificial reality systems may be designed to work without near-eye displays (NEDs). Other artificial reality systems may include an NED that also provides visibility into the real world (e.g., augmented-reality system 1300 in FIG. 13) or that visually immerses a user in an artificial reality (e.g., virtual-reality system 1400 in FIG. 14). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Figure 13:
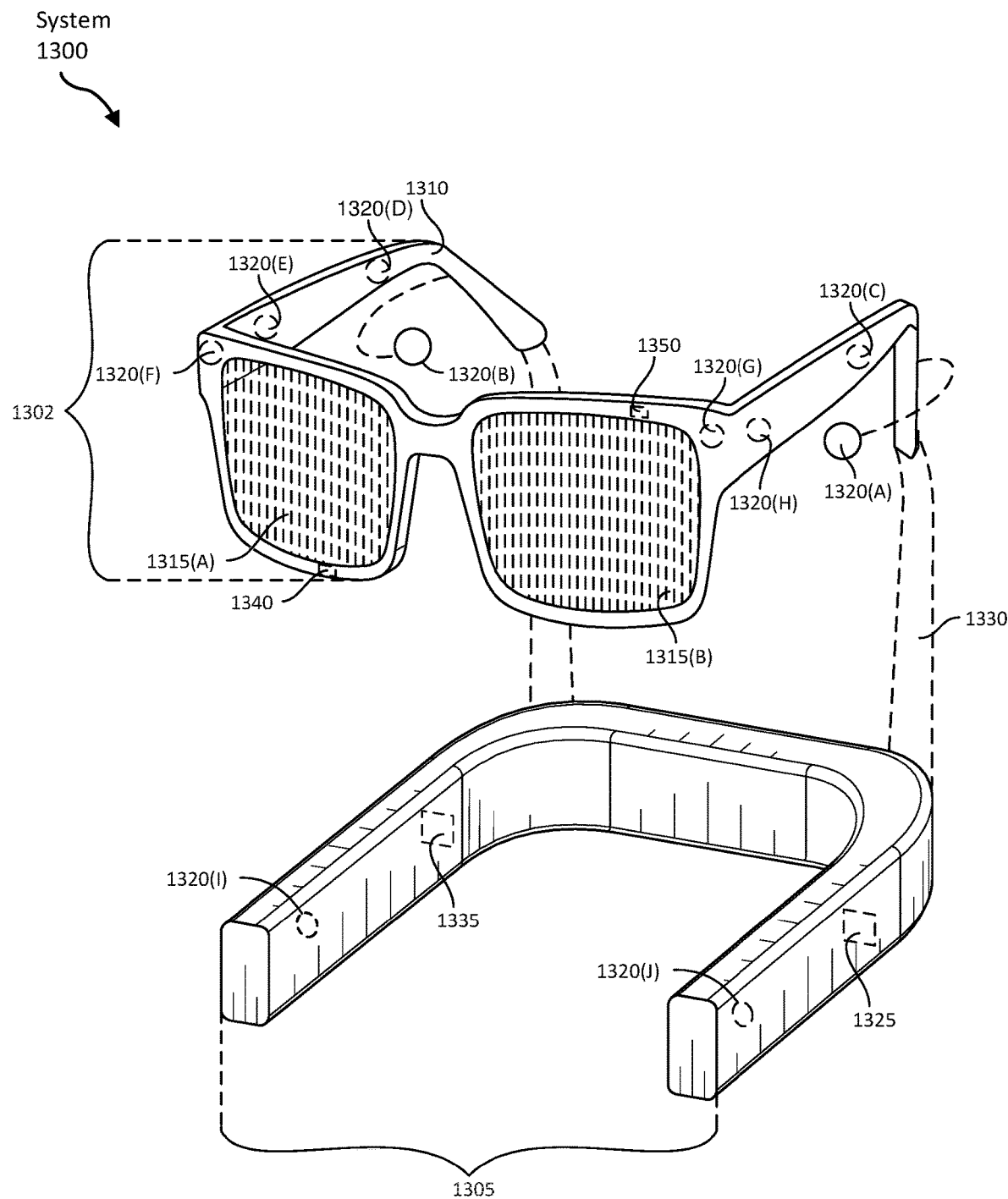
FIG. 13 is an illustration of exemplary augmented-reality glasses that may be used in connection with embodiments of this disclosure.
Figure 14:
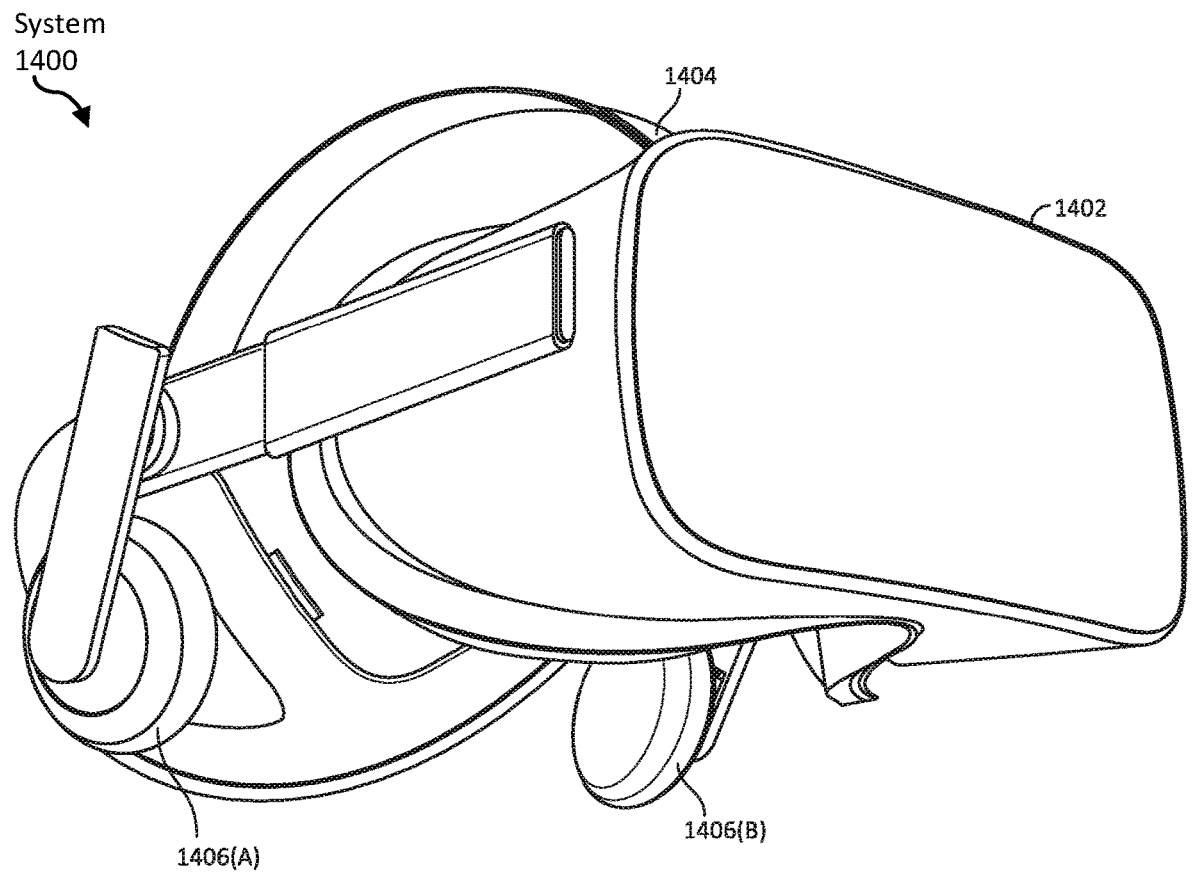
FIG. 14 is an illustration of an exemplary virtual-reality headset that may be used in connection with embodiments of this disclosure.

Turning to FIG. 13, augmented-reality system 1300 may include an eyewear device 1302 with a frame 1310 configured to hold a left display device 1315(A) and a right display device 1315(B) in front of a user's eyes. Display devices 1315(A) and 1315(B) may act together or independently to present an image or series of images to a user. While augmented-reality system 1300 includes two displays, embodiments of this disclosure may be implemented in augmented-reality systems with a single NED or more than two NEDs.

In some embodiments, augmented-reality system 1300 may include one or more sensors, such as sensor 1340. Sensor 1340 may represent one or more sensors, of the same or different sensing modalities. Sensor 1340 may generate measurement signals in response to the motion of augmented-reality system 1300, and may be located on substantially any portion of frame 1310. Sensor 1340 may represent one or more of a position sensor, an inertial sensor such as an inertial measurement unit (IMU), a depth camera assembly, a structured light emitter and/or detector, or any combination thereof. In some embodiments, augmented-reality system 1300 may or may not include sensor 1340 or may include more than one sensor. In some embodiments, sensor 1340 may include an IMU, and the IMU may generate calibration data based on measurement signals from sensor 1340. Examples of sensor 1340 may include, without limitation, accelerometers, gyroscopes, magnetometers, other suitable types of sensors that detect motion, sensors used for error correction of the IMU, or some combination thereof. Augmented-reality system 1300 may also include a microphone array with a plurality of acoustic transducers 1320(A)-1320(J), referred to collectively as acoustic transducers 1320. Acoustic transducers 1320 may be transducers that detect air pressure variations induced by sound waves. Each acoustic transducer 1320 may be configured to detect sound and convert the detected sound into an electronic format (e.g., an analog or digital format). The microphone array in FIG. 13 may include, for example, ten acoustic transducers: 1320(A) and 1320(B), that may be designed to be placed inside a corresponding ear of the user, acoustic transducers 1320(C), 1320(D), 1320(E), 1320(F), 1320(G), and 1320(H), that may be positioned at various locations on frame 1310, and/or acoustic transducers 1320(I) and 1320(J), that may be positioned on a corresponding neckband 1305.

In some embodiments, one or more of acoustic transducers 1320(A)-(F) may be used as output transducers (e.g., speakers). For example, acoustic transducers 1320(A) and/or 1320(B) may be earbuds or any other suitable type of headphone or speaker.

The configuration of acoustic transducers 1320 of the microphone array may vary. While augmented-reality system 1300 is shown in FIG. 13 as having ten acoustic transducers 1320, the number of acoustic transducers 1320 may be greater or less than ten. In some embodiments, using higher numbers of acoustic transducers 1320 may increase the amount of audio information collected and/or the sensitivity and accuracy of the audio information. In contrast, using a lower number of acoustic transducers 1320 may decrease the computing power required by an associated controller 1350 to process the collected audio information. In addition, the position of each acoustic transducer 1320 of the microphone array may vary. For example, the position of an acoustic transducer 1320 may include a defined position on the user, a defined coordinate on frame 1310, an orientation associated with each acoustic transducer 1320, or some combination thereof.

Acoustic transducers 1320(A) and 1320(B) may be positioned on different parts of the user's ear, such as behind the pinna, behind the tragus, and/or within the auricle or fossa. Or, there may be additional acoustic transducers 1320 on or surrounding the ear in addition to acoustic transducers 1320 inside the ear canal. Having an acoustic transducer 1320 positioned next to an ear canal of a user may enable the microphone array to collect information on how sounds arrive at the ear canal. By positioning at least two of acoustic transducers 1320 on either side of a user's head (e.g., as binaural microphones), augmented-reality device 1300 may simulate binaural hearing and capture a 3D stereo sound field around about a user's head. In some embodiments, acoustic transducers 1320(A) and 1320(B) may be connected to augmented-reality system 1300 via a wired connection 1330, and in other embodiments acoustic transducers 1320(A) and 1320(B) may be connected to augmented-reality system 1300 via a wireless connection (e.g., a BLUETOOTH connection). In still other embodiments, acoustic transducers 1320(A) and 1320(B) may not be used at all in conjunction with augmented-reality system 1300.

Acoustic transducers 1320 on frame 1310 may be positioned along the length of the temples, across the bridge, above or below display devices 1315(A) and 1315(B), or some combination thereof. Acoustic transducers 1320 may be oriented such that the microphone array is able to detect sounds in a wide range of directions surrounding the user wearing the augmented-reality system 1300. In some embodiments, an optimization process may be performed during manufacturing of augmented-reality system 1300 to determine relative positioning of each acoustic transducer 1320 in the microphone array.

In some examples, augmented-reality system 1300 may include or be connected to an external device (e.g., a paired device), such as neckband 1305. Neckband 1305 generally represents any type or form of paired device. Thus, the following discussion of neckband 1305 may also apply to various other paired devices, such as charging cases, smart watches, smart phones, wrist bands, other wearable devices, hand-held controllers, tablet computers, laptop computers, other external computer devices, etc.

As shown, neckband 1305 may be coupled to eyewear device 1302 via one or more connectors. The connectors may be wired or wireless and may include electrical and/or non-electrical (e.g., structural) components. In some cases, eyewear device 1302 and neckband 1305 may operate independently without any wired or wireless connection between them. While FIG. 13 illustrates the components of eyewear device 1302 and neckband 1305 in example locations on eyewear device 1302 and neckband 1305, the components may be located elsewhere and/or distributed differently on eyewear device 1302 and/or neckband 1305.

In some embodiments, the components of eyewear device 1302 and neckband 1305 may be located on one or more additional peripheral devices paired with eyewear device 1302, neckband 1305, or some combination thereof.

Pairing external devices, such as neckband 1305, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 1300 may be provided by a paired device or shared between a paired device and an eyewear device, thus reducing the weight, heat profile, and form factor of the eyewear device overall while still retaining desired functionality. For example, neckband 1305 may allow components that would otherwise be included on an eyewear device to be included in neckband 1305 since users may tolerate a heavier weight load on their shoulders than they would tolerate on their heads. Neckband 1305 may also have a larger surface area over which to diffuse and disperse heat to the ambient environment. Thus, neckband 1305 may allow for greater battery and computation capacity than might otherwise have been possible on a stand-alone eyewear device. Since weight carried in neckband 1305 may be less invasive to a user than weight carried in eyewear device 1302, a user may tolerate wearing a lighter eyewear device and carrying or wearing the paired device for greater lengths of time than a user would tolerate wearing a heavy stand-alone eyewear device, thereby enabling users to more fully incorporate artificial reality environments into their day-to-day activities.

Neckband 1305 may be communicatively coupled with eyewear device 1302 and/or to other devices. These other devices may provide certain functions (e.g., tracking, localizing, depth mapping, processing, storage, etc.) to augmented-reality system 1300. In the embodiment of FIG. 13, neckband 1305 may include two acoustic transducers (e.g., 1320(I) and 1320(J)) that are part of the microphone array (or potentially form their own microphone subarray). Neckband 1305 may also include a controller 1325 and a power source 1335.

Acoustic transducers 1320(I) and 1320(J) of neckband 1305 may be configured to detect sound and convert the detected sound into an electronic format (analog or digital). In the embodiment of FIG. 13, acoustic transducers 1320(I) and 1320(J) may be positioned on neckband 1305, thereby increasing the distance between the neckband acoustic transducers 1320(I) and 1320(J) and other acoustic transducers 1320 positioned on eyewear device 1302. In some cases, increasing the distance between acoustic transducers 1320 of the microphone array may improve the accuracy of beamforming performed via the microphone array. For example, if a sound is detected by acoustic transducers 1320(C) and 1320(D) and the distance between acoustic transducers 1320(C) and 1320(D) is greater than, for example, the distance between acoustic transducers 1320(D) and 1320(E), the determined source location of the detected sound may be more accurate than if the sound had been detected by acoustic transducers 1320(D) and 1320(E).

Controller 1325 of neckband 1305 may process information generated by the sensors on neckband 1305 and/or augmented-reality system 1300. For example, controller 1325 may process information from the microphone array that describes sounds detected by the microphone array. For each detected sound, controller 1325 may perform a direction-of-arrival (DOA) estimation to estimate a direction from which the detected sound arrived at the microphone array. As the microphone array detects sounds, controller 1325 may populate an audio data set with the information. In embodiments in which augmented-reality system 1300 includes an inertial measurement unit, controller 1325 may compute all inertial and spatial calculations from the IMU located on eyewear device 1302. A connector may convey information between augmented-reality system 1300 and neckband 1305 and between augmented-reality system 1300 and controller 1325. The information may be in the form of optical data, electrical data, wireless data, or any other transmittable data form. Moving the processing of information generated by augmented-reality system 1300 to neckband 1305 may reduce weight and heat in eyewear device 1302, making it more comfortable to the user.

Power source 1335 in neckband 1305 may provide power to eyewear device 1302 and/or to neckband 1305. Power source 1335 may include, without limitation, lithium ion batteries, lithium-polymer batteries, primary lithium batteries, alkaline batteries, or any other form of power storage. In some cases, power source 1335 may be a wired power source. Including power source 1335 on neckband 1305 instead of on eyewear device 1302 may help better distribute the weight and heat generated by power source 1335.

As noted, some artificial reality systems may, instead of blending an artificial reality with actual reality, substantially replace one or more of a user's sensory perceptions of the real world with a virtual experience. One example of this type of system is a head-worn display system, such as virtual-reality system 1400 in FIG. 14, that mostly or completely covers a user's field of view. Virtual-reality system 1400 may include a front rigid body 1402 and a band 1404 shaped to fit around a user's head. Virtual-reality system 1400 may also include output audio transducers 1406(A) and 1406(B). Furthermore, while not shown in FIG. 14, front rigid body 1402 may include one or more electronic elements, including one or more electronic displays, one or more inertial measurement units (IMUs), one or more tracking emitters or detectors, and/or any other suitable device or system for creating an artificial reality experience.

Artificial reality systems may include a variety of types of visual feedback mechanisms. For example, display devices in augmented-reality system 1300 and/or virtual-reality system 1400 may include one or more liquid crystal displays (LCDs), light emitting diode (LED) displays, organic LED (OLED) displays digital light project (DLP) micro-displays, liquid crystal on silicon (LCoS) micro-displays, and/or any other suitable type of display screen. Artificial reality systems may include a single display screen for both eyes or may provide a display screen for each eye, that may allow for additional flexibility for varifocal adjustments or for correcting a user's refractive error. Some artificial reality systems may also include optical subsystems having one or more lenses (e.g., conventional concave or convex lenses, Fresnel lenses, adjustable liquid lenses, etc.) through which a user may view a display screen. These optical subsystems may serve a variety of purposes, including to collimate (e.g., make an object appear at a greater distance than its physical distance), to magnify (e.g., make an object appear larger than its actual size), and/or to relay (to, e.g., the viewer's eyes) light. These optical subsystems may be used in a non-pupil-forming architecture (such as a single lens configuration that directly collimates light but results in so-called pincushion distortion) and/or a pupil-forming architecture (such as a multi-lens configuration that produces so-called barrel distortion to nullify pincushion distortion).

In addition to or instead of using display screens, some artificial reality systems may include one or more projection systems. For example, display devices in augmented-reality system 1300 and/or virtual-reality system 1400 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial reality content and the real world. The display devices may accomplish this using any of a variety of different optical components, including waveguides components (e.g., holographic, planar, diffractive, polarized, and/or reflective waveguide elements), light-manipulation surfaces and elements (such as diffractive, reflective, and refractive elements and gratings), coupling elements, etc. Artificial reality systems may also be configured with any other suitable type or form of image projection system, such as retinal projectors used in virtual retina displays.

Artificial reality systems may also include various types of computer vision components and subsystems. For example, augmented-reality system augmented-reality system 1300 and/or virtual-reality system 1400 may include one or more optical sensors, such as two-dimensional (2D) or 3D cameras, structured light transmitters and detectors, time-of-flight depth sensors, single-beam or sweeping laser rangefinders, 3D LiDAR sensors, and/or any other suitable type or form of optical sensor. An artificial reality system may process data from one or more of these sensors to identify a location of a user, to map the real world, to provide a user with context about real-world surroundings, and/or to perform a variety of other functions.

Artificial reality systems may also include one or more input and/or output audio transducers. In the examples shown in FIG. 1 1406(A), and 1406(B) may include voice coil speakers, ribbon speakers, electrostatic speakers, piezoelectric speakers, bone conduction transducers, cartilage conduction transducers, tragus-vibration transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

While not shown in FIG. 13, artificial reality systems may include tactile (i.e., haptic) feedback systems, that may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial reality devices, within other artificial reality devices, and/or in conjunction with other artificial reality devices.

By providing haptic sensations, audible content, and/or visual content, artificial reality systems may create an entire virtual experience or enhance a user's real-world experience in a variety of contexts and environments. For instance, artificial reality systems may assist or extend a user's perception, memory, or cognition within a particular environment. Some systems may enhance a user's interactions with other people in the real world or may enable more immersive interactions with other people in a virtual world. Artificial reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visuals aids, etc.). The embodiments disclosed herein may enable or enhance a user's artificial reality experience in one or more of these contexts and environments and/or in other contexts and environments.

Some augmented reality systems may map a user's and/or device's environment using techniques referred to as "simultaneous location and mapping" (SLAM). SLAM mapping and location identifying techniques may involve a variety of hardware and software tools that can create or update a map of an environment while simultaneously keeping track of a user's location within the mapped environment. SLAM may use many different types of sensors to create a map and determine a user's position within the map. Data from magnetic trackers may be used to create the map and determine the position of the user, and of portions of the user's body, within the mapped environment.

SLAM techniques may, for example, implement optical sensors to determine a user's location. Radios including WiFi, BLUETOOTH, global positioning system (GPS), cellular or other communication devices may be also used to determine a user's location relative to a radio transceiver or group of transceivers (e.g., a WiFi router or group of GPS satellites). Acoustic sensors such as microphone arrays or 2D or 3D sonar sensors may also be used to determine a user's location within an environment. Augmented reality and virtual reality devices (such as systems 1300 and 1400 of FIGS. 13 and 14, respectively) may incorporate any or all of these types of sensors to perform SLAM operations such as creating and continually updating maps of the user's current environment. In at least some of the embodiments described herein, SLAM data generated by these sensors may be referred to as "environmental data" and may indicate a user's current environment. This data may be stored in a local or remote data store (e.g., a cloud data store) and may be provided to a user's AR/VR device on demand.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the modules described herein may transform data, physical devices, and/or representations of physical devices from one form to another. For example, one or more of the modules recited herein may receive data to be transformed, transform the data, output a result of the transformation to perform a function, use the result of the transformation to perform a function, and store the result of the transformation to perform a function. Data may include physiological data from a user, such as neuromuscular signals, eye tracking data, or other data. A function may include control of a computerized device, selection and/or control of objects within an environment, such as an augmented reality environment, and the like. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The process parameters and sequence of the steps described and/or illustrated herein are given by way of example only and may be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "including."

What is claimed is:

1. An apparatus, comprising:
   a head-mounted device that, when worn by a user, is configured to present an extended reality view to the user; and
   a control device comprising one or more electrodes that, when worn on a wrist of the user, contact the skin of the user, the control device comprising:
      an analog circuit including an amplifier configured to receive sensor signals from the one or more electrodes and an anti-aliasing filter;
      an analog-to-digital converter (ADC) configured to receive analog sensor signals from the analog circuit and provide digital sensor signals, wherein the anti-aliasing filter is located proximate the ADC such that an electrical connection between the anti-aliasing filter and the ADC is approximately 1.5 cm or less;
      a processor configured to receive the digital sensor signals and provide control signals based on the digital sensor signals; and
      a control device antenna configured to transmit the control signals to the head-mounted device,
      wherein the head-mounted device is configured to modify the extended reality view in response to the control signals.

2. The apparatus of claim 1, wherein the amplifier comprises a differential amplifier configured to remove electromagnetic noise generated within the analog circuit.

3. The apparatus of claim 2, wherein the differential amplifier comprises a fully differential amplifier.

4. The apparatus of claim 1, wherein the ADC comprises a differential ADC configured to remove electromagnetic noise generated within the analog circuit.

5. The apparatus of claim 1, wherein the analog circuit includes a plurality of analog channels, and each analog channel has an associated one of a plurality of ADCs, wherein the plurality of ADCs includes the ADC.

6. The apparatus of claim 1, wherein the amplifier is located proximate the ADC such that an electrical connection between an output of the amplifier and an input of the ADC is less than approximately 3 mm.

7. The apparatus of claim 1, further comprising a magnetic tracker comprising a transmitter and a plurality of receivers.

8. The apparatus of claim 7, wherein the transmitter of the magnetic tracker is supported by the head-mounted device.

9. The apparatus of claim 7, wherein at least one of the plurality of receivers of the magnetic tracker is configured to determine an orientation of a finger of the user.

10. The apparatus of claim 7, wherein:
    the plurality of receivers of the magnetic tracker are located within a control glove configured to be worn on a hand of the user, and
    the control glove is in communication with the control device.

11. The apparatus of claim 1, wherein the control device includes a shielding layer configured to shield the analog circuit from electromagnetic radiation.

12. The apparatus of claim 11, wherein the shielding layer includes a ferrite material.

13. The apparatus of claim 11, wherein the shielding layer comprises at least one of the following: a metal layer, alloy layer, conductive polymer, carbon-filled nylon, conductive paint, conductive fabric, conductive plastic, conductive rubber, and/or conductive silicone.

14. The apparatus of claim 1, wherein the head-mounted device comprises at least one of a virtual-reality headset or augmented reality spectacles.

15. The apparatus of claim 1, wherein the control device includes one or more electromyography sensors, wherein:
    the one or more electromyography sensors include the one or more electrodes, and
    the one or more sensors provides the sensor signals received by the analog circuit.

16. The apparatus of claim 1, wherein the processor further receives inertial sensor signals from an inertial sensor, and the control signals are based on the digital sensor signals and the inertial sensor signals.

17. An apparatus, comprising:
    a head-mounted device that includes a magnetic tracking system transmitter, and when worn by a user, is configured to present an extended reality view to the user;
    a control device comprising one or more electromyography electrodes that contact the skin of the user when worn by the user, the control device comprising:
       an analog circuit including an anti-aliasing filter and an amplifier configured to receive electromyography sensor signals from the one or more electrodes;
       a shielding layer configured to shield the analog circuit from electromagnetic radiation produced by the magnetic tracking system transmitter;
       an analog-to-digital converter (ADC) configured to receive analog sensor signals from the analog circuit and provide digital sensor signals, wherein the anti-aliasing filter is located proximate the ADC such that an electrical connection between the anti-aliasing filter and the ADC is approximately 1.5 cm or less;
       a processor configured to receive the digital sensor signals and provide control signals based on the digital sensor signals;
       a magnetic tracking system receiver; and
       a control device antenna configured to transmit the control signals to the head-mounted device,
       wherein the head-mounted device is configured to modify the extended reality view in response to the control signals.

18. An apparatus, comprising:
    a head-mounted device that, when worn by a user, is configured to present an extended reality view to the user; and
    a control device comprising one or more electrodes that, when worn on a wrist of the user, contact the skin of the user, the control device comprising:
       an analog circuit including an amplifier configured to receive sensor signals from the one or more electrodes;

an analog-to-digital converter (ADC) configured to receive analog sensor signals from the analog circuit and provide digital sensor signals, wherein the amplifier is located proximate the ADC such that an electrical connection between an output of the amplifier and an input of the ADC is less than approximately 3 mm;

a processor configured to receive the digital sensor signals and provide control signals based on the digital sensor signals; and a control device antenna configured to transmit the control signals to the head-mounted device, wherein the head-mounted device is configured to modify the extended reality view in response to the control signals.

19. The apparatus of claim 18, wherein the amplifier comprises a differential amplifier configured to remove electromagnetic noise generated within the analog circuit.

20. The apparatus of claim 18, wherein the analog circuit includes an anti-aliasing filter.

21. The apparatus of claim 20, wherein the anti-aliasing filter is located proximate the ADC such that an electrical connection between the anti-aliasing filter and the ADC is approximately 1.5 cm or less.

22. The apparatus of claim 18, wherein the control device further comprises a magnetic tracking system transmitter.

* * * * *